(12) United States Patent
Oniciu et al.

(10) Patent No.: US 10,227,285 B2
(45) Date of Patent: Mar. 12, 2019

(54) PROCESSES AND INTERMEDIATES FOR PREPARING ALPHA,OMEGA-DICARBOXYLIC ACID-TERMINATED DIALKANE ETHERS

(71) Applicant: Gemphire Therapeutics Inc., Livonia, MI (US)

(72) Inventors: Carmen Daniela Oniciu, Toulouse (FR); Otto Joseph Geoffroy, Gainesville, FL (US)

(73) Assignee: GEMPHIRE THERAPEUTICS INC., Livonia, MI (US)

( * ) Notice: Subject to any disclaimer, the term of this patent is extended or adjusted under 35 U.S.C. 154(b) by 0 days.

(21) Appl. No.: 14/942,765

(22) Filed: Nov. 16, 2015

(65) Prior Publication Data

US 2016/0137584 A1 May 19, 2016
US 2017/0158601 A9 Jun. 8, 2017

Related U.S. Application Data

(60) Provisional application No. 62/079,894, filed on Nov. 14, 2014.

(51) Int. Cl.
| | | |
|---|---|---|
| *C07C 67/31* | (2006.01) | |
| *C07C 51/09* | (2006.01) | |
| *C07C 67/307* | (2006.01) | |
| *C07C 67/343* | (2006.01) | |
| *C07C 51/41* | (2006.01) | |
| *C07C 51/43* | (2006.01) | |
| *C07D 309/12* | (2006.01) | |
| *C07D 313/04* | (2006.01) | |

(52) U.S. Cl.
CPC ............ *C07C 67/31* (2013.01); *C07C 51/09* (2013.01); *C07C 51/412* (2013.01); *C07C 51/43* (2013.01); *C07C 67/307* (2013.01); *C07C 67/343* (2013.01); *C07D 309/12* (2013.01); *C07D 313/04* (2013.01)

(58) Field of Classification Search
CPC ....... C07C 51/09; C07C 59/58; C07C 67/343; C07C 69/708; C07C 67/31; C07C 51/412; C07C 51/43; C07C 67/307; C07C 59/64; C07C 69/63; C07C 69/734; C07C 41/24; C07C 51/347; C07C 59/305; C07C 67/303; C07D 309/12; C07D 313/04; A61K 31/519; A61K 47/08; A61K 47/10; A61K 9/0056; A61K 9/0058; A61K 9/006; A61K 9/08; H01Q 1/288; H01Q 1/36; H01Q 5/55
See application file for complete search history.

(56) References Cited

U.S. PATENT DOCUMENTS

| | | | |
|---|---|---|---|
| 2,033,909 A | 3/1936 | Cox et al. | |
| 4,691,034 A | 9/1987 | Sanderson et al. | |
| 5,133,974 A | 7/1992 | Paradissis et al. | |
| 5,648,387 A | 7/1997 | Bisgaier et al. | |
| 6,410,802 B1 | 6/2002 | Dasseux et al. | |
| 6,500,457 B1 | 12/2002 | Midha et al. | |
| 6,861,555 B2 * | 3/2005 | Ando .................... | C07C 59/305 562/568 |

(Continued)

FOREIGN PATENT DOCUMENTS

| | | |
|---|---|---|
| CA | 1197242 | 11/1985 |
| WO | WO 1996/030328 | 10/1996 |

(Continued)

OTHER PUBLICATIONS

Hydrolysis (pp. 1-4, 2004).*

(Continued)

*Primary Examiner* — Yevgeny Valenrod
*Assistant Examiner* — Blaine G Doletski
(74) *Attorney, Agent, or Firm* — Cooley LLP

(57) ABSTRACT

The present disclosure provides a process for the preparation of compounds of formula (III),

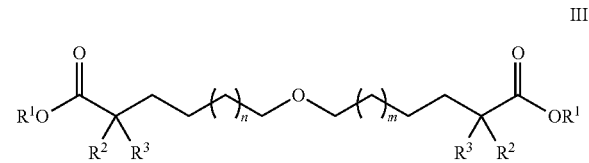

compounds of formula (V),

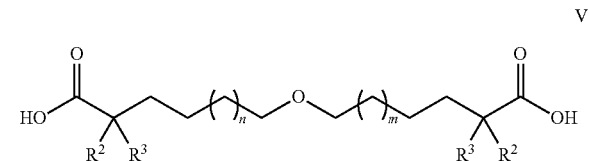

and corresponding salts of formula (IV).

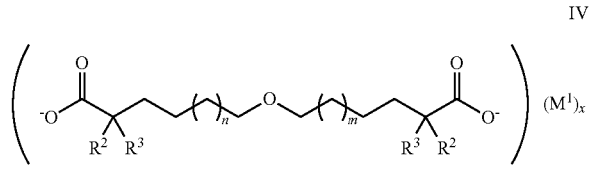

The compounds made by the methods and processes of the invention are particularly useful for administration in humans and animals.

14 Claims, No Drawings

(56) References Cited

U.S. PATENT DOCUMENTS

| | | | |
|---|---|---|---|
| 6,909,014 | B2 | 6/2005 | Dasseux et al. |
| 7,510,729 | B2 | 3/2009 | Kolter et al. |
| 7,777,071 | B2 | 8/2010 | Goel |
| 9,486,446 | B2 | 11/2016 | Kurasawa et al. |
| 9,849,104 | B2 | 12/2017 | Bisgaier et al. |
| 2004/0167229 | A1* | 8/2004 | Bakker-Arkema ......... A61K 31/075 514/675 |
| 2004/0192771 | A1 | 9/2004 | Dasseux et al. |
| 2005/0004196 | A1 | 1/2005 | Kowala |
| 2008/0069873 | A1 | 3/2008 | Pearnchob et al. |
| 2009/0208539 | A1 | 8/2009 | Penhasi et al. |
| 2009/0220611 | A1 | 9/2009 | Dargelas et al. |
| 2009/0220613 | A1 | 9/2009 | Odidi et al. |
| 2009/0226515 | A1 | 9/2009 | Schmitt et al. |
| 2010/0015220 | A1 | 1/2010 | Wetterau et al. |
| 2010/0196569 | A1* | 8/2010 | Scanlin ............... A23L 5/21 426/464 |
| 2010/0247639 | A1 | 9/2010 | Ravishankar et al. |
| 2011/0171112 | A1 | 7/2011 | Armand et al. |
| 2012/0164221 | A1 | 6/2012 | Bova et al. |
| 2012/0165411 | A1 | 6/2012 | Bisgaier |
| 2013/0123354 | A1 | 5/2013 | Currie et al. |
| 2013/0273157 | A1 | 10/2013 | Ishii et al. |
| 2014/0154313 | A1 | 6/2014 | Counts et al. |
| 2014/0371314 | A1 | 12/2014 | Bar-Tana |
| 2015/0005386 | A1 | 1/2015 | Bisgaier |
| 2015/0094303 | A1 | 4/2015 | Bachovchin et al. |
| 2015/0283202 | A1 | 10/2015 | Shailubhai |
| 2017/0158601 | A9 | 6/2017 | Oniciu et al. |
| 2018/0194713 | A1 | 7/2018 | Oniciu et al. |
| 2018/0297929 | A1 | 10/2018 | Oniciu et al. |
| 2018/0325825 | A1 | 11/2018 | Oniciu et al. |

FOREIGN PATENT DOCUMENTS

| | | | |
|---|---|---|---|
| WO | WO 2000/059855 | | 10/2000 |
| WO | WO200155078 | * | 8/2001 |
| WO | WO 2002/030922 | | 4/2002 |
| WO | WO 2009/135949 | | 11/2009 |
| WO | WO 2009/140341 | | 11/2009 |
| WO | WO2012117071 | * | 9/2012 |
| WO | 2013084237 | A1 | 6/2013 |
| WO | WO 2017/079755 | | 5/2017 |

OTHER PUBLICATIONS

Sisido et al. (Condensation of t-Butyl Esters with Organic Halides in the Presence of Alkali Amides, pp. 5817-5819, 1959).*

Saponification (pp. 1-3, 2003).*

MIT (pp. 1-5, 2004).*

Adel Amer, (Published Feb. 2014, downloaded from the internet Apr. 17, 2017).*

Green et al. (Green and Wuts, chapter 5 Protection of the Carboxyl Group, published online 2006, (p. 582-588)).*

DA (Direct Alkylation of Simple enolates, pp. 1-9, 2010).*

Schwindeman et al. (Safe Handling of organolithium compounds in the laboratory, Chemical health and Safety, published 2002).*

Clayden, pp. 663-688 (Year: 2008).*

Clayden 2012,p. 348 (Year: 2012).*

DA (Direct Alkylation of Simple enolates, pp. 1-9, 2010) (Year: 2010).*

Clayden et al. (Organic Chemistry, Alkylation of Enolates, chapter 26, pp. 588-589, Published 2012) (Year: 2012).*

Adel Amer, Published Feb. 2014) (Year: 2014).*

Schwindeman et al. (Safe Handling of organolithium compounds in the laboratory, Chemical health and Safety, published 2002) (Year: 2002).*

Weber, Edwin, "Neutralliganden mit Tensidstruktur—Synthese, Komplexierung, Ionentransfer", Liebigs Ann. Chem., 1983, pp. 770-801.

Gomez-Bombarelli, Rafael, et al. "Mechanisms of Lactone Hydrolysis in Acidic Conditions" The Journal of Organic Chemistry, 2013, vol. 78, pp. 6880-6889.

Gomez-Bombarelli, Rafael, et al. "Mechanisms of Lactone Hydrolysis in Neutral and Alkaline Conditions" The Journal of Organic Chemistry, 2013, vol. 78, pp. 6868-6879.

Gleiter, Rolf, et al. "Synthesis of 5,5,10,10-Tetramethyl-1-oxacyclotridecane-6,7,8,9-tetrone—On the Mechanism of the Rubottom Reaction", Liebigs Ann. 1995, pp. 1655-1661.

Mueller, Ralf, et al. "Long Hydrocarbon Chain Ether Diols and Ether Diacids That Favorably Alter Lipid Disorders in Vivo", J. Med. Chem. 2004, vol. 47, pp. 5183-5197.

International Search Report and Written Opinion of PCT/US2015/060917, dated May 13, 2016.

International Search Report and Written Opinion for International Application No. PCT/US2016/060849, dated Mar. 13, 2017, 21 pages.

Yang, J. et al., "Kilogram-Scale Synthesis of bis(6-Hydroxy-5,5-Dimethylhexyl)ether (ESP24232), a Novel Lipid Lowering Agent," Organic Preparations and Procedures International, The New Journal for Organic Synthesis, vol. 36(6): 587-596 (2004); Accepted Nov. 10, 2004, Published online: Feb. 11, 2009.

Mueller, R. et al., "Long Hydrocarbon Chain Ether Diols and Ether Diacids That Favorably Alter Lipid Disorders in Vivo," J. Med. Chem. 2004, 47, 5183-5197.

International Search Report and Written Opinion for International Application No. PCT/US2018/032351, dated Aug. 8, 2018, 9 pages.

Dalko, P. I. et al., "Stereoselective Synthesis of Quaternary Benzylic Carbons Using $C_2$ Symmetric Imidazolines and Tetrahydrofuran as Electrophile," J. Org. Chem., 1998, vol. 63, No. 23, pp. 8107-8117.

International Preliminary Report on Patentability for International Application No. PCT/US2016/060849, dated May 8, 2018, 17 pages.

Ballantyne, C. M. et al., "Effect of Ezetimibe Coadministered With Atorvastatin in 628 Patients With Primary Hypercholesterolemia. A Prospective, Randomized, Double-Blind Trial." Circulation, 2003;107:2409-2415.

Bhasin, R. K. et al., "Design & Development of Atorvastatin Orally Disintegrating Tablets & Their Evaluation by Electronic Tongue," Drug Development & Delivery [Online], Retrieved from the Internet: <URL: http://www.drug-dev.com/Main/Back-Issues/Design-Development-of-Atorvastatin-Orally-Disinteg-446.aspx>, Apr. 2012.

Billecke, S. et al., "Human serum paraoxonase (PON1) isozymes Q and R hydrolyze lactones and cyclic carbonate esters," Drug Metabolism and Disposition, vol. 28, No. 11, pp. 1335-1342 (2000).

Bisgaier, C. L. et al., "A novel compound that elevates high density lipoprotein and activates the peroxisome proliferator activated receptor," Journal of Lipid Research, 39:17-30 (1998).

Blonk, M. et al., "Pharmacokinetic Drug—Drug Interaction Study Between Raltegravir and Atorvastatin 20 mg in Healthy Volunteers," J Acquir Immune Defic Syndr 2015;69:44-51.

Boyd, R. A. et al., "Atorvastatin coadministration may increase digoxin concentrations by inhibition of intestinal P-glycoprotein-mediated secretion," Journal of Clinical Pharmacology, 2000; 40:91-98.

Castañeda, P. S. et al., "Design and evaluation of a transdermal patch with atorvastatin," Farmacia, 2017, vol. 65, No. 6, pp. 908-916.

Bisgaier, C. L. et al., "125: 328104r Preparation of terminal carboxy or tetrazole group-containing dialkyl ethers as anticholesteremics and antidiabetics," Chemical Abstracts, 23-Aliphatic Compounds 328108, vol. 125, No. 25, p. 1337 (1996).

Di Stasi, S. L. et al., "Effects of Statins on Skeletal Muscle: A Perspective for Physical Therapists," Phys Ther. Oct. 2010; 90(10): 1530-1542.

Dressman, J. B., "Comparison of canine and human gastrointestinal physiology," Pharmaceutical Research, vol. 3, No. 3, 1986, pp. 123-131.

Gite, S. et al., "Development and Validation of a Discriminating Dissolution Method for Atorvastatin Delayed-Release Nanoparticles Using a Flow-Through Cell: A Comparative Study Using USP Apparatus 4 and 1," Dissolution Technologies, 23(2):14-20; May 2016.

(56) References Cited

OTHER PUBLICATIONS

Hajir, M. et al., "Stable amorphous calcium oxalate: synthesis and potential intermediate in biomineralization," Chem. Commun. 2014, 50:6534-6536.

Hayashi, K. et al., "Studies on angiotensin converting enzyme inhibitors. II. Syntheses and angiotensin converting enzyme inhibitory activities of carboxyethylcarbamoyl-1,2,3,4-tetrahydroisoquinoline-3-carboxylic acid derivatives," Chemical and Pharmaceutical Bulletin, vol. 31, No. 10, pp. 3553-3561 (1983).

Hermann, M. et al., "Exposure of atorvastatin is unchanged but lactone and acid metabolites are increased several-fold in patients with atorvastatin-induced myopathy," Clin. Pharmacol. Ther. 2006;79:532-539.

Ireland, R. E. et al., "132. Diels-Alder Approach to Highly Functionalized Tertiary α-Hydroxy Ketones: A Novel Route to the Hexahydrobenzofuran Portion of the Avermectins and Milbemycins," Helv. Chim. Acta 1986, 69:1273-1286.

Kakurkin, N. P. et al., "Solutions in the Calcium Oxide-Ethylene Glycol-Water System," ISSN 1070-4272, Russian Journal of Applied Chemistry, 2007, vol. 80, No. 5, pp. 722-725, Pleiades Publishing, Ltd., 2007. Original Russian Text, N.P. Kakurkin, A.D. Kirillov, V.V. Shcherbakov, 2007, published in Zhurnal Prikladnoi Khimii, 2007, vol. 80, No. 5, pp. 743-746.

Kearney, A. S. et al., "The interconversion kinetics, equilibrium, and solubilities of the lactone and hydroxyacid forms of the HMG-CoA reductase inhibitor, CI-981," Pharmaceutical Research, vol. 10, No. 10, 1993, pp. 1461-1465.

Khare, A. R. et al., "Swelling/deswelling of anionic copolymer gels," Biomaterials 16 (1995) 559-567.

König, J. et al., "Localization and Genomic Organization of a New Hepatocellular Organic Anion Transporting Polypeptide," The Journal of Biological Chemistry, vol. 275, No. 30, Jul. 28, 2000, pp. 23161-23168.

Kotame, R. N. et al., "Formulation and Evaluation of Microspheres of Atorvastatin Calcium by Particle Engineering Through Spherical Crystalisation," Research Journal of Pharmaceutical, Biological and Chemical Sciences, Jul.-Sep. 2013, vol. 4, Issue 3, pp. 1460-1468.

Kumar, N. et al., "Atorvastatin calcium encapsulated eudragit nanoparticles with enhanced oral bioavailability, safety and efficacy profile," Pharmaceutical Development and Technology, Mar. 2017;22(2):156-167. doi: 10.3109/10837450.2015.1108983. Epub Nov. 11, 2015.

Lennernas, H., "Clinical Pharmacokinetics of Atorvastatin," Clin Pharmacokinet 2003; 42(13):1141-1160.

McShane, M. et al., "An Oral, Rising, Multiple-Dose Tolerance, Pharmacokinetic, and Pharmacodynamic Study of Gemcabene in Healthy Volunteers," Gemphire Therapeutics Inc., Poster, ATVB May 2016, Nashville, TN, Abstract No. 482 Presentation No. 427, 1 page.

Mudie, D. M. et al., "Physiological Parameters for Oral Delivery and In vitro Testing," Mol Pharm. Oct. 4, 2010; 7(5): 1388-1405. doi:10.1021/mp100149j.

Narayanan, V. S. et al., "Design and evaluation of bi-layer drug delivery system of atorvastatin and glipizide," Int. J. Chem. Sci.: 7(3), 2009, 1802-1816.

Pang, K. S., "Modeling of intestinal drug absorption: roles of transporters and metabolic enzymes (for the Gillette review series)," Drug Metabolism and Disposition, vol. 31, No. 12, 2003, pp. 1507-1519.

Pasanen, M. K. et al., "Different Effects of SLCO1B1 Polymorphism on the Pharmacokinetics of Atorvastatin and Rosuvastatin," Clinical Pharmacology & Therapeutics, vol. 82, No. 6, Dec. 2007, pp. 726-733.

Prueksaritanont, T. et al., "Glucuronidation of Statins in Animals and Humans: A Novel Mechanism of Statin Lactonization," Drug Metabolism and Disposition May 2002, 30(5):505-512; DOI: https://doi.org/10.1124/dmd.30.5.505.

Shanmukaraj, D. et al., "Boron Esters as Tunable Anion Carriers for Non-Aqueous Batteries Electrochemistry," J. Am. Chem. Soc. 2010, 132(9):3055-3062.

Skottheim, I. B. et al., "Atorvastatin Metabolite Measurements as a Diagnostic Tool for Statin-Induced Myopathy," Mol. Diagn. Ther. 2011: 15(4):221-227.

Srivastava, R. A. K. et al., "Gemcabene, a first-in-class lipid-lowering agent in late-stage development, down-regulates acute-phase C-reactive protein via C/EBP-σ-mediated transcriptional mechanism," Molecular and Cellular Biochemistry, https://doi.org/10.1007/s11010-018-3353-5, published online: Apr. 11, 2018, 17 pages.

Taylor, E. P., "30. Synthetic Neuromuscular Blocking Agents. Part II. Bis(quaternary Ammonium Salts) derived from Laudanosine," J. Chem. Soc., 1952, 0, 142-145.

Vitthal, K. V. et al., "Melt extrusion based solid dispersions for enhanced solubility and physical stability of atorvastatin calcium," International Journal of Biopharmaceutics, 2016; 7(1): 35-47.

Wu, X. et al., "Atorvastatin transport in the Caco-2 cell model: contributions of P-glycoprotein and proton-monocarboxylic acid co-transporter," Pharmaceutical Research, Feb. 2000, vol. 17, No. 2, pp. 209-215.

Zhang, T., "Physiologically based pharmacokinetic modeling of disposition and drug-drug interactions for atorvastatin and its metabolites," European Journal of Pharmaceutical Sciences 77 (2015) 216-229.

International Search Report and Written Opinion for International Application No. PCT/US2018/028113, dated Jun. 21, 2018, 9 pages.

Fallingborg, J. et al., "pH-Profile and regional transit times of the normal gut measured by a radiotelemetry device," Aliment Pharmacol Ther., Dec. 1989, 3(6)605-613.

Kantola, T. et al., "Effect of itraconazole on the pharmacokinetics of atorvastatin," Clin. Pharmacol. Ther., 1998, 64:58-65.

Levy, G., "Effect of Particle Size on Dissolution and Gastrointestinal Absorption Rates of Pharmaceuticals," American Journal of Pharmacy and the Sciences Supporting Public Health, 135:78-92 (Mar. 1963).

* cited by examiner

PROCESSES AND INTERMEDIATES FOR PREPARING ALPHA,OMEGA-DICARBOXYLIC ACID-TERMINATED DIALKANE ETHERS

CROSS-REFERENCE TO RELATED APPLICATION

This application claims the benefit of U.S. Provisional Application Ser. No. 62/079,894, filed Nov. 14, 2014, the disclosure of which is hereby incorporated by reference in its entirety.

BACKGROUND OF THE INVENTION

α,ω-Dicarboxylic acid-terminated dialkane ethers have activity in lowering several plasma lipids, including Lp(a), triglycerides, VLDL-cholesterol, and LDL-cholesterol, both in animals and in humans. See U.S. Pub. No. 2010/0256209. The compounds also are known to increase insulin sensitivity. See U.S. Pub. No. 2010/0256209. In particular, 6,6'-oxy-bis(2,2-dimethyl-4-hexanoic acid) (also known as 6-(5-carboxy-5-methyl-hexyloxy)-2,2-dimethylhexanoic acid), whose USAN name is gemcabene, and its calcium salt (gemcabene calcium) have been intensively studied in multiple clinical trials as a lipid lowering agent for the treatment of patients with low high-density lipoprotein (HDL) and high low density lipoprotein (LDL). See Bays, H. E., et al., Amer. J. Cardiology, 2003, 92, 538-543. Gemcabene has been clinically tested as an anti-hypertensive and anti-diabetic agent in addition to the lipid lowering activity.

A synthetic method for the preparation of 6,6'-oxybis(2,2-dimethyl-4-hexanoic acid) and other α,ω-dicarboxylic acid-terminated dialkane ethers is described by Bisgaier, C. L. et al. in U.S. Pat. No. 5,648,387, which is incorporated herein by reference in its entirety. In addition, preparation and characterization of alcohol and water solvates of 6,6'-oxybis(2,2-dimethyl-4-hexanoic acid) calcium (gemcabene calcium), for the treatment of dyslipidemia, vascular disease, and diabetes are disclosed in U.S. Pat. No. 6,861,555, which is incorporated herein by reference in its entirety. Zhang, Y et al. also report a small scale synthesis of C-14- and tritiated-gemcabene congeners in J Label Compd Radiopharm 2007, 50, 602-604.

The previously disclosed syntheses raise a number of safety and environmental concerns when replicated on a scale larger than 1 kg. Thus, a need remains for safe and environmentally friendly processes for preparing α,ω-dicarboxylic acid-terminated dialkane ethers on a large scale.

SUMMARY OF THE INVENTION

These and other needs are met by the current disclosure, which provides general and industrially-scalable methods for the preparation of α,ω-dicarboxylic acid-terminated dialkane ethers and salts thereof.

The present disclosure provides a process for the preparation of compounds of formula (III),

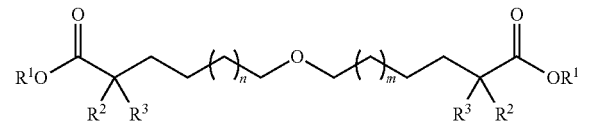

compounds of formula (V),

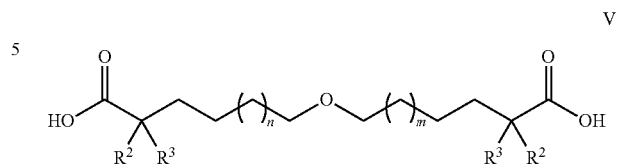

and corresponding salts of formula (IV):

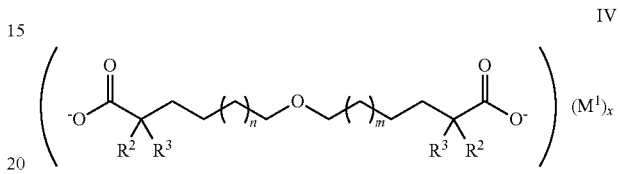

wherein $M^1$ is an alkaline earth metal or alkali metal.

The compounds made by the methods and processes of the invention are particularly useful for administration in humans and animals.

One aspect of the invention is a process for preparing a compound of formula (III):

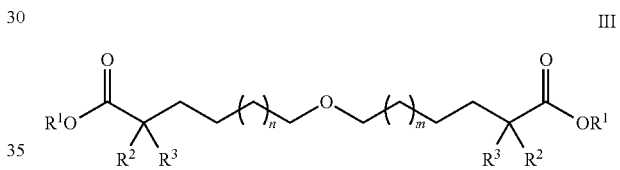

wherein:
 $R^1$ is alkyl;
 $R^2$ and $R^3$ are each independently alkyl, cycloalkyl, cycloalkylalkyl, heterocycloalkyl, heterocycloalkylalkyl, aryl, arylalkyl, heteroaryl, or heteroarylalkyl; and
 n and m are each independently 0-4;
comprising:
 (a) reacting a solution comprising a substituted acetic acid ester of formula (I):

with a deprotonating reagent to produce an intermediate of formula (Ia):

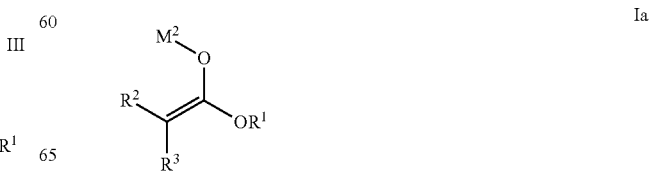

wherein $M^2$ is Li or Zn; and (b) reacting the intermediate of formula (Ia) with a solution comprising a α,ω-halo-terminated dialkane ether of formula (II):

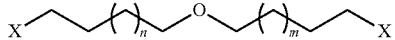

wherein X is a halogen;
to produce a compound of formula (III).

A further aspect of the invention is the process for preparing a compound of formula (III):

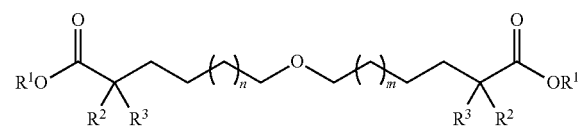

wherein:
R¹ is alkyl;
R² and R³ are each independently R² and R³ are each independently alkyl, cycloalkyl, cycloalkylalkyl, heterocycloalkyl, heterocycloalkylalkyl, aryl, arylalkyl, heteroaryl, or heteroarylalkyl; and
n and m are each independently 0-4;
comprising:
(a) reacting a solution comprising an α-bromo-acetic acid ester of formula (IX):

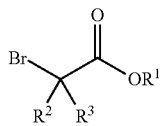

with a metal, until the metal is essentially dissolved;
(b) reacting the solution of step (a) with a solution comprising a α,ω-halo-terminated dialkane ether of formula (II):

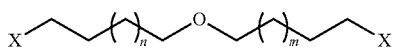

wherein X is halo;
to produce a compound of formula (III).
In other aspects, the compound of formula (III) is hydrolyzed to produce a compound of formula (V).

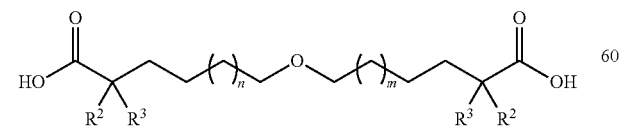

In some aspects, the compound of formula (V) is 6,6'-oxy-bis(2,2-dimethyl-4-hexanoic acid). In other aspects, the salt of formula (IV) is the calcium salt of 6,6'-oxy-bis(2,2-dimethyl-4-hexanoic acid).

In some aspects, the compound of formula (III) is a compound of formula (48).

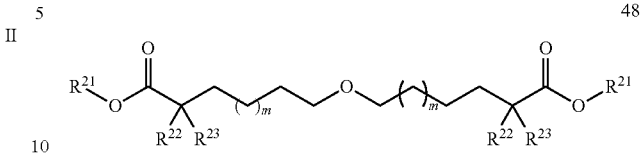

In some aspects, the compound of formula (V) is a compound of formula (49).

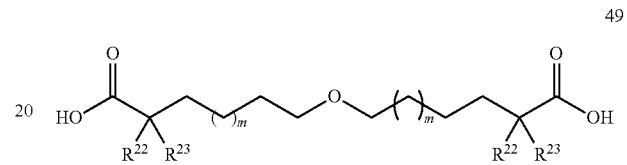

In some aspects, the salts of formula (IV) are salts of formula (50).

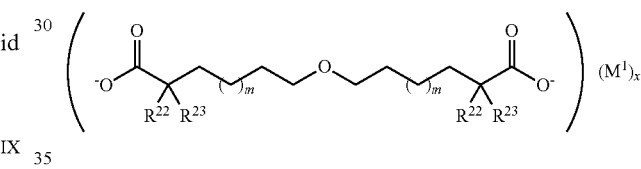

A further aspect discloses a process for preparing a compound of formula (48):

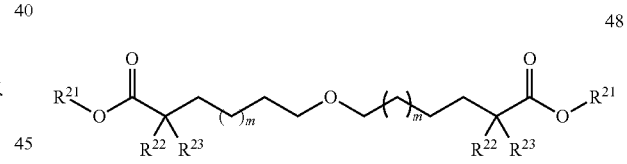

wherein:
R²¹ is alkyl;
R²² and R²³ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a first solution of a compound of formula (46):

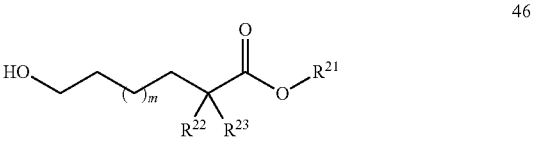

with a halogen source to produce an intermediate of formula (47):

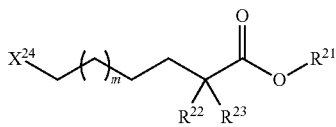

47 wherein $X^{24}$ is F, Cl, or I and where $R^{21}$ is alkyl;

(b) reacting a second solution of the compound of formula (46) with the intermediate of formula (47) in the presence of base to form a compound of formula (48).

In some embodiments, step (a) is in the presence of triphenylphosphine.

In one embodiment, the first compound of formula (46) and the second compound of formula (46) have identical substituents $R^{21}$, $R^{22}$ and $R^{23}$, and m is the same. In another embodiment, they are different.

In other aspects, the compound of formula (48) is hydrolyzed to produce a compound of formula (49).

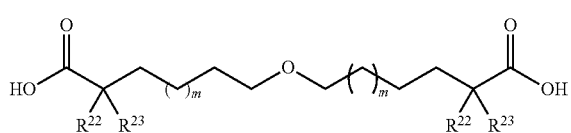

49

In some aspects, the compound of formula (49) is 6,6'-oxy-bis(2,2-dimethyl-4-hexanoic acid). In other aspects, the compound of formula (50) is the calcium salt of 6,6'-oxy-bis(2,2-dimethyl-4-hexanoic acid).

In a further aspect, a compound of formula (48):

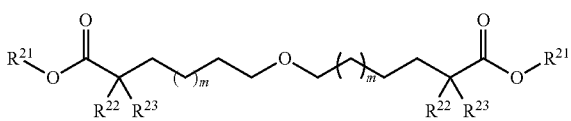

48 wherein:
R$^{21}$ is alkyl;
R$^{22}$ and R$^{23}$ are each independently alkyl, cycloalkyl, cycloalkylalkyl, heterocycloalkyl, heterocycloalkylalkyl, arylalkyl, heteroaryl, or heteroarylalkyl; and
m is 0-4;

comprising:
(a) reacting a solution of a cyclic lactone of formula (41):

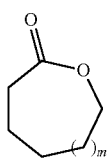

41 with a deprotonating reagent to produce an intermediate of formula (41a):

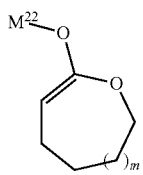

41a wherein $M^{22}$ is Li or Zn;
(b) reacting the intermediate of formula (41a) with a solution of an alkylhalide of formula (42):

$$R^{22}.X^{22} \qquad 42$$

wherein $X^{22}$ is halo;
to produce a compound of formula (43):

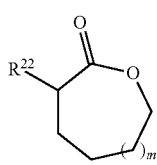

43

(c) reacting the solution of a compound of formula (43) with a deprotonating reagent to produce an intermediate of formula (43a):

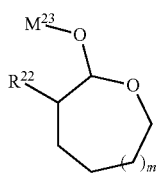

43a wherein $M^{23}$ is Li or Zn;
(d) reacting the intermediate of formula (43a) with a solution of an alkylhalide of formula (44):

$$R^{23}.X^{23} \qquad 44$$

wherein $X^{23}$ is halo;
to produce a compound of formula (45):

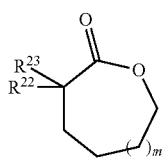

45

(e) reacting the solution of a compound of formula (45) with potassium tert-butoxide to produce an intermediate of formula (46):

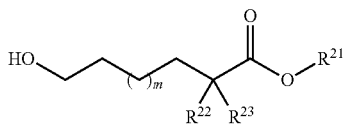

46

(f) reacting the solution of a compound of formula (46) with a halogen source in the presence of triphenylphosphine to produce an intermediate of formula (47):

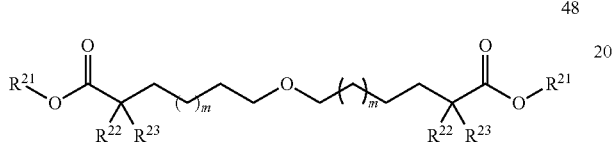

wherein $X^{24}$ is F, Cl, or I;

(g) reacting the solution of a compound of formula (46) with the intermediate of formula (47) in the presence of base to form a compound of formula (48):

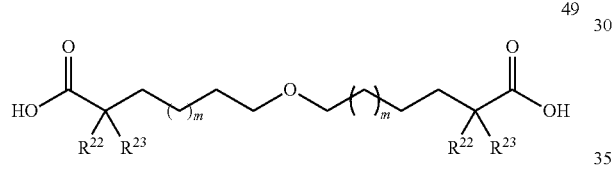

(h) reacting the solution of a compound of formula (48) with dilute acid to form (49).

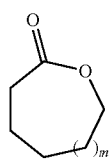

A further aspect is a process for preparing a compound of formula (45):

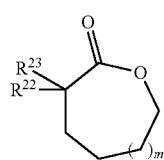

wherein:
R$^{22}$ and R$^{23}$ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a solution of a cyclic lactone of formula (41):

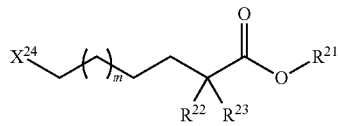

with a deprotonating reagent to produce an intermediate of formula (41a):

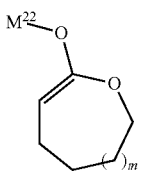

wherein $M^{22}$ is Li or Zn;
(b) reacting the intermediate of formula (41a) with a solution of an alkylhalide of formula (42):

$$R^{22}.X^{22} \qquad 42$$

wherein $X^{22}$ is halo;
to produce a compound of formula (43):

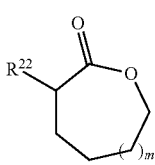

(c) reacting the solution of a compound of formula (43) with a deprotonating reagent to produce an intermediate of formula (43a):

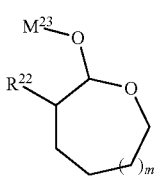

wherein $M^{23}$ is Li or Zn;
(d) reacting the intermediate of formula (43a) with a solution of an alkylhalide of formula (44):

$$R^{23}.X^{23} \qquad 44$$

wherein $X^{23}$ is halo;
to produce a compound of formula (45).

DETAILED DESCRIPTION OF THE INVENTION

Abbreviations and Definitions

The following abbreviations and terms have the indicated meanings throughout:

| Abbreviation | Meaning |
| --- | --- |
| ° C. | Degrees Celsius |
| DMF | Dimethylformamide |
| DMSO | Dimethyl Sulfoxide |
| Et | Ethyl |
| Eq | Equivalent |
| HDL | High-Density Lipoprotein |
| Hr | Hour |
| LDA | Lithium Diisopropylamide |
| LDL | Low-Densit Lipoprotein |

| Abbreviation | Meaning |
| --- | --- |
| Lp (a) | Lipoprotein (a) |
| M | Molar |
| Min | Minute |
| RT | Room Temperature |
| VLDL | Very Low-Density Lipoprotein |

The symbol "—" means a single bond, and "═" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

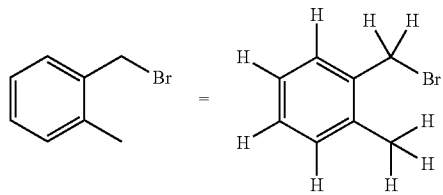

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylsilyl" means an alkyl group substituted with at least one silyl group, as defined herein.

"Amino" means —NH$_2$.

"Aminoalkyl" means an alkyl group substituted with at least one, specifically one, two or three, amino groups.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Cycloalkyl" means a monocyclic or fused bicyclic, saturated or partially unsaturated (but not aromatic), monovalent hydrocarbon radical of three to ten carbon ring atoms. Fused bicyclic hydrocarbon radical includes bridged ring systems. Unless stated otherwise, the valency of the group may be located on any atom of any ring within the radical, valency rules permitting. One or two ring carbon atoms may be replaced by a —C(O)—, —C(S)—, or —C(═NH)— group. More specifically, the term cycloalkyl includes, but is not limited to, cyclopropyl, cyclobutyl, cyclopentyl, cyclohexyl, cyclohexyl, or cyclohex-3-enyl, and the like.

"Cycloalkylalkyl" means an alkyl group substituted with at least one, specifically one or two, cycloalkyl group(s) as defined herein.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Halo" or "halogen" refers to fluorine, chlorine, bromine, or iodine.

"Haloalkyl" mean an alkyl group substituted with one or more halogens, specifically one to five halo atoms, e.g., trifluoromethyl, 2-chloroethyl, and 2,2-difluoroethyl, and the like.

"Heteroaryl" means a monocyclic, fused bicyclic, or fused tricyclic, monovalent radical of 5 to 14 ring atoms containing one or more, specifically one, two, three, or four ring heteroatoms independently selected from —O—, —S(O)$_N$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(═NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. When the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridiN-3-yl, phthalaziN-3-yl, phthalaziN-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroarylalkyl" means an alkyl group, as defined herein, substituted with at least one, specifically one or two heteroaryl group(s), as defined herein.

"Heterocycloalkyl" means a saturated or partially unsaturated (but not aromatic) monovalent monocyclic group of 3 to 8 ring atoms or a saturated or partially unsaturated (but not aromatic) monovalent fused bicyclic group of 5 to 12 ring atoms in which one or more, specifically one, two, three, or four ring heteroatoms independently selected from O, S(O)$_n$ (n is 0, 1, or 2), N, N(R$_y$) (where R$_y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(═NH)— group. Fused bicyclic radical includes bridged ring systems. Unless otherwise stated, the valency of the group may be located on any atom of any ring within the radical, valency rules permitting. When the point of valency is located on a nitrogen atom, $R^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

As used herein, the term "silyl" includes tri-lower alkylsilyl groups such as a trimethylsilyl group, a triethylsilyl group, an isopropyldimethylsilyl group, a t-butyldimethylsilyl group, a methyldiisopropylsilyl group, a methyl di-t-butylsilyl group and a triisopropylsilyl group; tri-lower alkylsilyl groups substituted with one or two aryl groups such as a diphenylmethylsilyl group, a butyldiphenylbutylsilyl group, a diphenylisopropylsilyl group and a phenyldiisopropylsilyl group. Preferably the silyl group is a trimethylsilyl group, a triethylsilyl group, a triisopropylsilyl group, a t-butyldimethylsilyl group or a t-butyldiphenylsilyl group, more preferably a trimethylsilyl group.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-8}$ alkyl," optional substitution may occur on both the "$C_{1-8}$ alkyl" portion and the "aryl" portion of the molecule may or may not be substituted. A list of exemplary optional substitutions is presented below in the definition of "substituted."

"Optionally substituted alkyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$— (where $R^c$ is hydrogen, alkyl, optionally substituted alkenyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, alkyl, optionally substituted alkenyl, hydroxy, alkoxy, alkenyloxy, or cyanoalkyl).

"Optionally substituted amino" refers to the group —N(H)R or —N(R)R where each R is independently selected from the group: optionally substituted alkyl, optionally substituted alkoxy, optionally substituted aryl, optionally substituted heterocycloalkyl, optionally substituted heteroaryl, acyl, carboxy, alkoxycarbonyl, —$S(O)_2$-(optionally substituted alkyl), —$S(O)_2$-optionally substituted aryl), —$S(O)_2$-(optionally substituted heterocycloalkyl), —$S(O)_2$-(optionally substituted heteroaryl), and —$S(O)_2$-(optionally substituted heteroaryl). For example, "optionally substituted amino" includes diethylamino, methylsulfonylamino, and furanyl-oxy-sulfonamino.

"Optionally substituted aminoalkyl" means an alkyl group, as defined herein, substituted with at least one, specifically one or two, optionally substituted amino group(s), as defined herein.

"Optionally substituted aryl" means an aryl group, as defined herein, optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo.

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups independently selected from acyl, acyloxy, acylamino, optionally substituted alkyl, optionally substituted alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, and cyano. Within the above optional substituents on "cycloalkyl", the alkyl and alkenyl, either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, and dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo.

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or aryl is pentafluorophenyl. Within the optional substituents on "heterocycloalkyl", the alkyl and alkenyl, either alone or as part of another group (including, for example, the alkyl in alkoxycarbonyl), are independently optionally substituted with one, two, three, four, or five halo.

"Optionally substituted heterocycloalkylalkyl" means an alkyl group, as defined herein, substituted with at least one, specifically one or two, optionally substituted heterocycloalkyl group(s) as defined herein.

As used herein, "6,6'-oxybis(2,2-dimethyl-4-hexanoic acid)" and "6-(5-carboxy-5-methyl-hexyloxy)-2,2-dimethylhexanoic acid" refer to the same chemical structure (3), as depicted below, and therefore they may be used interchangeably.

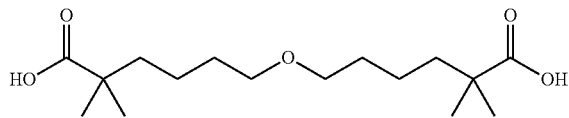

3

More specifically, it is to be understood that for the purposes of the present invention, the terms "6,6'-oxybis(2,2-dimethyl-4-hexanoic acid) calcium," "6-(5-carboxy-5-methyl-hexyloxy)-2,2-dimethylhexanoic acid monocalcium salt," "CI-1027," "gemcabene" (USAN nomenclature), and "compound 3" name the same chemical structure. Therefore, it is to be understood that the names may also be used interchangeably.

EMBODIMENTS

In one aspect, compounds of formula (III) and corresponding salts are prepared according to Scheme 1.

Scheme 1

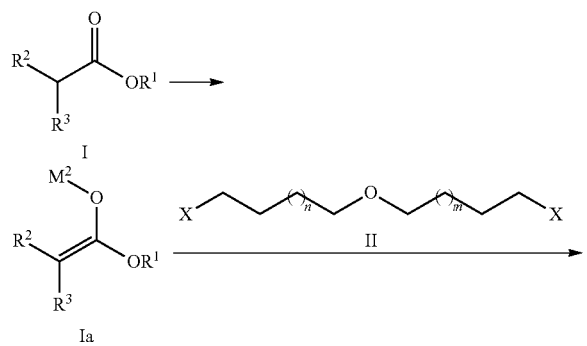

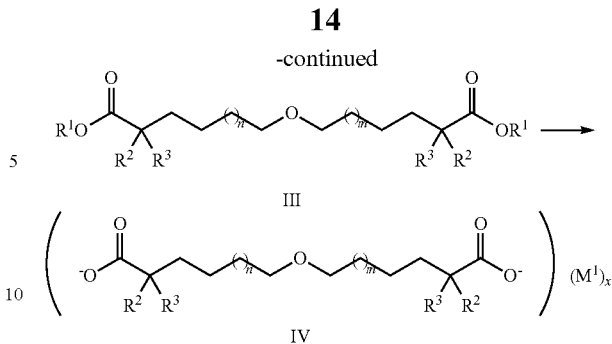

In Scheme 1, an ester of formula (I) is reacted with a deprotonating reagent to produce an intermediate of formula (Ia).

In other aspects, the compound of formula (III) is hydrolyzed to produce a compound of formula (V).

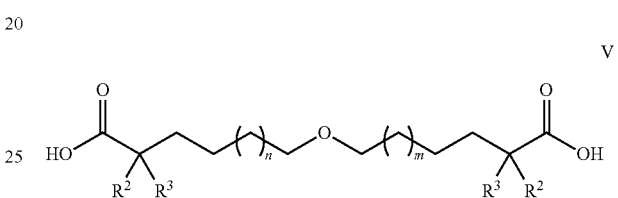

Esters of formula (I) are commercially available (Aldrich Chemical Co., Milwaukee, Wis.). In some embodiments, an ester of formula (I) is prepared by well-known synthetic methods, for example, via esterification of isobutyric acid (commercially available, Aldrich Chemical Co., Milwaukee, Wis.).

In some embodiments, $R^1$ is alkyl. More particularly, $R^1$ is $C_1$-$C_8$ alkyl. In other embodiments, $R^1$ is methyl or ethyl. More particularly, $R^1$ is ethyl.

In some embodiments, $R^2$ and $R^3$ are each independently selected from alkyl, cycloalkyl, cycloalkylalkyl, heterocycloalkyl, heterocycloalkylalkyl, aryl, arylalkyl, heteroaryl, or heteroarylalkyl. In some embodiments, $R^2$ and $R^3$ are selected from $C_1$-$C_8$ alkyl, $C_3$-$C_6$ cycloalkyl, heterocycloalkyl, aryl, or heteroaryl. In one embodiment, $R^2$ and $R^3$ are both $C_1$-$C_8$ alkyl. More particularly, $R^2$ and $R^3$ are both methyl. In other embodiments, $R^2$ and $R^3$ are both phenyl. In other embodiments, $R^2$ is methyl and $R^3$ is o-tolyl. In one embodiment, $R^2$ and $R^3$ are the same. In other embodiments, $R^2$ and $R^3$ are different.

In some embodiments, $M^1$ is an alkaline earth metal or alkali metal. More particularly, $M^1$ is Ca or K.

In one embodiment, x is 1 or 2.

In some embodiments, n and m are each independently 0-4. In one embodiment, $R^2$ and $R^3$ are the same. In other embodiments, $R^2$ and $R^3$ are different. In one embodiment, n and m are independently 1 or 2. In another embodiment, n is 0 and m is 1. In another embodiment, n is 1 and m is 2. In another embodiment, n is 2 and m is 3. In another embodiment, n is 3 and m is 4. In another embodiment, both n and m are 0. In another embodiment, both n and m are 1. In another embodiment, both n and m are 2. In another embodiment, both n and m are 3. In another embodiment, both n and m are 4.

In some embodiments, the deprotonating reagent is an organometallic reagent. More particularly, the organometallic reagent is $(R)_p$-$M^2$, wherein $M^2$ is a metal, and p is the metal's valency value (1 for Li, 2 for Zn, etc.). $M^2$ is selected from, for example, Zn, Na, Li, and Grignard reagents —Mg-Halo. More particularly, Halo is selected from the group consisting of iodo, bromo, and chloro.

In some embodiments, R is optionally substituted alkyl, optionally substituted cycloalkyl, optionally substituted cycloalkylalkyl, optionally substituted heterocycloalkyl, optionally substituted heterocycloalkylalkyl, optionally substituted aryl, optionally substituted arylalkyl, optionally substituted heteroaryl, optionally substituted heteroarylalkyl, optionally substituted amino, optionally substituted alkylamino, optionally substituted aminoalkyl, optionally substituted dialkylamino, or optionally substituted alkylsilyl.

In one embodiment, the deprotonating agent is an alkylmetal base. The alkylmetal base may be used a ratio from 0.5 eq to a slight equimolar excess relative to the bis-halide of formula (2).

Organometallic reagents such as $(R)_p$-$M^2$ are commercially available (Aldrich Chemical Co., Milwaukee, Wis., FMC Lithium Lithco Product List, etc.). In some embodiments, organometallic reagents can be prepared by well-known methods (Kharasch et al., *Grignard Reactions of Non-Metallic Substances*; Prentice-Hall, Englewood Cliffs, N.J., pp. 138-528 (1954) and Hartley; Patai, *The Chemistry of the Metal-Carbon Bond*, Vol. 4, Wiley: New York, pp. 159-306 and pp. 162-175 (1989)).

In some embodiments, the reaction of an $(R)_p$-$M^2$ organometallic reagent with the ester of formula (I) to provide metal enolates, such as lithioenolates, can be performed using the general procedures described in March, J. *Advanced Organic Chemistry; Reactions Mechanisms, and Structure*, 4th ed., 1992, pp. 920-929 and Eicher, Patai, *The Chemistry of the Carbonyl Group*, pt. 1, pp. 621-693; Wiley: New York, (1966). In other embodiments, the synthetic procedure described in Comins, D. et al., *Tetrahedron Lett.* 1981, 22, 1085, can be used.

In one embodiment, the reaction is performed by adding an organic solution of $(R)_p$-$M^2$ (approximately 0.5 to approximately 1.5 eq) to a stirred, cooled (approximately 0° C. to approximately −80° C.) solution comprising an ester of formula (I). In some embodiments, this step is performed under an inert atmosphere, such as nitrogen or argon gas. More particularly, $(R)_p$-$M^2$ is added at such a rate that the temperature of the reaction mixture remains within approximately one to five degrees of the initial temperature of the ester of formula (I).

Non-limiting examples of suitable organometallic reagents include:
i. alkylmetal bases, such as methyllithium, n-butyllithium, tert-butyllithium, sec-butyllithium, phenyllithium, phenyl sodium, phenyl potassium, n-hexyllithium, n-heptyllithium, and n-octyllithium;
ii. metal amide bases, such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide;
iii. hydride bases, such as sodium hydride and potassium hydride;
iv. metal amide bases, such as lithium diisopropylamide; and
v. non-pyrophoric lithium derivatives, such as n-hexyllithium, n-heptyllithium, and n-octyllithium.

More particularly, the organometallic reagent is selected from n-butyllithium, n-hexyllithium, n-heptyllithium, and n-octyllithium in hexane solutions of various molar concentrations, but no less than 2M, commercially available in bulk quantities from commercial suppliers, for example, Sigma-Aldrich FMC Lithium Lithco Product List.

In some embodiments, the process is used for large scale production of compounds of formula (III) or formula (V) and corresponding salts of formula (IV). In one embodiment, the organometallic reagent in the large scale process is selected from n-hexyllithium, n-heptyllithium, and n-octyllithium.

Suitable organic solvents for the reaction of the ester of formula (I) with the deprotonating agent include, but are not limited to, dichloromethane, diethyl ether, tetrahydrofuran, 2-methyltetrahydrofuran, dimethylformamide, dimethyl sulfoxide, benzene, toluene, xylene, hydrocarbon solvents (such as pentane, hexane, and heptane), and mixtures thereof.

More particularly, in some embodiments, the organic solvent or mixture of solvents is chosen in order to influence favorably to optimize conversion to the lithioenolate by modulating the concentration of the lithium aggregate [(RLi)x(—LiX)y] formation, as described in Gossage, R. A. et al., *Angew. Chem. Int. Ed.* 2005, 44, 1448-1454. More particularly, the solvent is selected from tetrahydrofuran, 2-methyltetrahydrofuran, and mixtures thereof. In one embodiment, the lithium reagent/solvent system in the large scale process is n-hexyllithium and hexane (See Stouffer et al., U.S. Pat. No. 6,239,300).

In some embodiments, the reaction of the ester of formula (I) with the deprotonating agent is performed in the presence of additives. Additives may be added, for example, to improve the selectivity of lithiation by breaking up the lithium oligomers and stabilize the lithiated intermediate. Particularly, solvents such as DMSO or chelating additives such as diamines, tetraalkylureas, and cyclic alkylureas, are used. Non-limiting examples of such chelating additives include, but are not limited to, 1,3-dimethyl-3,4,5,6-tetrahydro-2(1H)-pyrimidinone (DMPU), hexamethylphosphoramide (HMPA), N,N,N',N'-tetramethylethylenediamine (TMEDA), and bis(N,N'-dimethylaminoethyl)ether. Exemplary procedures are described in Wu, J.-P. et al., *Tetrahedron Letters* 2009, 50, 5667-5669 (large scale lithiation using LDA and bis(N,N'-dimethylaminoethyl)ether)), van der Veen, R. H. et al., *J. Org. Chem.* 1985, 50, 342-346 (for the LDA-HMPT reaction tandem), Dehmlow, E. V. et al., *Synthetic Communications* 1998, 18, 487-494 ("Phase Transfer Catalytic Preparation of the Dipolar Aprotic Solvents DMI and DMPU"), Beck, A. K. et al., "N,N'-Dimethylpropyleneurea", in Encyclopedia of Reagents for Organic Synthesis., New York: John Wiley & Sons, 2001, Mukhopadhyay, T. et al., *Helvetica Chimica Acta* 1982, 65, 385-391 ("Substitution of HMPT by the Cyclic Urea DMPU as a Cosolvent for highly Reactive Nucleophiles and Bases").

In some embodiments, the reaction of the ester of formula (I) with the deprotonating agent can be performed by adding a solution comprising an ester of formula (I) to a stirred, cooled organic solution (approximately 20° C. to approximately −80° C.) of $(R)_p$-$M^2$ (approximately 0.5 to approximately 1.5 eq). In some embodiments, the reaction is performed under an inert atmosphere, such as nitrogen or argon gas. Preferably, the solution comprising an ester of formula (I) is added at such a rate that the temperature of the reaction mixture remains within approximately one to five degrees of the initial temperature of the ester solution. An exemplary procedure, which describes large scale metallations using n-butyllithium at low temperatures is published in Ashwood, M. S. et al., *Organic Process Research & Development* 2004, 8, 192-200.

In one embodiment, the organic solvent is tetrahydrofuran, 2-methyltetrahydrofuran, or mixtures thereof.

In another embodiment, the metallation reagent is selected from LDA, n-hexyllithium and n-heptyllithium.

Exemplary procedures in which the metallation agent is n-hexyllithium are described in Baenziger, M. et al. *Org. Proc. Res. Dev.* 1997, 1, 395, Bishop, B. et al., US Pub no. 2006/0149069 A1 (WO2004078109), and Li, G. et al., US Pub. No. 2007/0105857 (WO2007044490). Exemplary procedures in which metallation reagents used are selected from n-hexyllithium and n-heptyllithium are found in Harmata, M. et al., *Chem. Commun.* 2003, 2492-2493. See also Lochmann, L. et al., U.S. Pat. No. 3,971,816; Lipton, M. F. et al., *Organic Process Research & Development* 2003, 7, 385-392, which describes preparations of lithioesters.

In all examples, the progress of the reaction can be followed using an appropriate analytical method, such as thin-layer chromatography or high-performance-liquid chromatography.

In some embodiments, after the deprotonation step, the α,ω-halo-terminated dialkane ether of formula (II) in an appropriate solvent is added to the intermediate of formula (Ia) to provide a compound of formula (III). In some embodiments, the dialkane ether of formula (II) is added with cooling and stirring. More particularly, the addition is performed at a rate such as the temperature variations are no more than five degrees of the initial temperature of the ester.

In some embodiments, the reaction mixture can be quenched with an aqueous solution (such as sodium chloride, ammonium chloride, etc.), and the product can be isolated by typical workup methods. Suitable solvents for solubilizing a compound of formula (III) include, but are not limited to, dichloromethane, diethyl ether, tetrahydrofuran, 2-methyltetrahydrofuran, benzene, toluene, xylene, hydrocarbon solvents (such as pentane, hexane, and heptane), and mixtures thereof.

In one embodiment, after the reaction is deemed substantially complete by using an appropriate analytical method, the reaction mixture containing the compound of formula (III) is hydrolyzed in the presence of an alkaline earth metal salt or base, or oxide, or alkali metal salt or base. The salt formation is accomplished by treating the compound of formula (III) with an oxide, base, or salt in refluxing alcohols for 2 to 96 hours. Typical examples include, but are not limited to, hydrolysis with $K_2CO_3$ in a refluxing mixture of DMSO and water. Further suitable procedures are referenced in Houben-Weyl, *Methoden der Organische Chemie*, Georg Thieme Verlag Stuttgart 1964, vol. XII/2, pp. 143-210 and 872-879, or Anderson, N. G., *Practical Process Research & Development*, Academic Press, London, 2000, pp. 93-94 and 181-182.

In yet another embodiment, the process comprises treating a solution of a compound of formula (III) in a water-miscible solvent with an aqueous solution of a base. More particularly, the water-miscible solvent is selected from DMF, DMSO, acetone, methanol, isopropyl alcohol, and ethanol.

In yet another embodiment, the process comprises treating a solution of the compound of formula (III) in a water-immiscible solvent with an aqueous solution of a base. More particularly, the water-immiscible solvent is selected from toluene, xylene, methyl ethyl ketone, and methyl isobutyl ketone.

In yet another embodiment, the process comprises treating a solution of the compound of formula (III) in a water-miscible solvent with an aqueous solution of calcium hydroxide or calcium oxide. More particularly, the water-miscible solvent is selected from DMF, DMSO, acetone, methanol, isopropyl alcohol, and ethanol.

In another embodiment, the process further comprises performing an aqueous work-up of the solution of step (b) in order to isolate an organic fraction of the compound of formula (III).

In another embodiment, the process further comprises the step of treating the crude compound of formula (III) with a hydroxide or oxide of an alkali or earth alkaline metal in a suitable solvent.

In another embodiment, the process further comprises the step of precipitating the salt of the α,ω-dicarboxylic acid-terminated dialkane ether of formula (IV) in the presence of an organic solvent.

In another embodiment, the process further comprises the step of removing the organic layer by evaporation to afford crude crystalline α,ω-dicarboxylic acid-terminated dialkane ether salt of formula (IV) as an alcohol solvate or hydrate.

In another embodiment, the process further comprises the step of adding one or more anti-solvents to the solid so that the salt of the α,ω-dicarboxylic acid-terminated dialkane ether of formula (IV) is insoluble.

In another embodiment, the process further comprises the step of humidifying the precipitate to obtain a crystalline salt of α,ω-dicarboxylic acid-terminated dialkane ether of formula (IV).

In a further embodiment, the process further comprises the preparation of a crystalline salt of a α,ω-dicarboxylic acid-terminated dialkane ether of formula (IV) at multi-kilogram scale, wherein the process comprises the steps of:
  (a) reacting a solution comprising a substituted acetic acid ester of formula (I) with a deprotonating reagent to produce an intermediate of formula (Ia);
  (b) reacting the intermediate of formula (Ia) with a solution comprising a α,ω-halo-terminated dialkane ether of formula (II);
  (c) performing an aqueous work-up of the solution of step (b) in order to isolate an organic solution of the compound of formula (III);
  (d) treating the crude compound of formula (III) of step (c) with a hydroxide or oxide of an alkali or earth alkaline metal in a suitable solvent;
  (e) precipitating the salt of the α,ω-dicarboxylic acid-terminated dialkane ether of formula (IV) in the presence of an organic solvent; or, alternatively, removing the organic layer by evaporation to afford crude crystalline α,ω-dicarboxylic acid-terminated dialkane ether salt of formula (IV) in the form of an alcohol solvate or hydrate;
  (f) adding one or more anti-solvents to the solid of step (e) in which the salt of the α,ω-dicarboxylic acid-terminated dialkane ether of formula (IV) is insoluble; and
  (g) humidifying the precipitate resultant from step (f) to obtain a crystalline salt of α,ω-dicarboxylic acid-terminated dialkane ether of formula (IV).

In some embodiments, the metal salt of an α,ω-dicarboxylic acid-terminated dialkane ether of formula (IV) is isolated in a specific and consistently reproducible polymorph.

In a further embodiment, the process further comprises the preparation of a α,ω-dicarboxylic acid-terminated dialkane ether, wherein the process comprises the steps of:
  (a) reacting a solution comprising a substituted acetic acid ester of formula (I) with a deprotonating reagent to produce an intermediate of formula (Ia);
  (b) reacting the intermediate of formula (Ia) with a solution comprising a α,ω-halo-terminated dialkane ether of formula (II);

(c) performing an aqueous work-up of the solution of step (b) in order to isolate an organic solution of the compound of formula (III); and
(d) treating the crude compound of formula (III) of step (c) with a hydroxide or oxide of an alkali or earth alkaline metal in a suitable solvent.

In a further embodiment, the process further comprises the preparation of a crystalline salt of a α,ω-dicarboxylic acid-terminated dialkane ether of formula (IV), wherein the process comprises the steps of:
(e) precipitating the salt of the α,ω-dicarboxylic acid-terminated dialkane ether of formula (IV) in the presence of an organic solvent; or, alternatively, removing the organic layer by evaporation to afford crude crystalline α,ω-dicarboxylic acid-terminated dialkane ether salt of formula (IV) in the form of an alcohol solvate or hydrate;
(f) adding one or more anti-solvents to the solid of step (e) in which the salt of the α,ω-dicarboxylic acid-terminated dialkane ether of formula (IV) is insoluble; and
(g) humidifying the precipitate resultant from step (f) to obtain a crystalline salt of α,ω-dicarboxylic acid-terminated dialkane ether of formula (IV).

In a particular embodiment, the invention provides a method for the preparation of crystalline 6,6'-oxybis(2,2-dimethyl-4-hexanoic acid) calcium of formula (VIII), wherein the process comprises the steps of:
(a) reacting a solution of ethyl isobutyrate of formula (IXa)

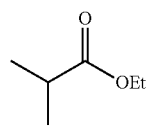

IXa with a deprotonating reagent to produce a compound of formula (X);

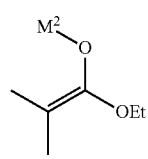

X (b) reacting the ethyl lithiobutyrate of step (a) with a solution of bis(4-chlorobutylether) of formula (XI);

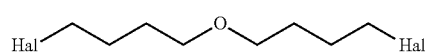

XI (c) performing an aqueous work-up of the solution of step (b) in order to isolate an organic solution of crude diethyl 6,6'-oxybis(2,2-dimethyl-4-hexanoate) of formula (3);

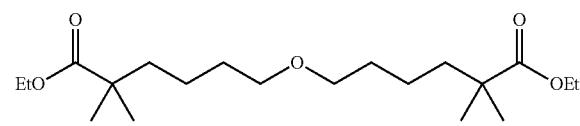

3

(d) treating the crude diethyl 6,6'-oxybis(2,2-dimethyl-4-hexanoate) of formula (3) of step (c) with a calcium hydroxide or calcium oxide of an alkali or earth alkaline metal in a suitable solvent;
(e) precipitating the 6,6'-oxybis(2,2-dimethyl-4-hexanoic acid) calcium of formula (4):

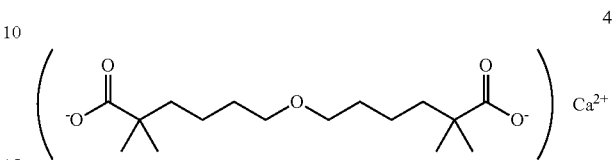

4 in the presence of an organic solvent, or, alternatively, removing the organic layer by evaporation to afford crude crystalline 6,6'-oxybis(2,2-dimethyl-4-hexanoic acid) salt of formula (4) as an alcohol solvate or hydrate;
(f) adding one or more anti-solvents to the solid of step (e) in which 6,6'-oxybis(2,2-dimethyl-4-hexanoic acid) calcium of formula (4) is insoluble; and
(g) humidifying the precipitate resultant from step (f) to obtain crystalline 6,6'-oxybis(2,2-dimethyl-4-hexanoic acid) calcium of formula (4).

In some embodiments, the 6,6'-oxybis(2,2-dimethyl-4-hexanoic acid) calcium of formula (4) is isolated in a specific and consistently reproducible polymorph.

In a further embodiment, compounds of formula (3) and corresponding salts (4) are prepared according to Scheme 2.

Scheme 2

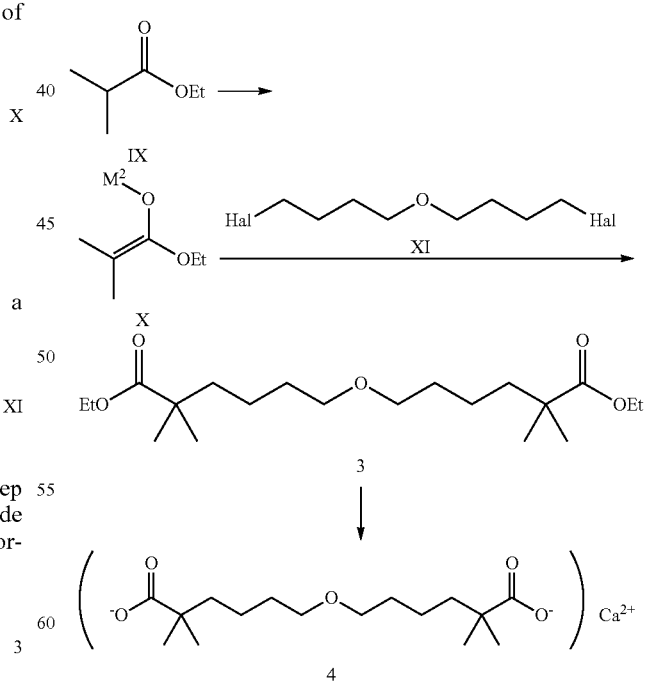

In a particular embodiment, the invention provides a method for the preparation of a α,ω-dicarboxylic acid-terminated dialkane ether, wherein the process comprises the steps of:

(a) reacting a solution of ethyl isobutyrate of formula (IX) with a deprotonating reagent;

(b) reacting the ethyl lithiobutyrate of step (a) with a solution of bis(4-chlorobutylether) of formula (XI);

(c) performing an aqueous work-up of the solution of step (b) in order to isolate an organic solution of crude diethyl 6,6'-oxybis(2,2-dimethyl-4-hexanoate) of formula (3);

(d) treating the crude diethyl 6,6'-oxybis(2,2-dimethyl-4-hexanoate) of formula (3) of step (c) with a calcium hydroxide or calcium oxide of an alkali or earth alkaline metal in a suitable solvent.

In a further embodiment, the process further comprises the preparation of 6,6'-oxybis(2,2-dimethyl-4-hexanoic acid) calcium of formula (4), wherein the process comprises the steps of:

(e) precipitating the 6,6'-oxybis(2,2-dimethyl-4-hexanoic acid) calcium of formula (4) in the presence of an organic solvent; or, alternatively, removing the organic layer by evaporation to afford crude crystalline 6,6'-oxybis(2,2-dimethyl-4-hexanoic acid) salt of formula (4) as an alcohol solvate or hydrate;

(f) adding one or more anti-solvents to the solid of step (e) in which 6,6'-oxybis(2,2-dimethyl-4-hexanoic acid) calcium of formula (4) is insoluble; and (g) humidifying the precipitate resultant from step (f) to obtain crystalline 6,6'-oxybis(2,2-dimethyl-4-hexanoic acid) calcium of formula (4).

In another aspect, compounds of formula (III) and corresponding salts may be prepared under certain conditions according to Scheme 3, which utilizes a Reformatsky reaction. In Scheme 2, an α-bromoacetic acid ester of formula (XV) is reacted with a bis(haloalkyl)ether of formula (II) and a metal to provide a compound of formula (III). Examples of Reformatsky reactions are described in Jun, I. *Molecules* 2012, 17, 14249-14259. Exemplary procedures of Reformatsky reactions are collected on-line, on the Organic Chemistry Portal at www.organic-chemistry.org/namedreactions/reformatsky-reaction.shtm (last visited Nov. 12, 2014).

Scheme 3

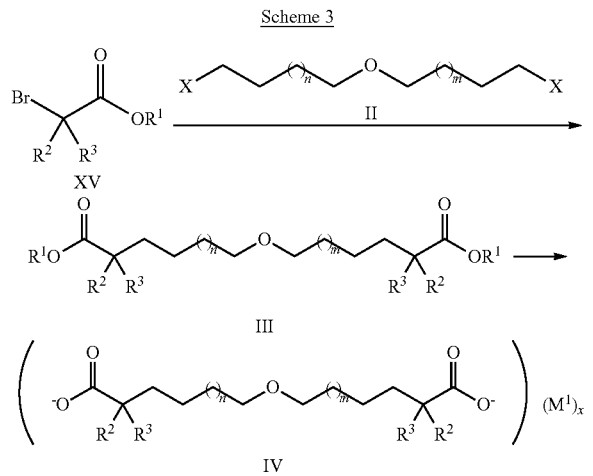

In other aspects, the compound of formula (III) is hydrolyzed to produce a compound of formula (V).

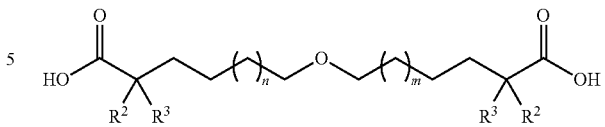

In some embodiments of formula (V), $R^1$ is alkyl. More particularly, $R^1$ is C1-C8 alkyl. In other embodiments, $R^1$ is methyl or ethyl. More particularly, $R^1$ is ethyl.

In some embodiments, $R^2$ and $R^3$ are each independently alkyl, cycloalkyl, cycloalkylalkyl, heterocycloalkyl, heterocycloalkylalkyl, aryl, arylalkyl, heteroaryl, or heteroarylalkyl. In some embodiments, $R^2$ and $R^3$ are selected from $C_1$-$C_8$ alkyl, $C_3$-$C_6$ cycloalkyl, heterocycloalkyl, aryl, or heteroaryl. In one embodiment, $R^2$ and $R^3$ are both $C_1$-$C_8$ alkyl. More particularly, $R^2$ and $R^3$ are both methyl. In other embodiments, $R^2$ and $R^3$ are both phenyl. In other embodiments, $R^2$ is methyl and $R^3$ is o-tolyl. In one embodiment, $R^2$ and $R^3$ are the same. In other embodiments, $R^2$ and $R^3$ are different.

In some embodiments, x is 1 or 2.

In some embodiments, n and m are each independently 0-4. In one embodiment, $R^2$ and $R^3$ are the same. In other embodiments, $R^2$ and $R^3$ are different. In one embodiment, n and m are independently 1 or 2. In another embodiment, n is 0 and m is 1. In another embodiment, n is 1 and m is 2. In another embodiment, n is 2 and m is 3. In another embodiment, n is 3 and m is 4. In another embodiment, both n and m are 0. In another embodiment, both n and m are 1. In another embodiment, both n and m are 2. In another embodiment, both n and m are 3. In another embodiment, both n and m are 4.

In some embodiments, $M^1$ is an alkaline earth metal or alkali metal. More particularly, $M^1$ is Ca or K.

In one embodiment, the reaction is performed in the presence of a metal selected from zinc, magnesium, manganese, and indium. More particularly, the reaction is performed in the presence of zinc.

In one embodiment, the reaction is performed using a solvent selected from toluene, xylene, ethers, tetrahydrofuran, diethyl ether, methyl t-butyl ether, and 2-methyltetrahydrofuran. In other embodiments, aqueous solutions of calcium or ammonium chloride can be optionally used, as described in Bieber, L. W., *J. Org. Chem.* 1997, 62, 9061-9064.

In some embodiments, initiators and/or catalysts are employed. Examples of initiators and catalysts include, but are not limited to, iodine (see Zitsman, J. et al. Tetrahedron Letters 1971, 44, 4201-4204, and Johnson, P. Y. et al., *J. Org. Chem.* 1973, 38, 2346-2350). For MCPBA and MMPP see Bieber, L. W. *J. Org. Chem.* 1997, 62, 9061-9064.

In one embodiment, the α-bromoester of formula (XV) is cooled to −20° C. to 0° C. In some embodiments, the reaction is performed in an inert atmosphere, such as nitrogen or argon gas.

In some embodiments, the α-bromoester of formula (XV) is further treated with approximately 1 to 2.5 eq of a metal, more particularly 1 eq, in a solvent. More particularly, the solvent is tetrahydrofuran, 2-methyltetrahydrofuran, or toluene.

In one example, the suspension is stirred until the metal is essentially dissolved.

In one embodiment, if necessary, a catalyst is added as a reaction initiator. The bis(halo)ether of formula (II) is then added at a flow rate that maintains the temperature between 0 and 10° C. during addition. Alternatively, the solution of the metallated α-bromoester of formula (XV) is added dropwise into the bis(halo)ether of formula (II) solution in an appropriate solvent.

The reaction mixture is then warmed to RT. If the reaction is not complete as determined by an appropriate analytical method the mixture is then heated at 40 to 60° C. for several hours, particularly 50° C. for 4 hours.

In some embodiments, the reaction mixture is kept under vigorous stirring for several hours or up to 2 days until the conversion to the desired product has ceased.

After the reaction is deemed substantially complete using an appropriate analytical method, the reaction mixture containing the compound of formula (III) may be subjected to workup and extraction in an organic solvent.

The crude product may be hydrolyzed in the presence of an alkaline earth metal salt or base, oxide, or alkali metal salt or base to yield the diacid of formula (IV), as described for the examples in Scheme 2.

In some embodiments, the process further comprises performing an aqueous work-up of the solution to isolate an organic fraction of the compound of formula (III).

In one embodiment, the process further comprises the step of treating the crude compound of formula (III) with a hydroxide or oxide of an alkali or earth alkaline metal in a suitable solvent.

In one embodiment, the process further comprises the step of precipitating the salt of the α,ω-dicarboxylic acid-terminated dialkane ether of formula (IV) in the presence of an organic solvent.

In another embodiment, the process further comprises the step of removing the organic layer by evaporation to afford crude crystalline α,ω-dicarboxylic acid-terminated dialkane ether salt of formula (IV) as an alcohol solvate or hydrate.

In one embodiment, the process further comprises the step of adding one or more anti-solvents to the solid so that the salt of the α,ω-dicarboxylic acid-terminated dialkane ether of formula (IV) is insoluble.

In one embodiment, the process further comprises the step of humidifying the precipitate to obtain a crystalline salt of a α,ω-dicarboxylic acid-terminated dialkane ether of formula (IV).

In some embodiments, the process is used for large scale production of compounds of formula (III) or formula (V) and corresponding salts of formula (IV).

In yet another embodiment, the process comprises treating a solution of a compound of formula (III) in a water-miscible solvent with an aqueous solution of a base. More particularly, the water-miscible solvent is selected from DMF, DMSO, acetone, methanol, isopropyl alcohol, and ethanol.

In yet another embodiment, the process comprises treating a solution of the compound of formula (III) in a water-immiscible solvent with an aqueous solution of a base. More particularly, the water-immiscible solvent is selected from toluene, xylene, methyl ethyl ketone, and methyl isobutyl ketone.

In yet another embodiment, the process comprises treating a solution of the compound of formula (III) in a water-miscible solvent with an aqueous solution of calcium hydroxide or calcium oxide. More particularly, the water-miscible solvent is selected from DMF, DMSO, acetone, methanol, isopropyl alcohol, and ethanol.

In yet another embodiment, the process comprises treating a solution of the compound of formula (III) in a water-immiscible solvent with an aqueous solution of calcium hydroxide or calcium oxide. More particularly, the water-immiscible solvent is selected from toluene, xylene, methyl ethyl ketone, and methyl isobutyl ketone.

In a particular embodiment, the process for preparing the salt of a compound of formula (III) comprises:
(a) reacting a solution comprising an α-bromo-acetic acid ester of formula (XV):

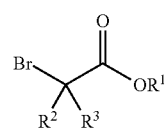

with a metal, until the metal is essentially dissolved;
(b) reacting the solution of step (a) with a solution comprising a α,ω-halo-terminated dialkane ether of formula (II)

wherein X is halo;
(c) performing an aqueous work-up of the solution of step (b) in order to isolate an organic fraction of the compound of formula (III);
(d) treating the crude compound of formula (III) of step (c) with a hydroxide or oxide of an alkali or earth alkaline metal in a suitable solvent;
(e) precipitating the salt of the α,ω-dicarboxylic acid-terminated dialkane ether of formula (IV) in the presence of an organic solvent; or, alternatively, removing the organic layer by evaporation to afford crude crystalline α,ω-dicarboxylic acid-terminated dialkane ether salt of formula (IV) as an alcohol solvate or hydrate;
(f) adding one or more anti-solvents to the solid of step (e) in which the salt of the α,ω-dicarboxylic acid-terminated dialkane ether of formula (IV) is insoluble; and
(g) humidifying the precipitate resultant from step (f) to obtain a crystalline salt of a α,ω-dicarboxylic acid-terminated dialkane ether of formula (IV).

In some embodiments, the α,ω-dicarboxylic acid-terminated dialkane ether of formula (IV) is isolated in a specific and consistently reproducible polymorph.

In a particular embodiment, the invention provides a method for the preparation of a α,ω-dicarboxylic acid-terminated dialkane ether, wherein the process comprises the steps of:
(a) reacting a solution comprising an α-bromo-acetic acid ester of formula (XV):

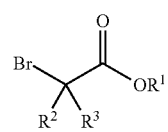

with a metal, until the metal is essentially dissolved;
(b) reacting the solution of step (a) with a solution comprising a α,ω-halo-terminated dialkane ether of formula (II)

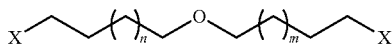

wherein X is halo;
(c) performing an aqueous work-up of the solution of step (b) in order to isolate an organic fraction of the compound of formula (III); and
(d) treating the crude compound of formula (III) of step (c) with a hydroxide or oxide of an alkali or earth alkaline metal in a suitable solvent.

In one embodiment, the process for preparing a crystalline salt of a α,ω-dicarboxylic acid-terminated dialkane ether of formula (IV) comprises:
(e) precipitating the salt of the α,ω-dicarboxylic acid-terminated dialkane ether of formula (IV) in the presence of an organic solvent; or, alternatively, removing the organic layer by evaporation to afford crude crystalline α,ω-dicarboxylic acid-terminated dialkane ether salt of formula (IV) as an alcohol solvate or hydrate;
(f) adding one or more anti-solvents to the solid of step (e) in which the salt of the α,ω-dicarboxylic acid-terminated dialkane ether of formula (IV) is insoluble; and
(g) humidifying the precipitate resultant from step (f) to obtain a crystalline salt of a α,ω-dicarboxylic acid-terminated dialkane ether of formula (IV).

In one embodiment, the process for the preparation of a crystalline form of 6,6'-oxybis(2,2-dimethyl-4-hexanoic acid) calcium of formula (4), wherein the process comprises the steps of:
(a) reacting a solution of an α-bromo-isobutyric acid ester of formula (XX):

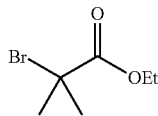

in a suitable solvent or mixture of solvents, under inert atmosphere, with a metal, until the metal is essentially dissolved;
(b) reacting the solution of step (a) with a solution of bis(4-chlorobutylether) of formula (XXI):

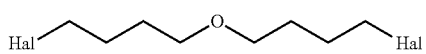

in a suitable solvent or mixture of solvents;
(c) performing an aqueous work-up of the solution of step (b) in order to isolate an organic solution of crude diethyl 6,6'-oxybis(2,2-dimethyl-4-hexanoate) of formula (4);

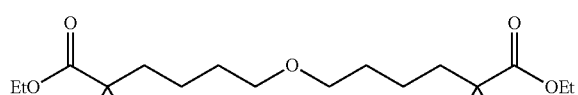

(d) treating the crude diethyl 6,6'-oxybis(2,2-dimethyl-4-hexanoate) of formula (4) of step (c) with a calcium hydroxide or calcium oxide of an alkali or earth alkaline metal in a suitable solvent;
(e) precipitating the 6,6'-oxybis(2,2-dimethyl-4-hexanoic acid) calcium of formula (4)

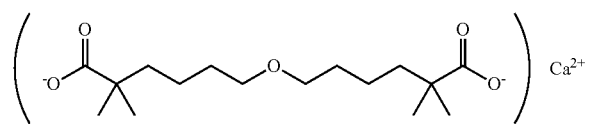

in the presence of an organic solvent; or, alternatively, removing the organic layer by evaporation to afford crude crystalline 6,6'-oxybis(2,2-dimethyl-4-hexanoic acid) salt of formula (4) as an alcohol solvate or hydrate;
(f) adding one or more anti-solvents to the solid of step (e) in which 6,6'-oxybis(2,2-dimethyl-4-hexanoic acid) calcium of formula (4) is insoluble; and
(g) humidifying the precipitate resultant from step (f) to obtain crystalline 6,6'-oxybis(2,2-dimethyl-4-hexanoic acid) calcium of formula (4).

In a particular embodiment, the invention provides a method for the preparation of a α,ω-dicarboxylic acid-terminated dialkane ether, wherein the process comprises the steps of:
(a) reacting a solution of an α-bromo-isobutyric acid ester of formula (XX) in a suitable solvent or mixture of solvents, under inert atmosphere, with a metal, until the metal is essentially dissolved;
(b) reacting the solution of step (a) with a solution of bis(4-chlorobutylether) of formula (XXI) in a suitable solvent or mixture of solvents;
(c) performing an aqueous work-up of the solution of step (b) in order to isolate an organic solution of crude diethyl 6,6'-oxybis(2,2-dimethyl-4-hexanoate) of formula (4);
(d) treating the crude diethyl 6,6'-oxybis(2,2-dimethyl-4-hexanoate) of formula (4) of step (c) with a calcium hydroxide or calcium oxide of an alkali or earth alkaline metal in a suitable solvent.

In a further embodiment, the process further comprises the preparation of 6,6'-oxybis(2,2-dimethyl-4-hexanoic acid) calcium of formula (4), wherein the process comprises the steps of:
(e) precipitating the 6,6'-oxybis(2,2-dimethyl-4-hexanoic acid) calcium of formula (4) in the presence of an organic solvent; or, alternatively, removing the organic layer by evaporation to afford crude crystalline 6,6'-oxybis(2,2-dimethyl-4-hexanoic acid) salt of formula (4) as an alcohol solvate or hydrate;
(f) adding one or more anti-solvents to the solid of step (e) in which 6,6'-oxybis(2,2-dimethyl-4-hexanoic acid) calcium of formula (4) is insoluble; and
(g) humidifying the precipitate resultant from step (f) to obtain crystalline 6,6'-oxybis(2,2-dimethyl-4-hexanoic acid) calcium of formula (4).

A further aspect is a process for preparing a compound of formula (48) using a Williamson ether synthesis:

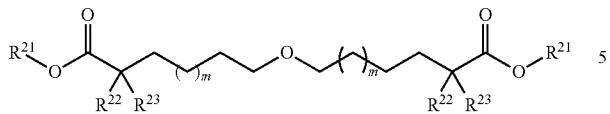

wherein:
R²¹ is alkyl;
R²² and R²³ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a first solution of a compound of formula (46):

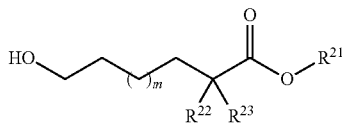

with a halogen source to produce a compound of formula (47):

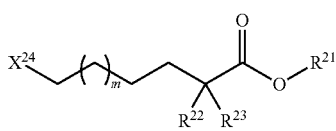

wherein X²⁴ is F, Cl, or I;
(b) reacting a second solution of a compound of formula (46) with the intermediate of formula (37) in the presence of base to form a compound of formula (48).

In some embodiments, step (a) is in the presence of triphenylphosphine.

A further aspect is a process for preparing a compound of formula (48a) using a Williamson ether synthesis:

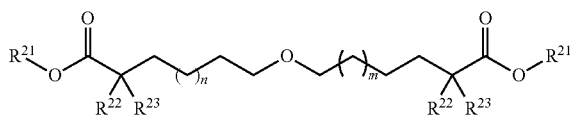

wherein:
R²¹ is alkyl;
R²² and R²³ are each independently alkyl, cycloalkyl, cycloalkylalkyl, heterocycloalkyl, heterocycloalkylalkyl, arylalkyl, heteroaryl, or heteroarylalkyl; and
m and n are each in is 0-4;
comprising:
(a) reacting a solution of a compound of formula (46a):

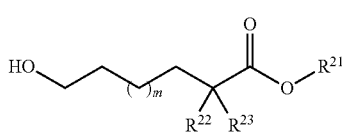

with a halogen source to produce a compound of formula (47):

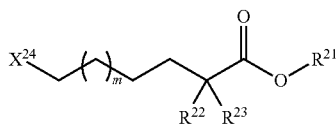

wherein X²⁴ is F, Cl, or I;
(b) reacting a solution of a compound of formula (46b):

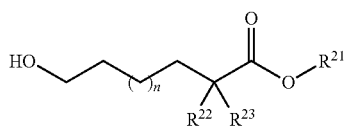

with the intermediate of formula (47) in the presence of base to form a compound of formula (48a).

In some embodiments, the compound of formula (46a) is different than the compound of formula (46b). In some embodiments, the compound of formula (46a) is the same as compound (46b).

Some embodiments further comprise the step of reacting the solution of a compound of formula (45):

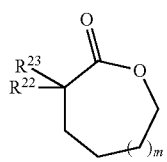

with potassium tert-butoxide to produce an intermediate of formula (46).

Some embodiments further comprise the step of reacting an intermediate of formula (43a):

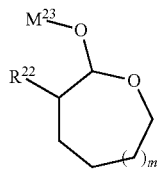

wherein M²³ is Li or Zn;
with a solution of an alkylhalide of formula (44):

R²³.X²³      44 wherein X²³ is halo;
to produce a compound of formula (45).

Some embodiments further comprise the step of reacting the solution of a compound of formula (43):

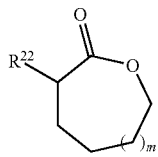

43 with a deprotonating reagent to produce an intermediate of formula (43a).

Some embodiments further comprise the step of reacting the intermediate of formula (41a):

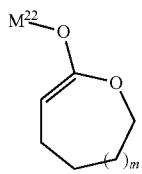

41a wherein $M^{22}$ is Li or Zn;
with a solution of an alkylhalide of formula (42):

42 wherein $X^{22}$ is halo;
to produce a compound of formula (43).

Some embodiments further comprise the step of reacting a solution of a cyclic lactone of formula (41):

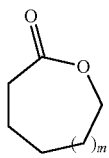

41 with a deprotonating reagent to produce an intermediate of formula (41a).

Some embodiments further comprise the step of hydrolyzing the compound of formula (48) to produce a compound of formula (49).

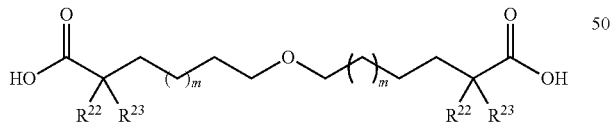

49

In some embodiments, the compound of formula (48) is the di-tert-butyl ester of 6,6'-oxy-bis(2,2-dimethyl-4-hexanoic acid) (14).

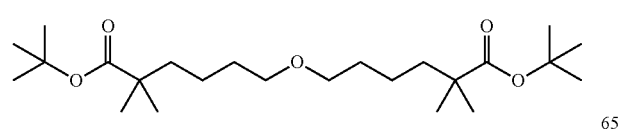

14

Another aspect is a process for preparing a compound of formula (49):

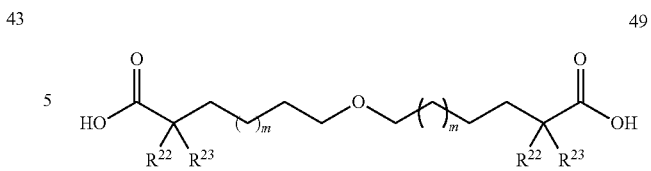

49 wherein:
$R^{22}$ and $R^{23}$ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a solution of a cyclic lactone of formula (41):

41 with a deprotonating reagent to produce an intermediate of formula (41a):

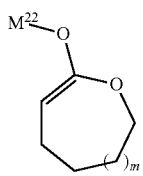

41a wherein $M^{22}$ is Li or Zn;
(b) reacting the intermediate of formula (41a) with a solution of an alkylhalide of formula (42):

42 wherein $X^{22}$ is halo;
to produce a compound of formula (43):

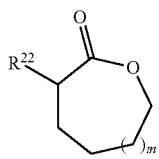

43

(c) reacting the solution of a compound of formula (43) with a deprotonating reagent to produce an intermediate of formula (43a):

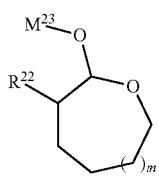

43a wherein $M^{23}$ is Li or Zn;

(d) reacting the intermediate of formula (43a) with a solution of an alkylhalide of formula (44):

$$R^{23}\text{-}X^{23} \qquad 44$$

wherein $X^{23}$ is halo;
to produce a compound of formula (45):

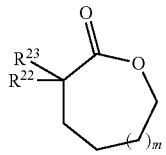

45

(e) reacting the solution of a compound of formula (45) with potassium tert-butoxide to produce an intermediate of formula (46):

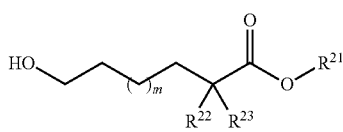

46 wherein $R^{21}$ is tert-butyl;
(f) reacting the solution of a compound of formula (46) with a halogen source to produce an intermediate of formula (47):

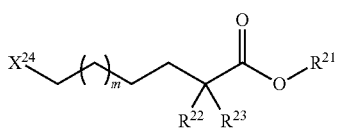

47 wherein $X^{24}$ is F, Cl, or I;
(g) reacting the solution of a compound of formula (46) with the intermediate of formula (47) in the presence of base to form a compound of formula (48):

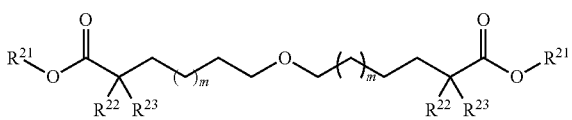

48

(h) reacting the solution of a compound of formula (48) with dilute acid to form 6,6'-oxy-bis(2,2-dimethyl-4-hexanoic acid) (49).

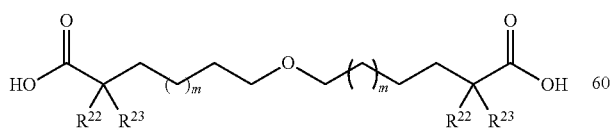

49

In some embodiments, step (f) is performed in the presence of triphenylphosphine, $SOCl_2$ or $SOBr_2$ in pyridine or trialkylamine, or phosphorus (III) bromide or iodide.

More particularly, in one embodiment, step (f) is carried out in the presence of triphenylphosphine.

Some embodiments further comprise the step of:
(i) treating the crude diethyl 6,6'-oxybis(2,2-dimethyl-4-hexanoate) of formula (49) of step (h) with a calcium hydroxide or calcium oxide of an alkali or earth alkaline metal in a suitable solvent.

Some embodiments further comprise the step of
(j) precipitating the 6,6'-oxybis(2,2-dimethyl-4-hexanoic acid) calcium of formula (50):

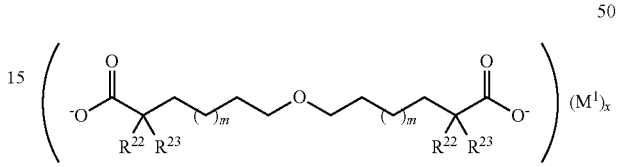

50 in the presence of an organic solvent; or, alternatively, removing the organic layer by evaporation to afford crude crystalline 6,6'-oxybis(2,2-dimethyl-4-hexanoic acid) salt of formula (50) as an alcohol solvate or hydrate.

Some embodiments further comprise the step of:
(k) adding one or more anti-solvents to the solid of step (j) in which 6,6'-oxybis(2,2-dimethyl-4-hexanoic acid) calcium of formula (50) is insoluble.

Some embodiments further comprise the step of:
(l) humidifying the precipitate resultant from step (k) to obtain crystalline 6,6'-oxybis(2,2-dimethyl-4-hexanoic acid) calcium of formula (50).

Another aspect is a process for preparing a compound of formula (48):

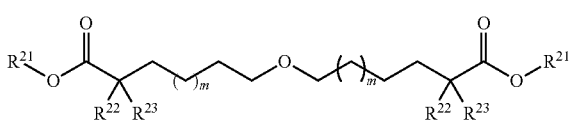

48 wherein:
$R^{21}$ is alkyl;
$R^{22}$ and $R^{23}$ are each independently alkyl, cycloalkyl, cycloalkylalkyl, heterocycloalkyl, heterocycloalkylalkyl, arylalkyl, heteroaryl, or heteroarylalkyl;
m and n are each independently 0-4;
comprising:
(a) reacting a solution of a cyclic lactone of formula (41):

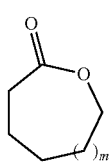

41 with a deprotonating reagent to produce an intermediate of formula (41a):

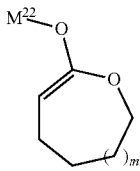

41a wherein $M^{22}$ is Li or Zn;

(b) reacting the intermediate of formula (41a) with a solution of an alkylhalide of formula (42):

$R^{22}$-$X^{22}$   42 wherein $X^{22}$ is halo;
to produce a compound of formula (43):

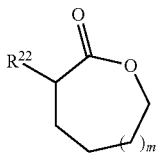

43

(c) reacting the solution of a compound of formula (43) with a deprotonating reagent to produce an intermediate of formula (43a):

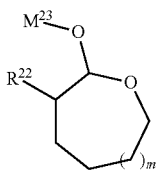

43a wherein $M^{23}$ is Li or Zn;

(d) reacting the intermediate of formula (43a) with a solution of an alkylhalide of formula (44):

$R^{23}$-$X^{23}$   44 wherein $X^{23}$ is halo;
to produce a compound of formula (45):

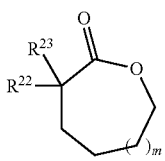

45

(e) reacting the solution of a compound of formula (45) with potassium tert-butoxide to produce an intermediate of formula (46):

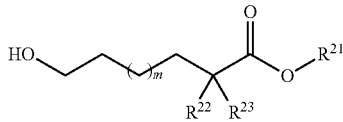

46 where $R^{21}$ is alkyl;

(f) reacting the solution of a compound of formula (46) with a halogen source to produce an intermediate of formula (47):

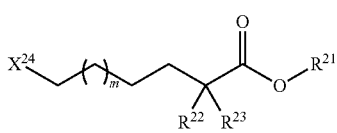

47 wherein $X^{24}$ is F, Cl, or I and where $R^{21}$ is alkyl;

(g) reacting a solution of the compound of formula (46) with the intermediate of formula (47) in the presence of base to form a compound of formula (48).

In some embodiments, step (f) is in the presence of triphenylphosphine.

Another embodiment further comprises the step of performing an aqueous work-up of the solution of step (b) to isolate an organic solution of the compound of formula (43).

Another embodiment further comprises the step of performing an aqueous work-up of the solution of step (d) to isolate an organic solution of the compound of formula (45).

Another embodiment further comprises the step of performing an aqueous work-up of the solution of step (e) to isolate an organic solution of the compound of formula (46).

Another embodiment further comprises the step of performing an aqueous work-up of the solution of step (f) to isolate an organic solution of the compound of formula (47).

Another embodiment further comprises the step of hydrolyzing the compound of formula (48) to produce a compound of formula (49).

49

$$\text{HO}\underset{R^{22}\ R^{23}}{\overset{O}{\diagdown}}\!\!\!\!\!\!\!\!\!\!\!\!\!\!\!\!\!\!\!\!\!\!\!\!\!\!\!\!\text{-}\!\!\!\!(\ )_m\!\!\!\!-\!\!\text{O}\!\!-\!\!(\ )_m\!\!\!\!\underset{R^{22}\ R^{23}}{\overset{O}{\diagdown}}\!\!\!\!\!\!\!\!\!\!\!\!\!\!\!\!\!\!\!\!\!\!\!\!\!\!\!\!\!\!\text{OH}$$

Another embodiment further comprises treating a solution of a compound of formula (48) with dilute acid.

Some embodiments further comprise treating a solution of a compound of formula (48) in a water-immiscible solvent with dilute acid, wherein the water-immiscible solvent is selected from dichloromethane, diethyl ether, tetrahydrofuran, 2-methyltetrahydrofuran, benzene, toluene, xylene, hydrocarbon solvents such as pentane, hexane, and heptane, and mixtures thereof.

Another embodiment further comprises treating a solution of a compound of formula (48) with a dilute acid selected from the group consisting of trifluoroacetic acid, formic acid, hydrochloric acid, and sulfuric acid.

Another embodiment further comprises the step of performing an aqueous work-up of the solution of step (g) to isolate an organic solution of the compound of formula (48).

In some embodiments, $X^{22}$ and $X^{23}$ are each independently F, Cl, or I.

In some embodiments, $R^{21}$ is tert-butyl.

In some embodiments, $R^{22}$ is methyl, ethyl, or methylphenyl.

In some embodiments, $R^{22}$ is methyl.

In some embodiments, $R^{23}$ is methyl, ethyl, or methylphenyl.

In some embodiments, $R^{23}$ is methyl.

In another embodiment, the compound of formula (48) is the di-tert-butyl ester of 6,6'-oxy-bis(2,2-dimethyl-4-hexanoic acid).

14

Another aspect is a process for preparing 6,6'-oxy-bis(2,2-dimethyl-4-hexanoic acid):

3 comprising:

(a) reacting a solution of a cyclic lactone:

51 with a deprotonating reagent to produce an intermediate:

51a wherein $M^{22}$ is Li or Zn;

(b) reacting the intermediate of step (a) with a solution of an alkylhalide $H_3C-X^{22}$  52 wherein $X^{22}$ is halo;

to produce a compound:

53

(c) reacting the solution of the compound of step (b) with a deprotonating reagent to produce an intermediate:

53a wherein $M^{23}$ is Li or Zn;

(d) reacting the intermediate of step (c) with a solution of an alkylhalide:

$H_3C-X^{23}$  54 wherein $X^{23}$ is halo;

to produce a compound:

26

(e) reacting the solution of a compound of step (d) with potassium tert-butoxide to produce an intermediate:

12

(f) reacting a first solution of a compound of step (e) with a halogen source to produce an intermediate:

13a wherein $X^{24}$ is F, Cl, or I;

(g) reacting a second solution of a compound of step (e) with the intermediate of step (f)) in the presence of base to form a compound:

14

(h) reacting the solution of a compound of step (g) with dilute acid to form 6,6'-oxy-bis(2,2-dimethyl-4-hexanoic acid).

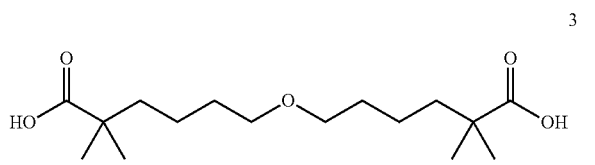 [SMILES: CC(C)(CCCCOCCCCC(C)(C)C(=O)O)C(=O)O]

A further aspect is a process for preparing crystalline 6,6'-oxybis(2,2-dimethyl-4-hexanoic acid) calcium:

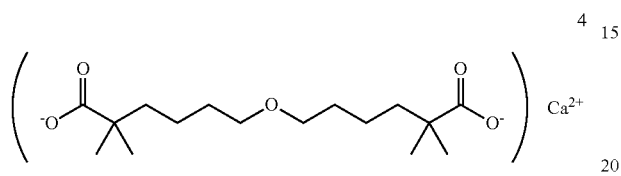

wherein the process comprises:

(a) reacting a solution of a cyclic lactone:

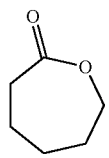

with a deprotonating reagent to produce an intermediate:

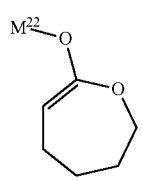

wherein $M^{22}$ is Li or Zn;

(b) reacting the intermediate of step (a) with a solution of an alkylhalide $$H_3C\text{—}X^{22}$$

wherein $X^{22}$ is halo;
to produce a compound:

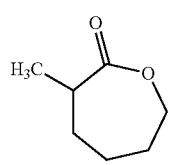

(c) reacting the solution of the compound of step (b) with a deprotonating reagent to produce an intermediate:

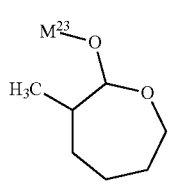

wherein $M^{23}$ is Li or Zn;

(d) reacting the intermediate of step (c) with a solution of an alkylhalide:

$$H_3C\text{—}X^{23}$$

wherein $X^{23}$ is halo;
to produce a compound:

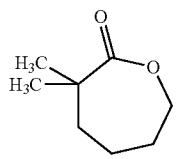

(e) reacting the solution of a compound of step (d) with potassium tert-butoxide to produce an intermediate:

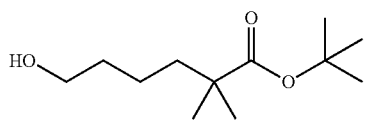

(f) reacting a first solution of a compound of step (e) with a halogen source to produce an intermediate:

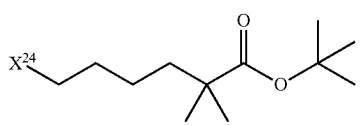

wherein $X^{24}$ is F, Cl, or I;

(g) reacting a second solution of a compound of step (e) with the intermediate of step (f)) in the presence of base to form a compound:

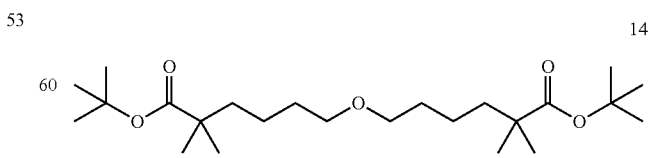

(h) reacting the solution of a compound of step (g) with dilute acid to form 6,6'-oxy-bis(2,2-dimethyl-4-hexanoic acid):

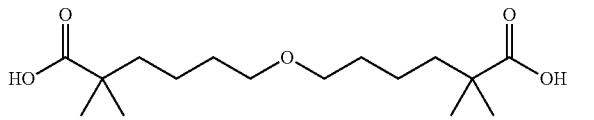

3

(i) treating the crude diethyl 6,6'-oxybis(2,2-dimethyl-4-hexanoate) of step (h) with a calcium hydroxide or calcium oxide of an alkali or earth alkaline metal in a suitable solvent;

(j) precipitating the 6,6'-oxybis(2,2-dimethyl-4-hexanoic acid) calcium of step (i)

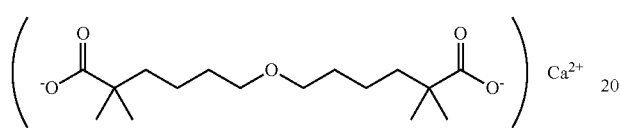

4 in the presence of an organic solvent; or, alternatively, removing the organic layer by evaporation to afford crude crystalline 6,6'-oxybis(2,2-dimethyl-4-hexanoic acid) salt as an alcohol solvate or hydrate;

(k) adding one or more anti-solvents to the solid of step (j) in which 6,6'-oxybis(2,2-dimethyl-4-hexanoic acid) calcium is insoluble; and (l) humidifying the precipitate resultant from step (k) to obtain crystalline 6,6'-oxybis(2,2-dimethyl-4-hexanoic acid) calcium.

In some embodiments, step (f) is in the presence of triphenylphosphine.

In some embodiments, the alcohol solvate or hydrate obtained in step (j) is stirred with tetrahydrofuran with subsequent addition of one or more anti-solvents to obtain the crystalline form of 6,6'-oxybis(2,2-dimethyl-4-hexanoic acid) calcium described in step (k).

A further aspect is a process for preparing a compound of formula (45):

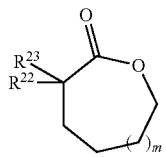

45 wherein:
  $R^{22}$ and $R^{23}$ are each independently alkyl, cycloalkyl, cycloalkylalkyl, heterocycloalkyl, heterocycloalkylalkyl, arylalkyl, heteroaryl, or heteroarylalkyl; and
  m is 0-4;
comprising:
  (a) reacting a solution of a cyclic lactone of formula (41):

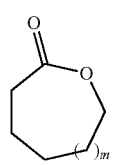

41 with a deprotonating reagent to produce an intermediate of formula (41a):

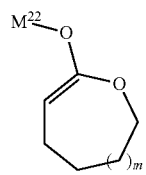

41a wherein $M^{22}$ is Li or Zn;

(b) reacting the intermediate of formula (41a) with a solution of an alkylhalide of formula (42):

$$R^{22}X^{22} \qquad 42$$

wherein $X^{22}$ is halo;
to produce a compound of formula (43):

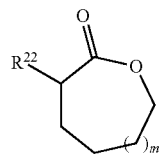

43

(c) reacting the solution of a compound of formula (43) with a deprotonating reagent to produce an intermediate of formula (43a):

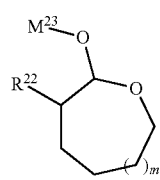

43a wherein $M^{23}$ is Li or Zn;

(d) reacting the intermediate of formula (43a) with a solution of an alkylhalide of formula (44):

$$R^{23}X^{23} \qquad 44$$

wherein $X^{23}$ is halo;
to produce a compound of formula (45).

In some embodiments, m is 1.

In some embodiments, $R^{22}$ and $R^{23}$ are the same. In other embodiments, $R^{23}$ and $R^{22}$ are different.

ADDITIONAL EMBODIMENTS

Embodiment 1

A process for preparing a compound of formula (III):

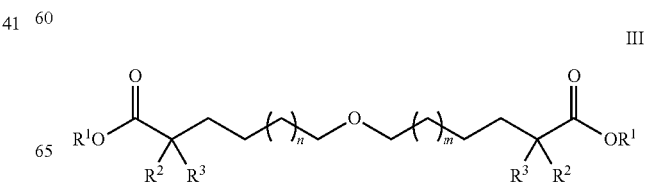

III wherein:

$R^1$ is alkyl;

$R^2$ and $R^3$ are each independently alkyl, cycloalkyl, cycloalkylalkyl, heterocycloalkyl, heterocycloalkylalkyl, aryl, arylalkyl, heteroaryl, or heteroarylalkyl; and n and m are each independently 0-4;

comprising:

(a) reacting a solution comprising a substituted acetic acid ester of formula (I):

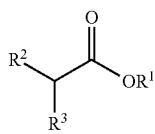

I with a deprotonating reagent to produce an intermediate of formula (Ia):

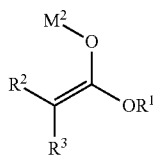

Ia wherein $M^2$ is Li or Zn; and (b) reacting the intermediate of formula (Ia) with a solution comprising a α,ω-halo-terminated dialkane ether of formula (II)

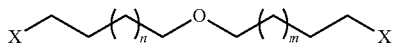

II wherein X is halo;

to produce a compound of formula (III).

Embodiment 2

The process of embodiment 1, further comprising the step of performing an aqueous work-up of the solution of step (b) to isolate an organic solution of the compound of formula (III).

Embodiment 3

The process of any of embodiments 1-2, further comprising the step of treating the crude compound of formula (III) with an aqueous solution of a hydroxide or oxide of an alkali or earth alkaline metal.

Embodiment 4

The process of any of embodiments 1-3, further comprising the step of precipitating the salt of the α,ω-dicarboxylic acid-terminated dialkane ether of formula (IV) in the presence of an organic solvent.

Embodiment 5

The process of any of embodiments 1-4, further comprising the step of removing the organic layer by evaporation to afford crude crystalline α,ω-dicarboxylic acid-terminated dialkane ether salt of formula (IV) in the form of an alcohol solvate or hydrate.

Embodiment 6

The process of any of embodiments 1-5, wherein the alcohol solvate or hydrate is stirred with tetrahydrofuran with subsequent addition of one or more anti-solvents to obtain the crystalline form the α,ω-dicarboxylic acid-terminated dialkane ether salt of formula (IV).

Embodiment 7

The process of any of embodiments 1-6, further comprising the step of adding one or more anti-solvents so that the salt of the α,ω-dicarboxylic acid-terminated dialkane ether of formula (IV) is insoluble.

Embodiment 8

The process of any of embodiments 1-7, further comprising the step of humidifying the precipitate to obtain a crystalline salt of a α,ω-dicarboxylic acid-terminated dialkane ether of formula (IV).

Embodiment 9

The process of any of embodiments 1-8, further comprising the step of hydrolyzing the compound of formula (III) to produce a compound of formula (V).

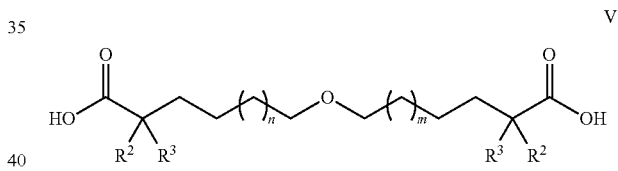

V

Embodiment 10

The process of any of embodiments 1-9, comprising treating a solution of a compound of formula (III) in a water-miscible solvent with an aqueous solution of a base, wherein the water-miscible solvent is selected from DMSO, DMF, methanol, isopropyl alcohol, and ethanol.

Embodiment 11

The process of any of embodiments 1-10, comprising treating a solution of a compound of formula (III) in a water-immiscible solvent with an aqueous solution of a base, wherein the water-immiscible solvent is selected from toluene, xylene, methyl ethyl ketone, and methyl isobutyl ketone.

Embodiment 12

The process of any of embodiments 1-11, comprising treating a solution of a compound of formula (III) in a water-miscible solvent with an aqueous solution of calcium hydroxide or calcium oxide, wherein the water-miscible solvent is selected from DMSO, DMF, acetone, methanol, isopropyl alcohol, and ethanol.

Embodiment 13

The process of any of embodiments 1-12, comprising treating a solution of a compound of formula (III) in a water-immiscible solvent with an aqueous solution of calcium hydroxide or calcium oxide, wherein the water-immiscible solvent is selected from toluene, xylene, methyl ethyl ketone, and methyl isobutyl ketone.

Embodiment 14

The process of any of embodiments 1-13, wherein step (a) is performed under inert atmosphere.

Embodiment 15

The process of any of embodiments 1-14, wherein the deprotonating reagent is selected from hexyllithium and heptyllithium.

Embodiment 16

The process of any of embodiments 1-15, wherein the solvent in step (a) is selected from dichloromethane, diethyl ether, tetrahydrofuran, 2-methyltetrahydrofuran, dimethylformamide, dimethyl sulfoxide, benzene, toluene, xylene, hydrocarbon solvents such as pentane, hexane, and heptane, and mixtures thereof.

Embodiment 17

The process of any of embodiments 1-16, wherein the solvent in step (b) is dichloromethane, diethyl ether, tetrahydrofuran, 2-methyltetrahydrofuran, benzene, toluene, xylene, hydrocarbon solvents such as pentane, hexane, and heptane, and mixtures thereof.

Embodiment 18

The process of any of embodiments 1-17, wherein X is F, Cl, or I.

Embodiment 19

The process of any of embodiments 1-18, wherein X is Cl.

Embodiment 20

The process of any of embodiments 1-19, wherein $R^1$ is methyl or ethyl.

Embodiment 21

The process of any of embodiments 1-20, wherein $R^1$ is ethyl.

Embodiment 22

The process of any of embodiments 1-21, wherein $R^2$ is methyl, ethyl, or phenyl.

Embodiment 23

The process of any of embodiments 1-22, wherein $R^2$ is methyl.

Embodiment 24

The process of any of embodiments 1-23, wherein $R^3$ is methyl, ethyl, or phenyl.

Embodiment 25

The process of any of embodiments 1-24, wherein $R^3$ is methyl.

Embodiment 26

The process of any of embodiments 1-25, wherein n and m are the same.

Embodiment 27

The process of any of embodiments 1-26, wherein n and m are different.

Embodiment 28

The process of any of embodiments 1-27, wherein n and m are each 1.

Embodiment 29

The process of any of embodiments 1-28, wherein the compound of formula (III) is 6,6'-oxy-bis(2,2-dimethyl-4-hexanoic acid) (Compound 3).

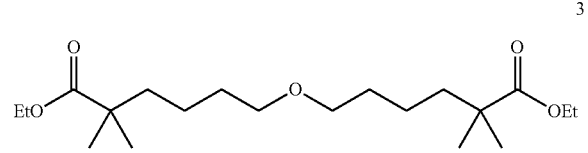 [SMILES: CCOC(=O)C(C)(C)CCCCOCCCCC(C)(C)C(=O)OCC]

Embodiment 30

A process for preparing 6,6'-oxy-bis(2,2-dimethyl-4-hexanoic acid):

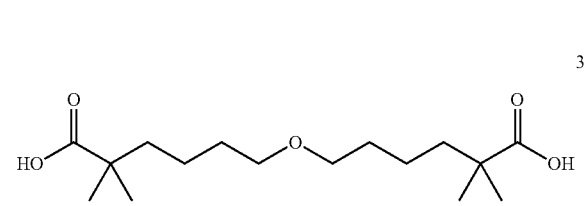 [SMILES: CC(C)(CCCCOCCCCC(C)(C)C(=O)O)C(=O)O]

comprising:
(a) reacting a solution comprising a substituted acetic acid ester of formula (IXa):

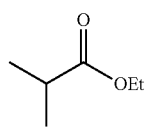

with a deprotonating reagent to produce an intermediate of formula (X):

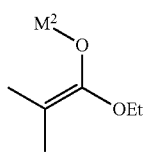

wherein $M^2$ is Li or Zn;
(b) reacting the intermediate of formula (X) with a solution comprising a α,ω-halo-terminated dialkane ether of formula (XI)

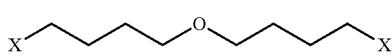

wherein X is halo; and
(c) hydrolyzing the crude diethyl 6,6'-oxybis(2,2-dimethyl-4-hexanoate);
to produce 6,6'-oxy-bis(2,2-dimethyl-4-hexanoic acid).

Embodiment 31

A process for preparing crystalline 6,6'-oxybis(2,2-dimethyl-4-hexanoic acid) calcium of formula (4):

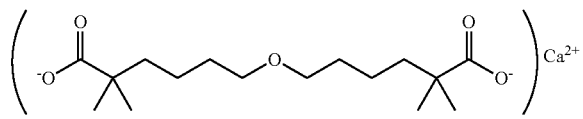

wherein the process comprises:
(a) reacting a solution of ethyl isobutyrate of formula (IX)

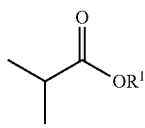

with a deprotonating reagent to produce a compound of formula (X);

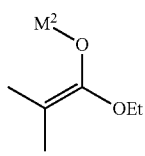

(b) reacting the ethyl lithiobutyrate of step (a) with a solution of bis(4-chlorobutylether) of formula (XI);

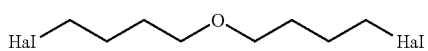

(c) performing an aqueous work-up of the solution of step (b) in order to isolate an organic solution of crude diethyl 6,6'-oxybis(2,2-dimethyl-4-hexanoate) of formula (3);

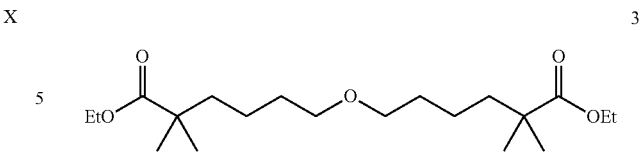

(d) treating the crude diethyl 6,6'-oxybis(2,2-dimethyl-4-hexanoate) of formula (3) of step (c) with a calcium hydroxide or calcium oxide of an alkali or earth alkaline metal in a suitable solvent;
(e) precipitating the 6,6'-oxybis(2,2-dimethyl-4-hexanoic acid) calcium of formula (4):

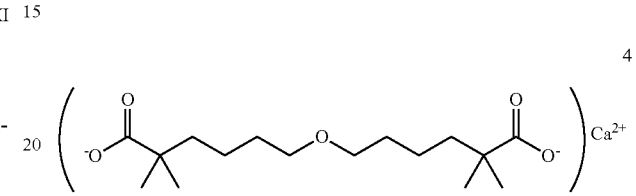

in the presence of an organic solvent; or, alternatively, removing the organic layer by evaporation to afford crude crystalline 6,6'-oxybis(2,2-dimethyl-4-hexanoic acid) salt of formula (4) as an alcohol solvate or hydrate;
(f) adding one or more anti-solvents to the solid of step (e) in which 6,6'-oxybis(2,2-dimethyl-4-hexanoic acid) calcium of formula (4) is insoluble; and
(g) humidifying the precipitate resultant from step (f) to obtain crystalline 6,6'-oxybis(2,2-dimethyl-4-hexanoic acid) calcium of formula (4).

Embodiment 32

The process of embodiment 31, wherein the alcohol solvate or hydrate obtained in step (f) is stirred with tetrahydrofuran with subsequent addition of one or more anti-solvents to obtain the crystalline form of 6,6'-oxybis(2,2-dimethyl-4-hexanoic acid) calcium described in step (g).

Embodiment 33

The process of any of embodiments 31-32, wherein the solid obtained according to step (d) is stirred with tetrahydrofurane with subsequent addition of one or more anti-solvents to obtain the crystalline form of 6,6'-oxybis(2,2-dimethyl-4-hexanoic acid) calcium described in step (g).

Embodiment 34

The process of any of embodiments 31-32, comprising treating a solution of ethyl 6,6'-oxybis(2,2-dimethyl-4-hexanoate) of formula (3) in a water-immiscible solvent with an aqueous solution of a base, wherein the water-miscible solvent is selected from DMSO, DMF, acetone, methanol, isopropyl alcohol, and ethanol.

Embodiment 35

The process of any of embodiments 31-32, comprising treating a solution of ethyl 6,6'-oxybis(2,2-dimethyl-4-hexanoate) of formula (3) in a water-immiscible solvent with an aqueous solution of a base, wherein the water-immiscible solvent is selected from toluene, xylene, methyl ethyl ketone, and methyl isobutyl ketone.

Embodiment 36

The process of any of embodiments 31-32, comprising treating a solution of ethyl 6,6'-oxybis(2,2-dimethyl-4-hexanoate) of formula (3) in a water-miscible solvent with an aqueous solution of calcium hydroxide or calcium oxide, wherein the water-miscible solvent is selected from DMSO, DMF, acetone, methanol, isopropyl alcohol, and ethanol.

Embodiment 37

The process of any of embodiments 31-32, comprising treating a solution of ethyl 6,6'-oxybis(2,2-dimethyl-4-hexanoate) of formula (3) in a water-immiscible solvent with an aqueous solution of a calcium hydroxide or calcium oxide, wherein the water-immiscible solvent is selected from toluene, xylene, methyl ethyl ketone, and methyl isobutyl ketone.

Embodiment 38

A process for preparing a compound of formula (III):

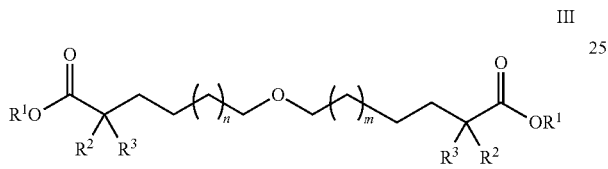

III wherein:
R$^1$ is alkyl;
R$^2$ and R$^3$ are each independently alkyl, cycloalkyl, cycloalkylalkyl, heterocycloalkyl, heterocycloalkylalkyl, aryl, arylalkyl, heteroaryl, or heteroarylalkyl; and
n and m are each independently 0-4;
comprising:
(a) reacting a solution comprising an α-bromo-acetic acid ester of formula (XV):

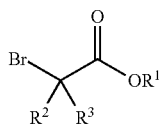

XV with a metal, until the metal is essentially dissolved;
(b) reacting the solution of step (a) with a solution comprising a α,ω-halo-terminated dialkane ether of formula (II):

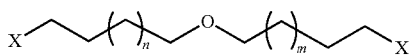

II wherein X is halo;
to produce a compound of formula (III).

Embodiment 39

The process of embodiment 38, further comprising the step of performing an aqueous work-up of the solution of step (b) to isolate an organic solution of the compound of formula (III).

Embodiment 40

The process of any of embodiments 38-39, further comprising the step of treating the crude compound of formula (III) with a hydroxide or oxide of an alkali or earth alkaline metal.

Embodiment 41

The process of any of embodiments 38-40, further comprising the step of precipitating the salt of the α,ω-dicarboxylic acid-terminated dialkane ether of formula (IV) in the presence of an organic solvent.

Embodiment 42

The process of any of embodiments 38-41, further comprising the step of removing the organic layer by evaporation to afford crude crystalline α,ω-dicarboxylic acid-terminated dialkane ether salt of formula (IV) in the form of an alcohol solvate or hydrate.

Embodiment 43

The process of any of embodiments 38-42, wherein the alcohol solvate or hydrate is stirred with tetrahydrofuran with subsequent addition of one or more anti-solvents to obtain the crystalline form the α,ω-dicarboxylic acid-terminated dialkane ether salt of formula (IV).

Embodiment 44

The process of any of embodiments 38-43, further comprising the step of adding one or more anti-solvents so that the salt of the α,ω-dicarboxylic acid-terminated dialkane ether of formula (IV) is insoluble.

Embodiment 45

The process of any of embodiments 38-44, further comprising the step of humidifying the precipitate to obtain a crystalline salt of a α,ω-dicarboxylic acid-terminated dialkane ether of formula (IV).

Embodiment 46

The process of embodiment 38-45, further comprising the step of hydrolyzing the compound of formula (III) to produce a compound of formula (V).

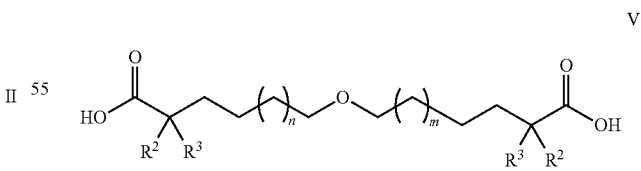

V

Embodiment 47

The process of any of embodiments 38-46, comprising treating a solution of a compound of formula (III) in a water-miscible solvent with an aqueous solution of a base, wherein the water-miscible solvent is selected from DMSO, DMF, methanol, isopropyl alcohol, and ethanol.

49

Embodiment 48

The process of any of embodiments 38-47, comprising treating a solution of a compound of formula (III) in a water-immiscible solvent with an aqueous solution of a base, wherein the water-immiscible solvent is selected from toluene, xylene, methyl ethyl ketone, and methyl isobutyl ketone.

Embodiment 49

The process of any of embodiments 38-48, comprising treating a solution of a compound of formula (III) in a water-miscible solvent with an aqueous solution of calcium hydroxide or calcium oxide, wherein the water-miscible solvent is selected from DMSO, DMF, acetone, methanol, isopropyl alcohol, and ethanol.

Embodiment 50

The process of any of embodiments 38-49, comprising treating a solution of a compound of formula (III) in a water-immiscible solvent with an aqueous solution of calcium hydroxide or calcium oxide, wherein the water-immiscible solvent is selected from toluene, xylene, methyl ethyl ketone and methyl isobutyl ketone.

Embodiment 51

The process of any of embodiments 38-50, wherein step (a) is performed under inert atmosphere.

Embodiment 52

The process of any of embodiments 38-51, wherein the deprotonating reagent is selected from alkyl-lithium, aryl-lithium, dialkyl-zinc, or alkali metal salts of hexamethyldisililazanes.

Embodiment 53

The process of any of embodiments 38-52, wherein the solvent in step (a) is selected from tetrahydrofuran, 2-methyltetrahydrofuran, or toluene.

Embodiment 54

The process of any of embodiments 38-53, wherein X is F, Cl, or I.

Embodiment 55

The process of any of embodiments 38-54, wherein X is Cl.

Embodiment 56

The process of any of embodiments 38-55, wherein $R^1$ is methyl or ethyl.

Embodiment 57

The process of any of embodiments 38-56, wherein $R^1$ is ethyl.

50

Embodiment 58

The process of any of embodiments 38-57, wherein $R^2$ is methyl, ethyl, or phenyl.

Embodiment 59

The process of any of embodiments 38-58, wherein $R^2$ is methyl.

Embodiment 60

The process of any of embodiments 38-59, wherein $R^3$ is methyl, ethyl, or phenyl.

Embodiment 61

The process of any of embodiments 38-60, wherein $R^3$ is methyl.

Embodiment 62

The process of any of embodiments 38-61, wherein n and m are the same.

Embodiment 63

The process of any of embodiments 38-62, wherein n and m are different.

Embodiment 64

The process of any of embodiments 38-63, wherein n and m are each 1.

Embodiment 65

The process of any of embodiments 38-64, wherein the metal is selected from the group consisting of zinc, magnesium and indium.

Embodiment 66

The process of any of embodiments 38-65, wherein catalysts or initiators are optionally used in step (a).

Embodiment 67

The process of any of embodiments 38-66, wherein catalysts or initiators are selected from the group consisting of benzoyl peroxide, 3-chloroperbenzoic acid or magnesium monoperoxyphthalate.

Embodiment 68

The process of any of embodiments 38-67, wherein the compound of formula (III) is 6,6'-oxy-bis(2,2-dimethyl-4-hexanoic acid) (Compound 3).

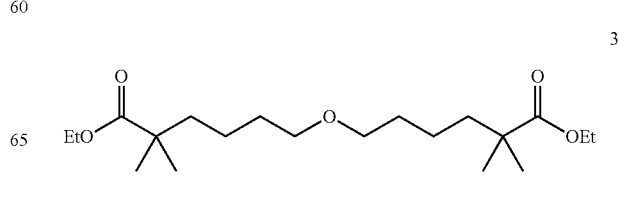

Embodiment 69

A process for preparing 6,6'-oxy-bis(2,2-dimethyl-4-hexanoic acid):

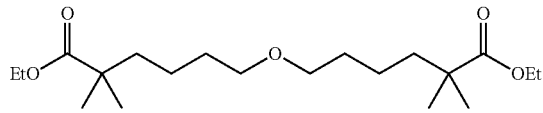

comprising:
(a) reacting a solution comprising an α-bromo-acetic acid ester of formula (XX):

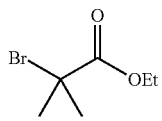

with a metal, until the metal is essentially dissolved;
(b) reacting the solution of step (a) with a solution comprising a α,ω-halo-terminated dialkane ether of formula (XXI):

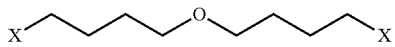

wherein X is halo; and
(c) hydrolyzing the crude diethyl 6,6'-oxybis(2,2-dimethyl-4-hexanoate);
to produce 6,6'-oxy-bis(2,2-dimethyl-4-hexanoic acid).

Embodiment 70

A process for preparing crystalline 6,6'-oxybis(2,2-dimethyl-4-hexanoic acid) calcium of formula (4):

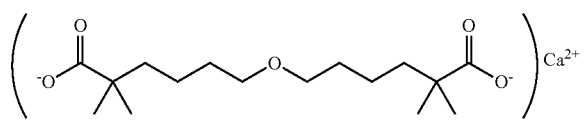

wherein the process comprises:
(a) reacting a solution of an α-bromo-isobutyric acid ester of formula (XX):

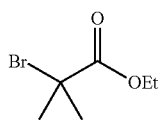

in a suitable solvent or mixture of solvents, under inert atmosphere, with a metal, until the metal is essentially dissolved;

(b) reacting the solution of step (a) with a solution of bis(4-chlorobutylether) of formula (XXI):

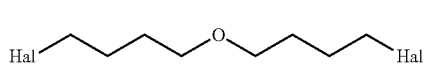

in a suitable solvent or mixture of solvents;
(c) performing an aqueous work-up of the solution of step (b) in order to isolate an organic solution of crude diethyl 6,6'-oxybis(2,2-dimethyl-4-hexanoate) of formula 4;

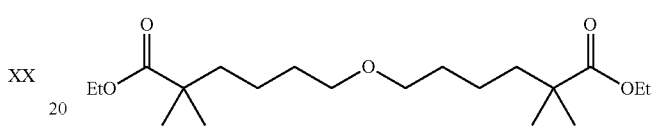

(d) treating the crude diethyl 6,6'-oxybis(2,2-dimethyl-4-hexanoate) of formula (4) of step (c) with a calcium hydroxide or calcium oxide of an alkali or earth alkaline metal in a suitable solvent;
(e) precipitating the 6,6'-oxybis(2,2-dimethyl-4-hexanoic acid) calcium of formula (4):

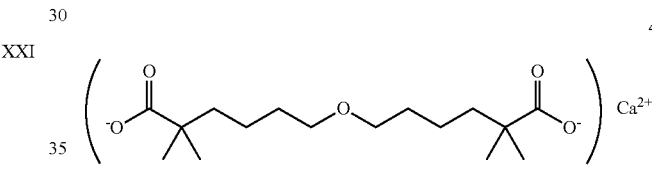

in the presence of an organic solvent; or, alternatively, removing the organic layer by evaporation to afford crude crystalline 6,6'-oxybis(2,2-dimethyl-4-hexanoic acid) salt of formula (4) as an alcohol solvate or hydrate;
(f) adding one or more anti-solvents to the solid of step (e) in which 6,6'-oxybis(2,2-dimethyl-4-hexanoic acid) calcium of formula (4) is insoluble; and
(g) humidifying the precipitate resultant from step (f) to obtain crystalline 6,6'-oxybis(2,2-dimethyl-4-hexanoic acid) calcium of formula (4).

Embodiment 71

The process of embodiment 70, wherein the alcohol solvate or hydrate obtained in step (f) is stirred with tetrahydrofuran with subsequent addition of one or more anti-solvents to obtain the crystalline form of 6,6'-oxybis(2,2-dimethyl-4-hexanoic acid) calcium described in step (g).

Embodiment 72

The process of any of embodiments 70-71, wherein the solid obtained according to step (d) is stirred with tetrahydrofurane with subsequent addition of one or more anti-solvents to obtain the crystalline form of 6,6'-oxybis(2,2-dimethyl-4-hexanoic acid) calcium described in step (g).

Embodiment 73

The process of any of embodiments 70-72, comprising treating a solution of ethyl 6,6'-oxybis(2,2-dimethyl-4- hexanoate) of formula (4) in a in a water-miscible solvent with an aqueous solution of a base, wherein the water-miscible solvent is selected from DMSO, DMF, acetone, methanol, isopropyl alcohol, and ethanol.

Embodiment 74

The process of any of embodiments 70-72, comprising treating a solution of ethyl 6,6'-oxybis(2,2-dimethyl-4-hexanoate) of formula (4) in a water-immiscible solvent with an aqueous solution of a base, wherein the water-immiscible solvent is selected from toluene, xylene, methyl ethyl ketone, and methyl isobutyl ketone.

Embodiment 75

The process of any of embodiments 70-72, comprising treating a solution of ethyl 6,6'-oxybis(2,2-dimethyl-4-hexanoate) of formula (4) in a water-miscible solvent with an aqueous solution of calcium hydroxide or calcium oxide, wherein the water-miscible solvent is selected from DMSO, DMF, acetone, methanol, isopropyl alcohol, and ethanol.

Embodiment 76

The process of any of embodiments 70-72, comprising treating a solution of ethyl 6,6'-oxybis(2,2-dimethyl-4-hexanoate) of formula (4) in a water-immiscible solvent with an aqueous solution of calcium hydroxide or calcium oxide, wherein the water-immiscible solvent is selected from toluene, xylene, methyl ethyl ketone, and methyl isobutyl ketone.

Embodiment 77

A process for preparing a compound of formula (48):

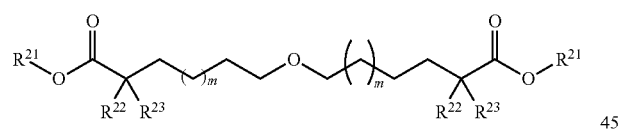
48 wherein:
$R^{21}$ is alkyl;
$R^{22}$ and $R^{23}$ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a solution of a cyclic lactone of formula (41):

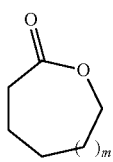
41 with a deprotonating reagent to produce an intermediate of formula (41a):

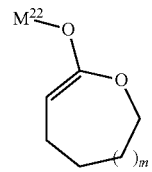
41a wherein $M^{22}$ is Li or Zn;
(b) reacting the intermediate of formula (41a) with a solution of an alkylhalide of formula (42):

$R^{22}X^{22}$  42 wherein $X^{22}$ is halo;
to produce a compound of formula (43):

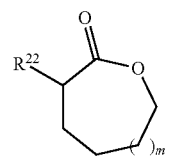
43

(c) reacting the solution of a compound of formula (43) with a deprotonating reagent to produce an intermediate of formula (43a):

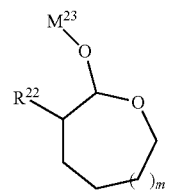
43a wherein $M^{23}$ is Li or Zn;
(d) reacting the intermediate of formula (43a) with a solution of an alkylhalide of formula (44):

$R^{23}X^{23}$  44 wherein $X^{23}$ is halo;
to produce a compound of formula (45):

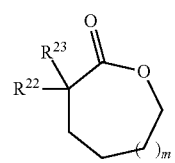
45

(e) reacting the solution of a compound of formula (45) with potassium tert-butoxide to produce an intermediate of formula (46):

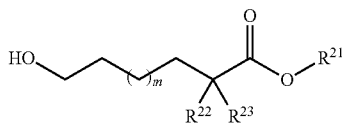

where $R^{21}$ is alkyl;
(f) reacting the solution of a compound of formula (46) with a halogen source to produce an intermediate of formula (47):

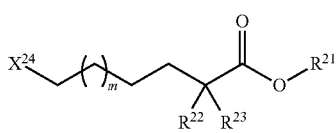

wherein $X^{24}$ is F, Cl, or I and where $R^{21}$ is alkyl;
(g) reacting a solution of the compound of formula (46) with the intermediate of formula (47) in the presence of base to form a compound of formula (48).

Embodiment 78

The process of embodiment 77, further comprising the step of performing an aqueous work-up of the solution of step (b) to isolate an organic solution of the compound of formula (43).

Embodiment 79

The process of any of embodiments 77-78, further comprising the step of performing an aqueous work-up of the solution of step (d) to isolate an organic solution of the compound of formula (45).

Embodiment 80

The process of any of embodiments 77-79, further comprising the step of performing an aqueous work-up of the solution of step (e) to isolate an organic solution of the compound of formula (46).

Embodiment 81

The process of any of embodiments 77-80, further comprising the step of performing an aqueous work-up of the solution of step (0 to isolate an organic solution of the compound of formula (47).

Embodiment 82

The process of any of embodiments 77-81, further comprising the step of hydrolyzing the compound of formula (48) to produce a compound of formula (49).

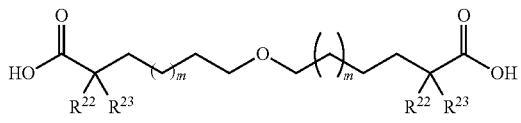

Embodiment 83

The process of any of embodiments 77-82, comprising treating a solution of a compound of formula (48) with dilute acid.

Embodiment 84

The process of any of embodiments 77-83, comprising treating a solution of a compound of formula (48) in a water-immiscible solvent with dilute acid, wherein the water-immiscible solvent is selected from dichloromethane, diethyl ether, tetrahydrofuran, 2-methyltetrahydrofuran, benzene, toluene, xylene, hydrocarbon solvents such as pentane, hexane, and heptane, and mixtures thereof.

Embodiment 85

The process of any of embodiments 77-84, comprising treating a solution of a compound of formula (48) with a dilute acid selected from the group consisting of trifluoroacetic acid, formic acid, hydrochloric acid, and sulfuric acid.

Embodiment 86

The process of any of embodiments 77-85, further comprising the step of performing an aqueous work-up of the solution of step (g) to isolate an organic solution of the compound of formula (48).

Embodiment 87

The process of any of embodiments 77-86, wherein $X^{22}$ and $X^{23}$ are each independently F, Cl, or I.

Embodiment 88

The process of any of embodiments 77-87, wherein $R^{21}$ is tert-butyl.

Embodiment 89

The process of any of embodiments 77-88, wherein $R^{22}$ is methyl, ethyl, or methylphenyl.

Embodiment 90

The process of any of embodiments 77-89, wherein $R^{22}$ is methyl.

Embodiment 91

The process of any of embodiments 77-90, wherein $R^{23}$ is methyl, ethyl, or methylphenyl.

Embodiment 92

The process of any of embodiments 77-91, wherein $R^{23}$ is methyl.

Embodiment 93

The process of any of embodiments 77-92, wherein the compound of formula (38) is the di-tert-butyl ester of 6,6'-oxy-bis(2,2-dimethyl-4-hexanoic acid).

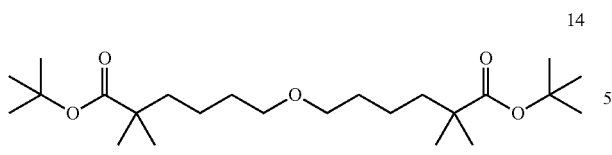

14

Embodiment 94

A process for preparing 6,6'-oxy-bis(2,2-dimethyl-4-hexanoic acid):

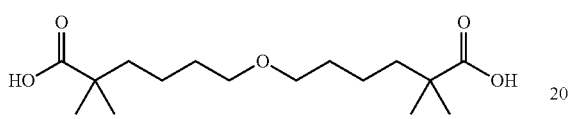

3 comprising:

(a) reacting a solution of a cyclic lactone:

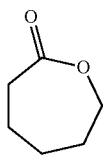

51 with a deprotonating reagent to produce an intermediate:

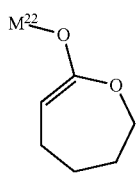

51a wherein $M^{22}$ is Li or Zn;

(b) reacting the intermediate of step (a) with a solution of an alkylhalide

52

$H_3C-X^{22}$ wherein $X^{22}$ is halo;
to produce a compound:

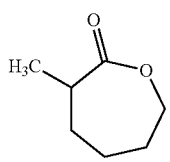

53

(c) reacting the solution of the compound of step (b) with a deprotonating reagent to produce an intermediate:

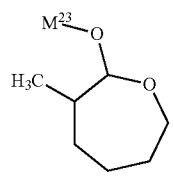

53a wherein $M^{23}$ is Li or Zn;

(d) reacting the intermediate of step (c) with a solution of an alkylhalide:

54

$H_3C-X^{23}$ wherein $X^{23}$ is halo;
to produce a compound:

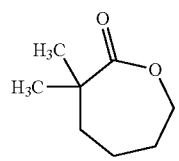

26

(e) reacting the solution of a compound of step (d) with potassium tert-butoxide to produce an intermediate:

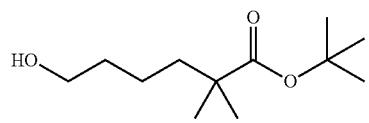

12

(f) reacting a first solution of a compound of step (e) with a halogen source to produce an intermediate:

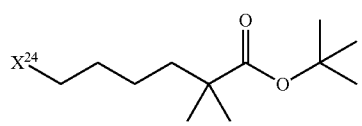

13a wherein $X^{24}$ is F, Cl, or I;

(g) reacting a second solution of a compound of step (e) with the intermediate of step (f)) in the presence of base to form a compound:

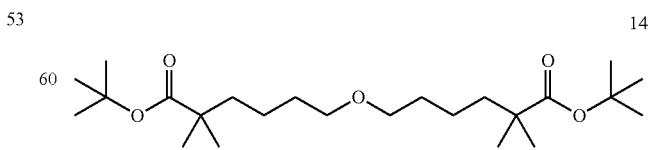

14

(h) reacting the solution of a compound of step (g) with dilute acid to form 6,6'-oxy-bis(2,2-dimethyl-4-hexanoic acid):

Embodiment 95

A process for preparing crystalline 6,6'-oxybis(2,2-dimethyl-4-hexanoic acid) calcium (4):

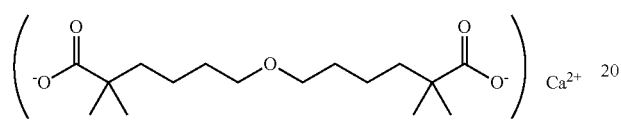

wherein the process comprises:
(a) reacting a solution of a cyclic lactone:

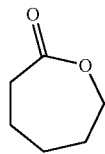

with a deprotonating reagent to produce an intermediate:

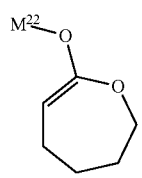

wherein $M^{22}$ is Li or Zn;
(b) reacting the intermediate of step (a) with a solution of an alkylhalide $$H_3C-X^{22}$$

wherein $X^{22}$ is halo;
to produce a compound:

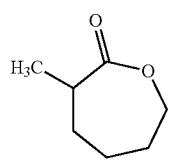

(c) reacting the solution of the compound of step (b) with a deprotonating reagent to produce an intermediate:

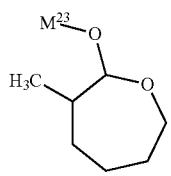

wherein $M^{23}$ is Li or Zn;
(d) reacting the intermediate of step (c) with a solution of an alkylhalide:

$$H_3C-X^{23}$$

wherein $X^{23}$ is halo;
to produce a compound:

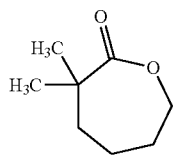

(e) reacting the solution of a compound of step (d) with potassium tert-butoxide to produce an intermediate:

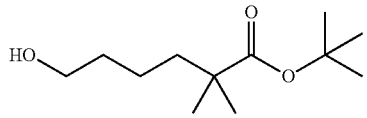

(f) reacting a first solution of a compound of step (e) with a halogen source to produce an intermediate:

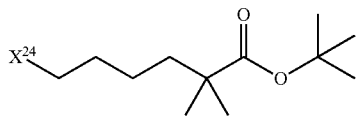

wherein $X^{24}$ is F, Cl, or I;
(g) reacting a second solution of a compound of step (e) with the intermediate of step (f)) in the presence of base to form a compound:

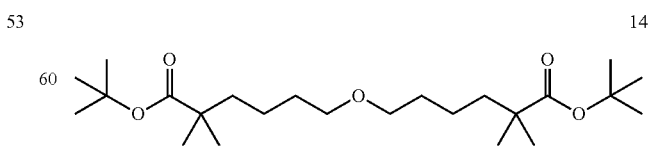

(h) reacting the solution of a compound of step (g) with dilute acid to form 6,6'-oxy-bis(2,2-dimethyl-4-hexanoic acid):

3

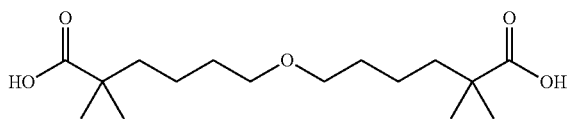

(i) treating the crude diethyl 6,6'-oxybis(2,2-dimethyl-4-hexanoate) of step (h) with a calcium hydroxide or calcium oxide of an alkali or earth alkaline metal in a suitable solvent;
(j) precipitating the 6,6'-oxybis(2,2-dimethyl-4-hexanoic acid) calcium of step (i)

4

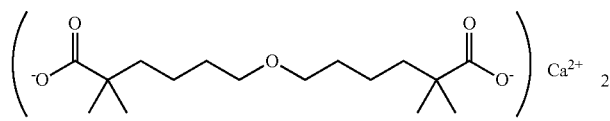

in the presence of an organic solvent; or, alternatively, removing the organic layer by evaporation to afford crude crystalline 6,6'-oxybis(2,2-dimethyl-4-hexanoic acid) salt as an alcohol solvate or hydrate;
(k) adding one or more anti-solvents to the solid of step (j) in which 6,6'-oxybis(2,2-dimethyl-4-hexanoic acid) calcium is insoluble; and
(l) humidifying the precipitate resultant from step (k) to obtain crystalline 6,6'-oxybis(2,2-dimethyl-4-hexanoic acid) calcium (4).

Embodiment 96

The process of embodiment 95, wherein the alcohol solvate or hydrate obtained in step (j) is stirred with tetrahydrofuran with subsequent addition of one or more anti-solvents to obtain the crystalline form of 6,6'-oxybis(2,2-dimethyl-4-hexanoic acid) calcium described in step (k).

Embodiment 97

A process for preparing a compound of formula (48):

48

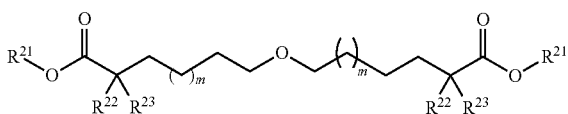

wherein:
R$^{21}$ is alkyl;
R$^{22}$ and R$^{23}$ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a first solution of a compound of formula (46):

46

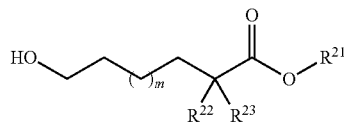

with a halogen source to produce a compound of formula (47):

47

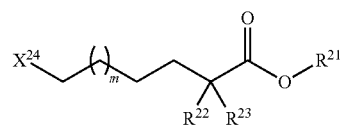

wherein X$^{24}$ is F, Cl, or I;
(b) reacting a second solution of a compound of formula (46) with the intermediate of formula (47) in the presence of base to form a compound of formula (48).

Embodiment 98

The process of embodiment 97, further comprising the step of reacting the solution of a compound of formula (45):

45

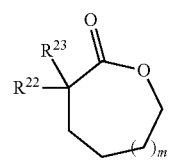

with potassium tert-butoxide to produce an intermediate of formula (46).

Embodiment 99

The process of embodiments 97-98, further comprising the step of reacting an intermediate of formula (43a):

43a

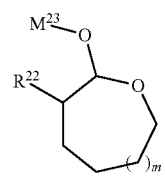

wherein M$^{23}$ is Li or Zn;
with a solution of an alkylhalide of formula (44):

44

wherein X$^{23}$ is halo;
to produce a compound of formula (45).

Embodiment 100

The process of embodiments 97-99, further comprising the step of reacting the solution of a compound of formula (43):

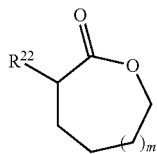

43 with a deprotonating reagent to produce an intermediate of formula (43a).

Embodiment 101

The process of embodiments 97-100, further comprising the step of reacting the intermediate of formula (41a):

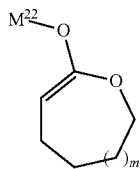

41a wherein $M^{22}$ is Li or Zn;
with a solution of an alkylhalide of formula (42):

    42 wherein $X^{22}$ is halo;
to produce a compound of formula (43).

Embodiment 102

The process of embodiments 97-101, further comprising the step of reacting a solution of a cyclic lactone of formula (41):

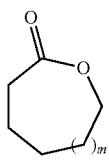

41 with a deprotonating reagent to produce an intermediate of formula (41a).

Embodiment 103

The process of any of embodiments 97-102, further comprising the step of hydrolyzing the compound of formula (48) to produce a compound of formula (49).

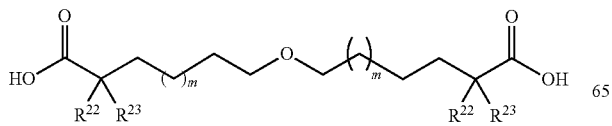

49

Embodiment 104

The process of any of embodiments 97-103, wherein the compound of formula (38) is the di-tert-butyl ester of 6,6'-oxy-bis(2,2-dimethyl-4-hexanoic acid).

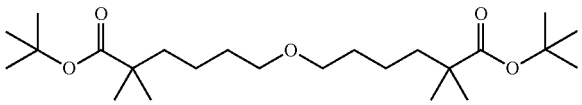

14

Embodiment 105

A process for preparing a compound of formula (45):

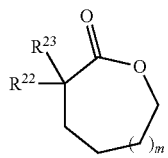

45 comprising:
(a) reacting a solution of a cyclic lactone of formula (41):

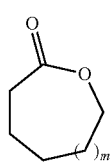

41 with a deprotonating reagent to produce an intermediate of formula (41a):

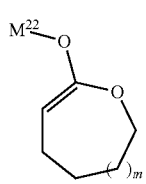

41a wherein $M^{22}$ is Li or Zn;
(b) reacting the intermediate of formula (41a) with a solution of an alkylhalide of formula (42):

$R^{22}.X^{22}$    42 wherein $X^{22}$ is halo;
to produce a compound of formula (43):

43

(c) reacting the solution of a compound of formula (43) with a deprotonating reagent to produce an intermediate of formula (43a):

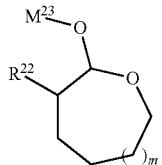

wherein $M^{23}$ is Li or Zn;
(d) reacting the intermediate of formula (43a) with a solution of an alkylhalide of formula (44):

wherein $X^{23}$ is halo;
to produce a compound of formula (45).

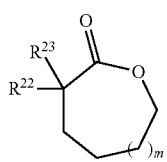

Embodiment 106

The process of any of embodiments 97-103, further comprising the steps of:
(e) treating the crude diethyl 6,6'-oxybis(2,2-dimethyl-4-hexanoate) of formula (49) of step (h) with a calcium hydroxide or calcium oxide of an alkali or earth alkaline metal in a suitable solvent;
(f) precipitating the 6,6'-oxybis(2,2-dimethyl-4-hexanoic acid) calcium of formula (50):

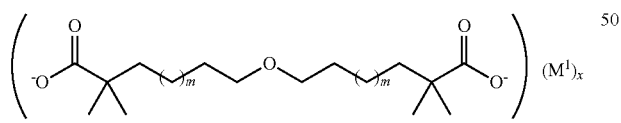

in the presence of an organic solvent; or, alternatively, removing the organic layer by evaporation to afford crude crystalline 6,6'-oxybis(2,2-dimethyl-4-hexanoic acid) salt of formula (50) as an alcohol solvate or hydrate;
(g) adding one or more anti-solvents to the solid of step (j) in which 6,6'-oxybis(2,2-dimethyl-4-hexanoic acid) calcium of formula (50) is insoluble; and
(h) humidifying the precipitate resultant from step (k) to obtain crystalline 6,6'-oxybis(2,2-dimethyl-4-hexanoic acid) calcium of formula (50).

Embodiment 107

A process for preparing a compound of formula (48):

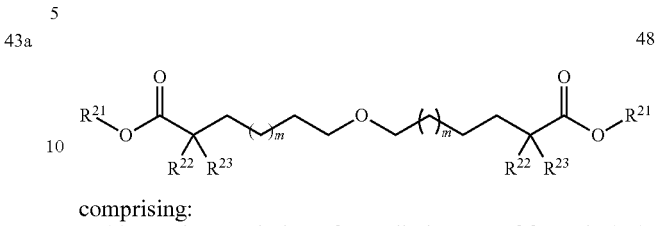

comprising:
(a) reacting a solution of a cyclic lactone of formula (41):

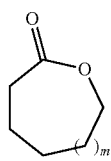

with a deprotonating reagent to produce an intermediate of formula (41a):

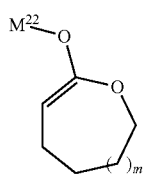

wherein $M^{22}$ is Li or Zn;
(b) reacting the intermediate of formula (41a) with a solution of an alkylhalide of formula (42):

wherein $X^{22}$ is halo;
to produce a compound of formula (43):

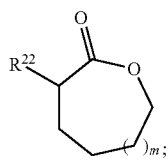

(c) reacting the solution of a compound of formula (43) with a deprotonating reagent to produce an intermediate of formula (43a):

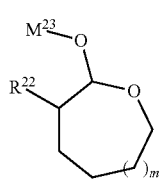

wherein $M^{23}$ is Li or Zn;
(d) reacting the intermediate of formula (43a) with a solution of an alkylhalide of formula (44):

wherein $X^{23}$ is halo;
to produce a compound of formula (45):

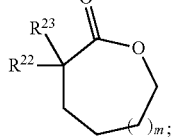
45

(e) reacting the solution of a compound of formula (45) with potassium tert-butoxide to produce an intermediate of formula (46):

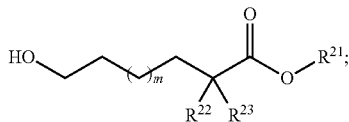
46

(f) reacting the solution of a compound of formula (46) with a halogen source to produce an intermediate of formula (47):

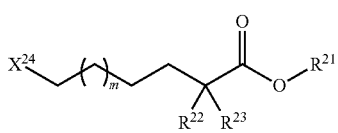
47 wherein $X^{24}$ is F, Cl, or I;

(g) reacting the solution of a compound of formula (46) with the intermediate of formula (47) in the presence of base to form a compound of formula (48):

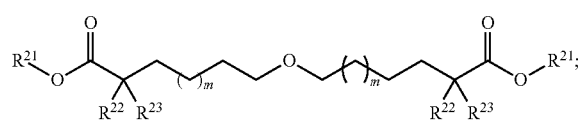
48

(h) reacting the solution of a compound of formula (48) with dilute acid to form (49).

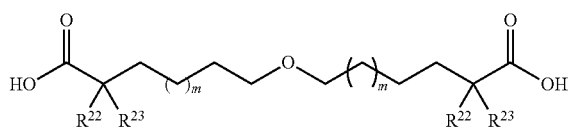
49

Embodiment 108

The process of embodiment 107, wherein the compound of formula (48) is:

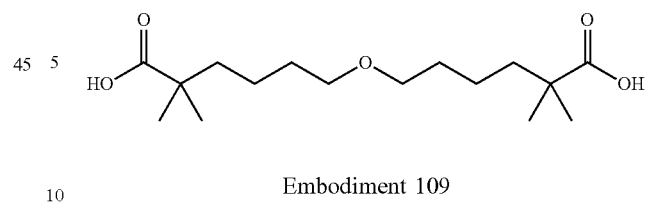
3

Embodiment 109

The process of embodiments 107-108, further comprising any of the following steps:
(i) treating the compound of formula (49) of step (h) with a calcium hydroxide or calcium oxide of an alkali or earth alkaline metal in a suitable solvent;
(j) precipitating the compound of formula (50):

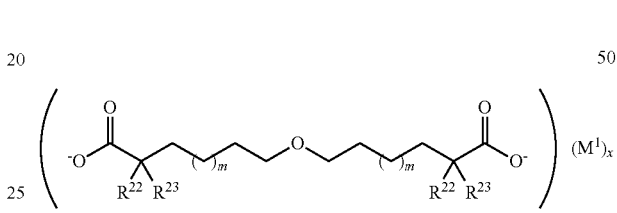
50 wherein $M^1$ is Ca or K and x is 1 or 2;
in the presence of an organic solvent; or, alternatively, removing the organic layer by evaporation to afford a crude crystalline salt of formula (50) as an alcohol solvate or hydrate;
(k) adding one or more anti-solvents to the solid of step (j) in which the compound of formula (50) is insoluble; and
humidifying the precipitate resultant from step (k) to obtain crystalline compound of formula (50).

A further aspect is a process for preparing a compound of formula (45):

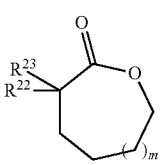
45 wherein:
$R^{22}$ and $R^{23}$ are each independently alkyl, cycloalkyl, cycloalkylalkyl, heterocycloalkyl, heterocycloalkylalkyl, arylalkyl, heteroaryl, or heteroarylalkyl; and
m is 0-4;
comprising:
(a) reacting a solution of a cyclic lactone of formula (41):

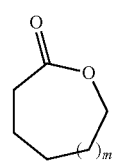
41 with a deprotonating reagent to produce an intermediate of formula (41a):

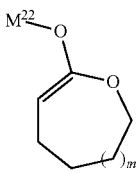

wherein M$^{22}$ is Li or Zn;
(b) reacting the intermediate of formula (41a) with a solution of an alkylhalide of formula (42):

wherein X$^{22}$ is halo;
to produce a compound of formula (43):

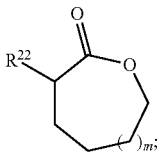

(c) reacting the solution of a compound of formula (43) with a deprotonating reagent to produce an intermediate of formula (43a):

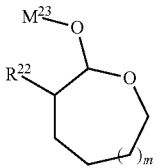

wherein M$^{23}$ is Li or Zn;
(d) reacting the intermediate of formula (43a) with a solution of an alkylhalide of formula (44):

wherein X$^{23}$ is halo;
to produce a compound of formula (45).
In some embodiments, m is 1.
In some embodiments, R$^{22}$ and R$^{23}$ are the same. In other embodiments, R$^{23}$ and R$^{22}$ are different.

General Synthesis of α,ω-Dicarboxylic Acid-Terminated Dialkane Ethers

Four different methodologies are presented for preparing α,ω-dicarboxylic acid-terminated dialkane ethers: (1) the Reformatsky reaction; (2) acid catalyzed ether synthesis; (3) alkylation; and (4) Williamson ether synthesis.

(1) The Reformatsky Reaction:

Compounds of formula (III) and corresponding salts may be prepared under certain conditions using a Reformatsky reaction according to Scheme 4. Ethyl 2-bromoisobutyrate XV and halo-butyl ethers II under various conditions including solvents such as THF, methyl t-butyl ether or and ethyl ether, and zinc such as zinc powder with catalytic amount of iodine or chlorotrimethylsilane, or highly active Rieke® zinc, and at temperatures between 0° C. to 70° C. or in refluxing solvent. Such procedures are described in Cui, H.; et al.; *Org. & Biomed. Chem.* 2013, 10(14), 2862-2869 and Gaudemar-Bardone, F.; et al.; *Synthesis,* 1987, 12, 1130-1133.

Scheme 4

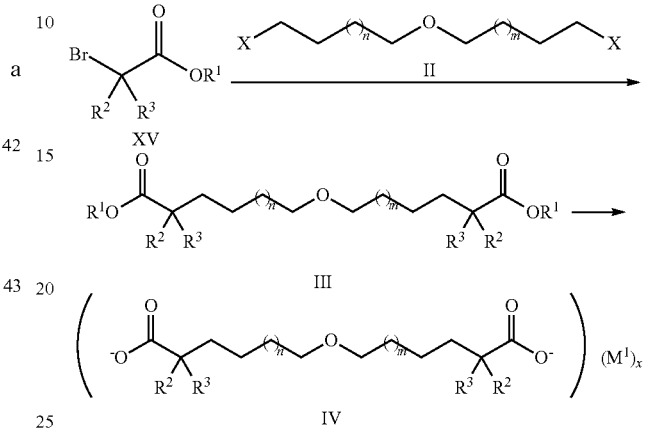

(2) Acid-Catalyzed Ether Synthesis

Compounds of formula (III) and corresponding acids and salts may be prepared using an acid-catalyzed ether synthesis reaction according to Scheme 5. For instance, esters of type 53 can be synthesized by dimerization of alcohols of type 52, using the by the reaction pathway described in Scheme 7, where alcohols 52 are prepared by methods known in the art (e.g., for n=3 in two steps by alkylation of benzyl protected 4-bromobutanol (commercially available from Sigma-Aldrich) with an alkyl isobutyrate (commercially available from various suppliers, such as Sigma-Aldrich), and subsequent hydrogenation.

Scheme 5

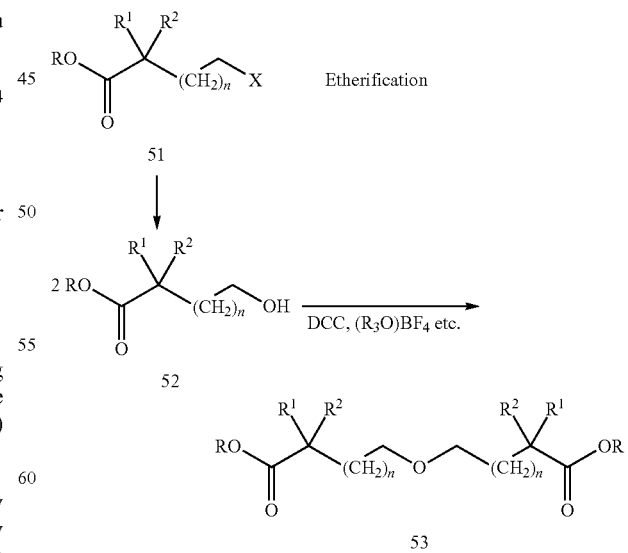

(3) Alkylation Method:

Compounds of formula (III) and corresponding salts may be prepared using an alkylation method according to Scheme 6. The results of the alkylation studies are presented in Table 1, using the general synthesis described in Scheme 6.

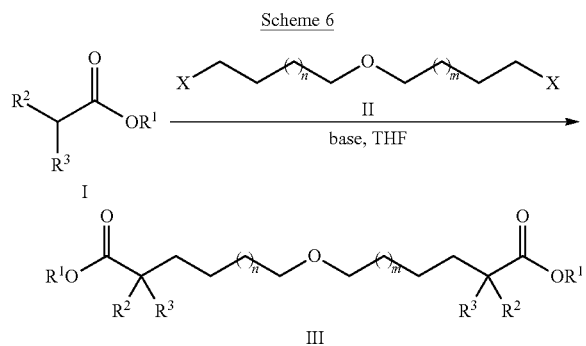

Scheme 6

TABLE 1

Alkylation results for gemcabene diethyl ester and analogs.

| $R^2$ | $R^3$ | X | base | n | m | Yield (%) |
|---|---|---|---|---|---|---|
| Me | Me | Cl | LDA | 1 | 1 | 0 |
| Me | Me | Br | LiHMDS | 1 | 1 | 0 |
| Me | Me | Br | LDA | 1 | 1 | 24* |
| Me | Me | I | LDA (n-BuLi) | 1 | 1 | 98 |
| Me | Me | Br | LDA | 0 | 1 | 85 |
| Me | Me | I | LDA (n-HexylLi) | 1 | 1 | 91 |
| Me | p-Tolyl | I | LDA | 1 | 1 | 89 |
| Me | Me | Br | LDA | 2 | 1 | 79 |
| Me | Me | Br | LDA | 2 | 2 | 89 |

*The bromide contained some chloride that lowered the yield

Using n-hexyllithium or n-butyllithium to generate the LDA produced comparable results. The use of n-hexyllithium is known to be safe and environmentally friendly, therefore such a methodology is largely scalable at multi-kilogram batches. LiHMDS failed to generate any product. Finally, using larger groups (p-tolyl) on the ester did not hinder the alkylation reaction.

(4) Williamson Ether Synthesis:

Compounds of formula (III) and corresponding salts may be prepared using a Williamson ether synthesis according to Scheme 7. The results for various compounds using the Williamson Ether Synthesis method are listed in Table 2, using the general synthesis described in Scheme 7.

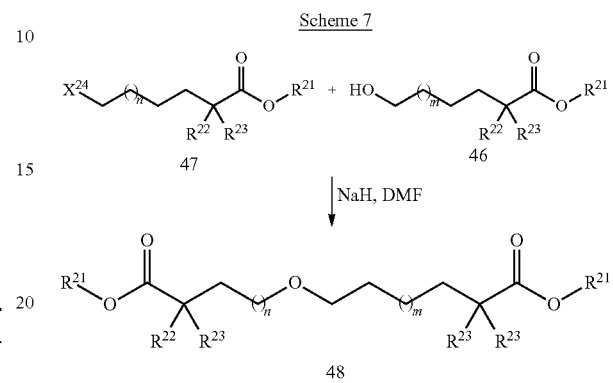

Scheme 7

TABLE 2

Williamson Ether Synthesis Results

| $R^{21}$ | $R^{22}$ | $R^{23}$ | m | n | $X^{24}$ | Yield (%) |
|---|---|---|---|---|---|---|
| Et | Methyl | Methyl | 1 | 1 | Br | 0 |
| Et | Methyl | Methyl | 1 | 1 | I | trace |
| t-butyl | Methyl | Methyl | 1 | 1 | Br | 34% |
| t-butyl | Methyl | Methyl | 1 | 1 | I | 40% |

During the Williamson ether synthesis, the ethyl esters produced primarily trans-esterification products. Replacing the ethyl ester with t-butyl ester prevented the trans-esterification from occurring. A representative method starting from inexpensive and safe starting materials is outlined in Scheme 7a.

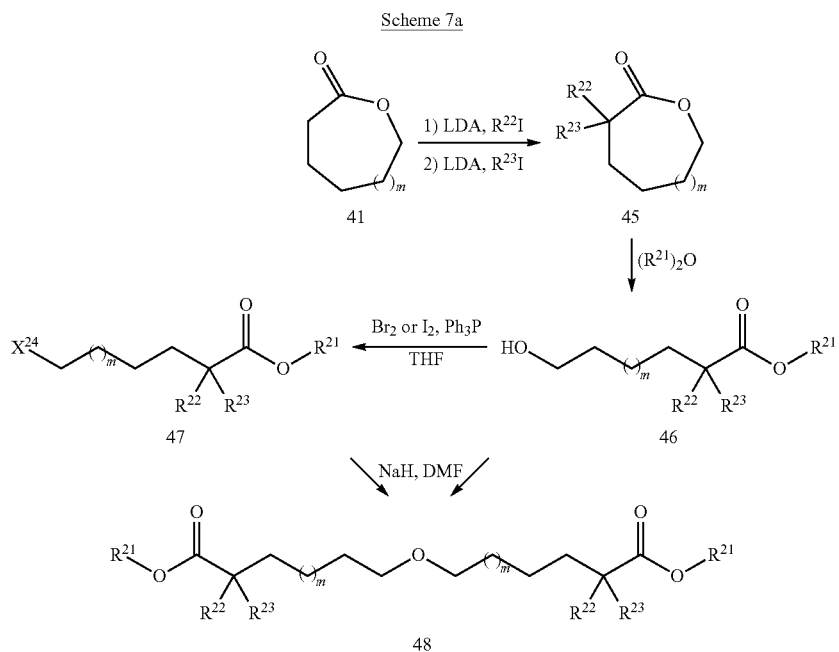

Scheme 7a

The preparation of alcohol 46 begins with, for example, the alkylation of 6-caprolactone using LDA and iodomethane, followed by ring opening with potassium t-butoxide. Other alkylation methodologies for 6-caprolactone may be used, such as ring opening with t-butoxide. The iodide or the bromide of formula (47) may be directly prepared from the alcohol and coupled by the Williamson ether synthesis methodology.

Exemplary compounds and intermediates that may be prepared by these methods are included in Table 3.

TABLE 3

List of Compounds

| # | Structure | Name |
|---|---|---|
| 1 | 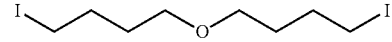 [SMILES: ICCCCOCCCCI] | 4-Iodobutyl ether |
| 2 | 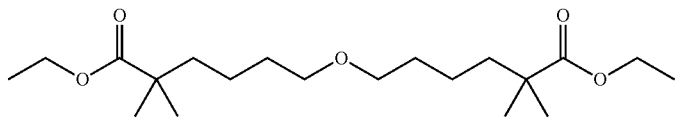 [SMILES: CCOC(=O)C(C)(C)CCCCOCCCCC(C)(C)C(=O)OCC] | 6-(5-Ethoxycarbonyl-5-methyl-hexyloxy)-2,2-dimethylhexanoic acid ethyl ester |
| 3 | 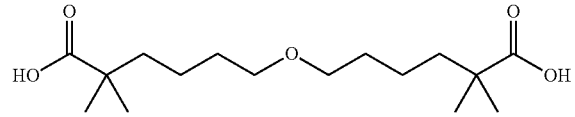 [SMILES: CC(C)(CCCCOCCCCC(C)(C)C(=O)O)C(=O)O] | 6-(5-Carboxyl-5-methyl-hexyloxy)-2,2-dimethylhexanoic acid |
| 4 | 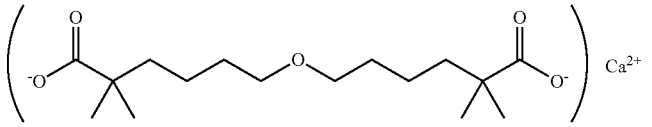 | Gemcabene |
| 5 | 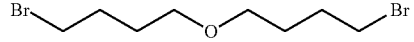 [SMILES: BrCCCCOCCCCBr] | 4-Bromobutyl ether |
| 6 | 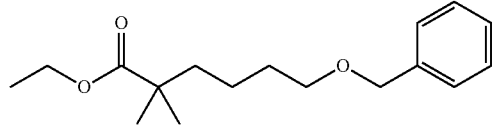 [SMILES: CCOC(=O)C(C)(C)CCCCOCc1ccccc1] | 6-Benzyloxy-2,2-dimethylhexanoic acid ethyl ester |
| 7 | 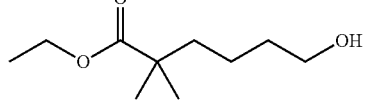 | 6-Hydroxy-2,2-dimethylhexanoic acid ethyl ester |
| 8 | 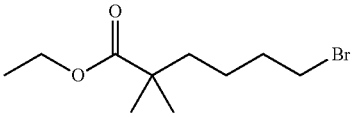 | 6-Bromo-2,2-dimethylhexanoic acid ethyl ester |
| 9 | 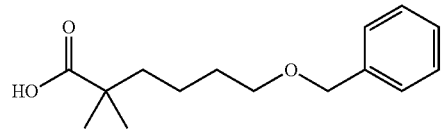 [SMILES: CC(C)(CCCCOCc1ccccc1)C(=O)O] | 6-Benzyloxy-2,2-dimethylhexanoic acid |
| 11 | 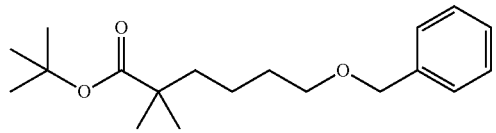 [SMILES: CC(C)(C)OC(=O)C(C)(C)CCCCOCc1ccccc1] | 6-Benzyloxy-2,2-dimethylhexanoic acid tert-butyl ester |
| 12 | 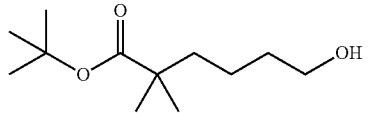 | 6-Hydroxy-2,2-dimethylhexanoic acid t-butyl ester |

TABLE 3-continued

List of Compounds

| # | Structure | Name |
|---|-----------|------|
| 13 | 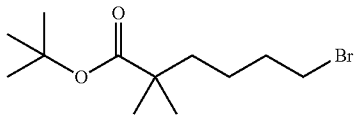 | 6-Bromo-2,2-dimethylhexanoic acid tert-butyl ester |
| 14 | 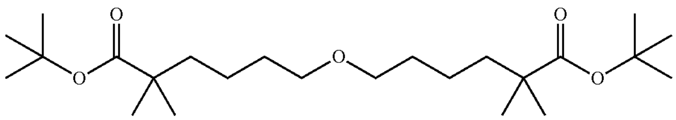 [SMILES: CC(C)(C)OC(=O)C(C)(C)CCCCOCCCCC(C)(C)C(=O)OC(C)(C)C] | 6-(5-tert-Butoxycarbonyl-5-methyl-hexyloxy)-2,2-dimethyl-hexanoic acid tert-butyl ester (14, gemcabene di-t-butyl ester) |
| 15 | 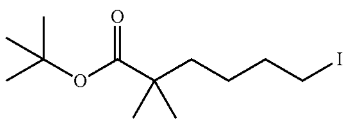 | 6-Iodo-2,2-dimethylhexanoic acid t-butyl ester |
| 16 | 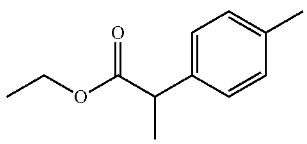 | Ethyl 2-p-tolylpropionate |
| 17 | 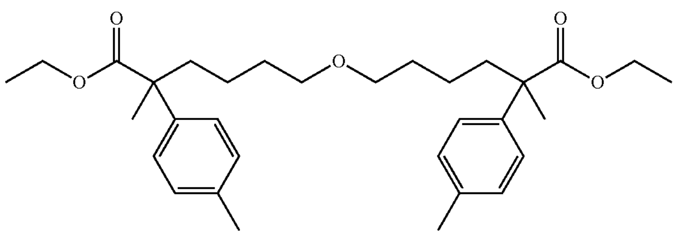 [SMILES: CCOC(=O)C(C)(CCCCOCCCCC(C)(C(=O)OCC)c1ccc(C)cc1)c1ccc(C)cc1] | Diethyl 6,6'-oxybis(2-methyl-2-(p-tolyl)hexanoate) |
| 18 | 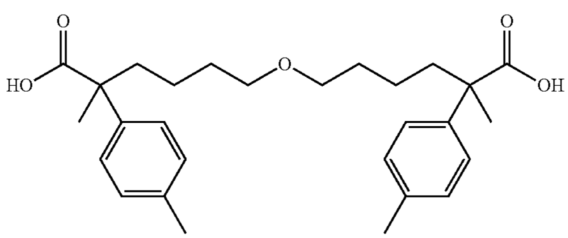 [SMILES: Cc1ccc(C(C)(CCCCOCCCCC(C)(C(=O)O)c2ccc(C)cc2)C(=O)O)cc1] | 6,6'-Oxybis(2-methyl-2-(p-tolyl)hexanoic acid) |
| 19 | 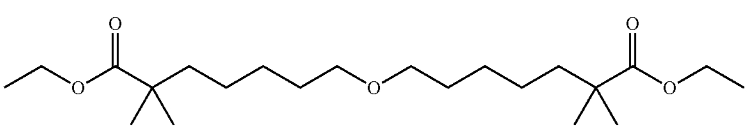 [SMILES: CCOC(=O)C(C)(C)CCCCCOCCCCCC(C)(C)C(=O)OCC] | 7-(6-Ethoxy-carbonyl-6-methylheptyloxy)-2,2-dimethylheptanoic acid ethyl ester |
| 20 | 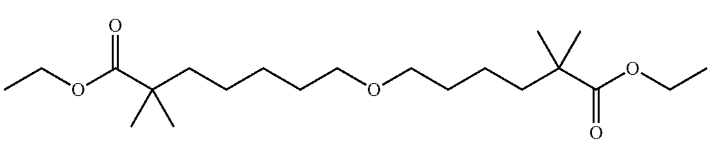 [SMILES: CCOC(=O)C(C)(C)CCCCCOCCCCC(C)(C)C(=O)OCC] | 7-(5-Ethoxy-carbonyl-5-methylhexyloxy)-2,2-dimethyl-heptanoic acid ethyl ester |
| 21 | 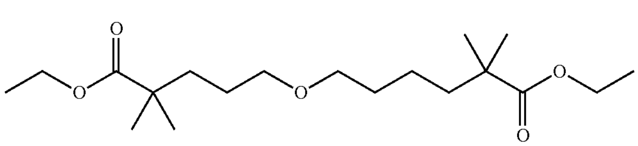 [SMILES: CCOC(=O)C(C)(C)CCCCOCCCC(C)(C)C(=O)OCC] | 6-(4-Ethoxy-carbonyl-4-methylpentyloxy)-2,2-dimethyl-hexanoic acid ethyl ester |
| 22 | 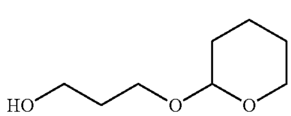 [SMILES: OCCCOC1CCCCO1] | 3-(Tetrahydro-pyran-2-yloxy)-propan-1-ol |

TABLE 3-continued

List of Compounds

| # | Structure | Name |
|---|-----------|------|
| 23 | 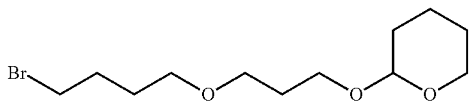 [SMILES: BrCCCCOCCCOC1CCCCO1] | 2-[3-(4-Bromobutoxy)-propoxy]-tetrahydropyran |
| 24 | 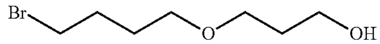 | 3-(4-Bromobutoxy)-propan-1-ol |
| 25 | 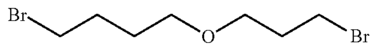 | 1-Bromo-4-(3-bromopropoxy)-butane |
| 26 | 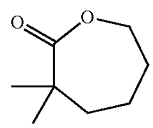 | 3,3-Dimethyl-oxepan-2-one |
| 27 | 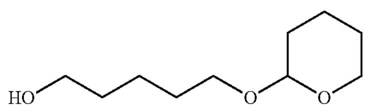 [SMILES: OCCCCCOC1CCCCO1] | 5-(Tetrahydro-pyran-2-yloxy)-pentan-1-ol |
| 28 | 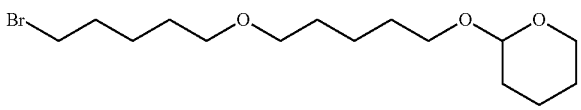 [SMILES: BrCCCCCOCCCCCOC1CCCCO1] | 2-[5-(5-Bromopentyloxy)-pentyloxy]-tetrahydropyran |
| 29 | 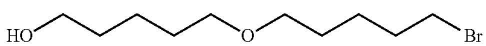 [SMILES: OCCCCCOCCCCCBr] | 5-(5-Bromopentyloxy)-pentan-1-ol |
| 30 | 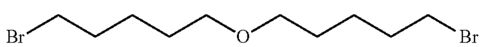 [SMILES: BrCCCCCOCCCCCBr] | 1-Bromo-5-(5-bromopentyloxy)-pentane |
| 31 | 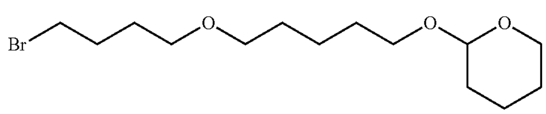 [SMILES: BrCCCCOCCCCCOC1CCCCO1] | 2-[5-(4-Bromobutoxy)-pentyloxy]-tetrahydropyran |
| 32 | 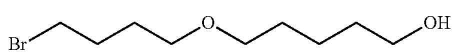 [SMILES: OCCCCCOCCCCBr] | 5-(4-Bromobutoxy)-pentan-1-ol |
| 33 | 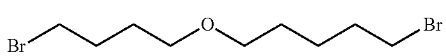 [SMILES: BrCCCCCOCCCCBr] | 1-Bromo-5-(4-bromobutoxy)-pentane |

General Synthesis of Gemcabene

Alkylation Approach:

A representative synthesis of gemcabene is shown in Scheme 8. In this representative example, 4-Chlorobutyl ether was converted into 4-iodobutyl ether 1 with NaI in acetone in 95% yield. The alkyl iodide was treated with ethyl isobutyrate in the presence of LDA, which is freshly prepared from diisopropylamine/n-hexyl lithium or n-butyl lithium, to provide the diester 2 in a high yield. Alternate examples in which the LDA was prepared using either butyllithium or hexyllithium produced comparable yields. The diester 2 was saponified to provide the diacid 3, followed by transformation into gemcabene calcium 4.

Scheme 8

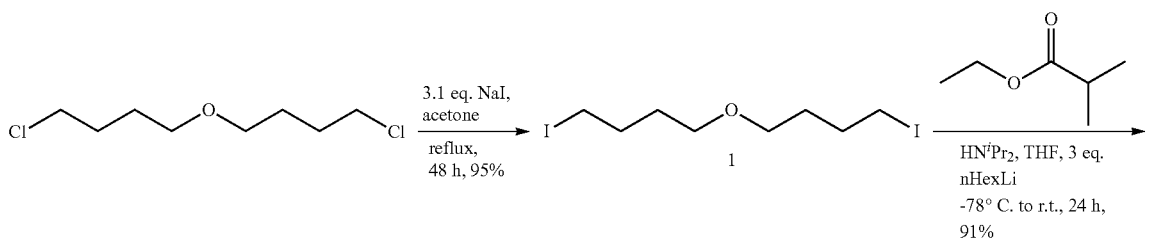

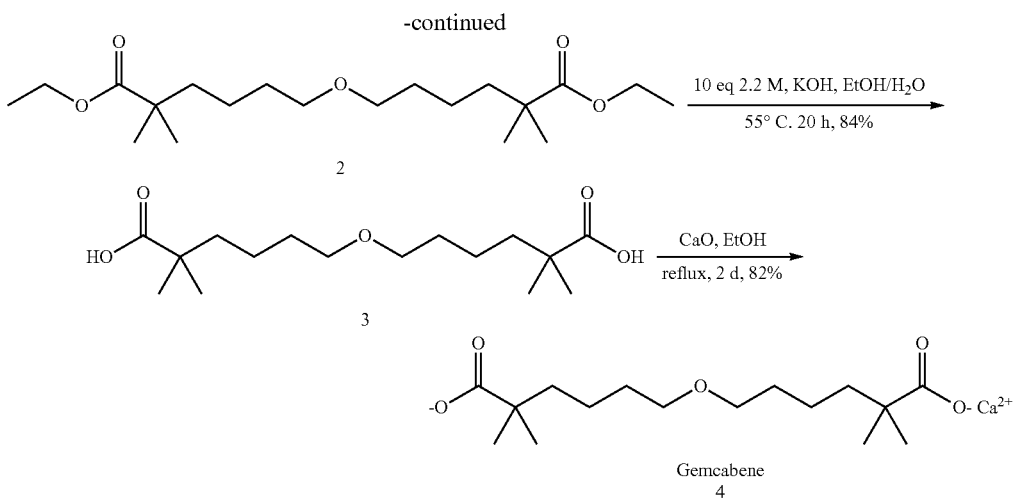

Unexpectedly, experiments using 4-chloro- and 4-bromobutyl ethers did not undergo α-alkylation of ethyl isobutyrate to produce diester 2. No evidence of a coupling product was found using 4-chlorobutyl ether as a starting material (Scheme 9).

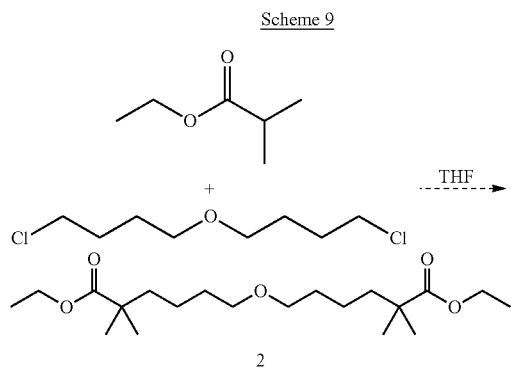

The use of 4-bromobutyl ether as a starting material resulted in the formation of diester 2, but with different reaction kinetics (Scheme 10).

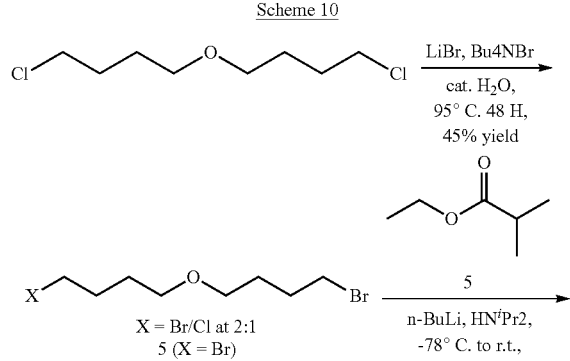

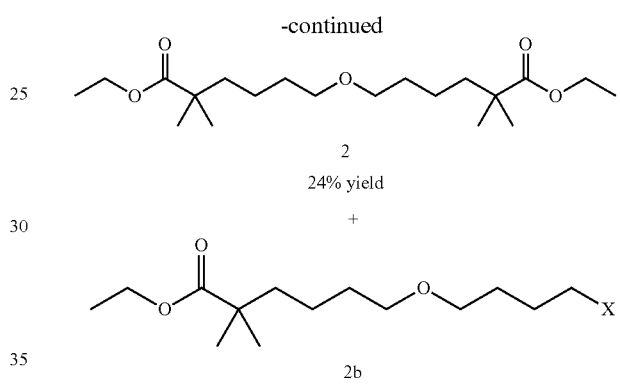

Reformatsky Approach:

Gemcabene may be prepared using a Reformatsky coupling reaction between ethyl 2-bromoisobutyrate and 4-chalobutyl ethers (Scheme 11) under various conditions. These conditions include various solvents (such as THF, methyl-t-butyl ether, and ethyl ether), various types of zinc (zinc powder with catalytic amounts of iodine or chlorotrimethylsilane or highly active Rieke® zinc), and various reaction temperatures between 0° C. to 70° C.

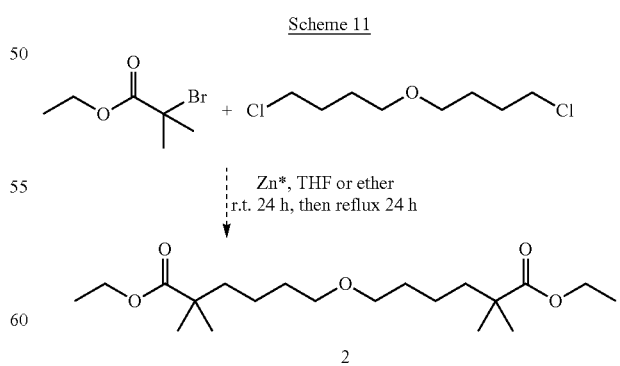

Acid-Catalyzed Ether Synthesis:

Gemcabene may be synthesized by dimerization of alcohols, such as alcohol 7 below, using the by the reaction pathway described in Scheme 12. Alcohol 7 was prepared in two steps by alkylation of benzyl protected 4-bromobutanol with an alkyl isobutyrate, followed by hydrogenation.

Scheme 12

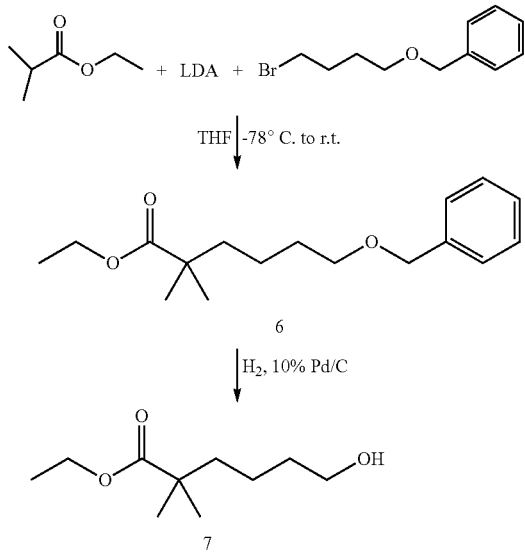

Dimerization of alcohol 7 in the presence of various acid catalysts, such as sulfuric acid or nalfion NR50 (acidic resin), in organic solvents, such as ethers or hydrocarbons, may produce gemcabene. This process may result in a complex mixture of products formed due to trans-esterification (Scheme 13).

Scheme 13

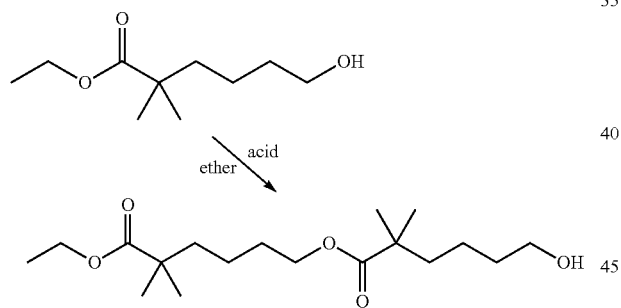

Williamson Ether Synthesis:

Another representative example of a process for preparing gemcabene is shown in the Willaimson ether synthesis in Scheme 14. Alcohol 7 was treated with sodium hydride in the presence of corresponding bromide 8. Bromide 8 was prepared by alkylating 1,4-dibromobutane with ethyl isobutyrate.

Scheme 14

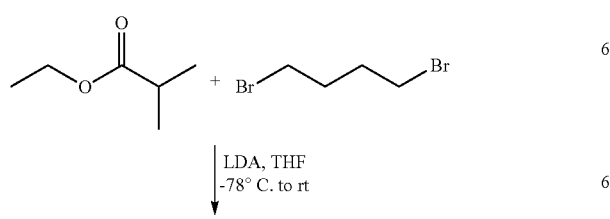

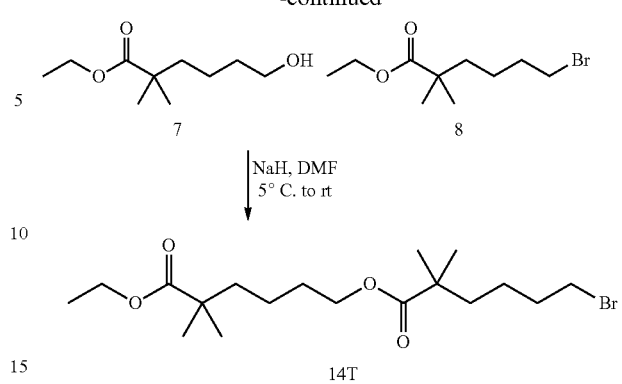

If trans-esterification occurs instead of the expected displacement reaction, the bromide 8 may be converted to the iodide before proceeding with the reaction.

To reduce the trans-esterification products and produce higher yield of the desired products, the ethyl esters may be replaced with sterically-hindered esters, such as, but not limited to, t-butyl esters. A representative example of this process is shown in Scheme 15. In this example, hydrolysis of intermediate 6 to form acid 9, followed by t-butylation in the presence of, for example, isourea 10, produces the t-butyl ester. The protected t-butyl ester 11 can be hydrogenated to afford alcohol 12 (Scheme 15) in quantitative yield.

Scheme 15

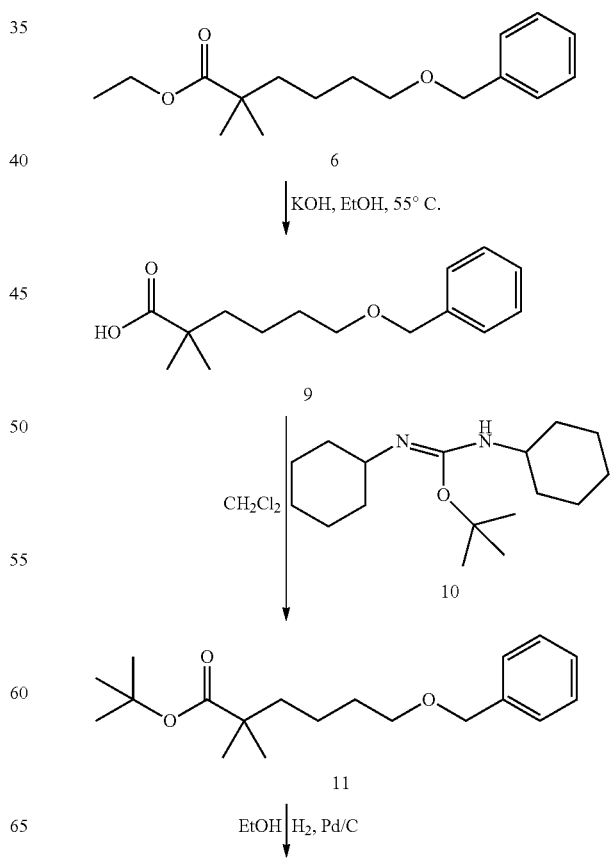

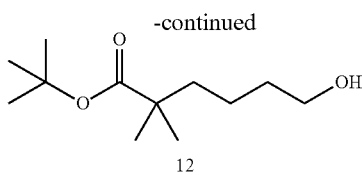

12

The corresponding bromide 13 may be prepared by alkylation of 1,4-dibromobutane with t-butyl isobutyrate. The t-butyl isobutyrate may be prepared by trans-esterification of methyl isobutyrate using sodium tert-butoxide in 51% yield according to the literature procedure (Scheme 16).

Scheme 16

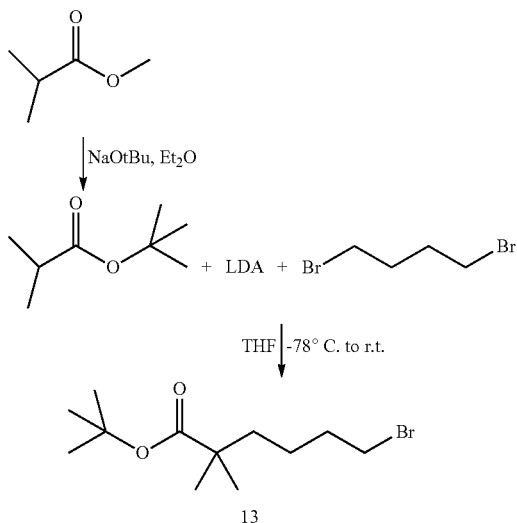

Alcohol 12 was reacted in with bromide 13 in the presence of hydrating agents, such as, but not limited to sodium hydride, in aprotic dipolar solvents, such as, but not limited to, DMF. In this representative example, gemcabene di-t-butyl ester was obtained by reacting bromide 13 with alcohol 12 in the presence of sodium hydride and DMF at 5° C., followed by warming to room temperature and stirring for 20 hours (Scheme 17).

Scheme 17

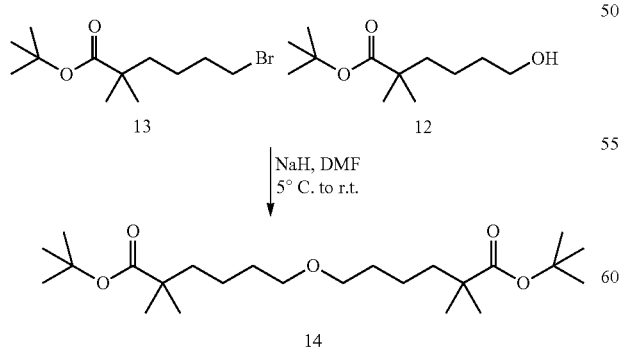

Unexpectedly, there was no indication of the trans-esterification products. Some unreacted alcohol 12 and bromide 13 were present in the crude NMR, along with some elimination product from the bromide. However, yields and conversions improved with longer reaction times and when using more than 1 equivalent of sodium hydride and bromide.

Bromide 13 was converted to the iodide by refluxing with sodium iodide in acetone. Further, iodide 15 was reacted with alcohol 12, as described in Scheme 18.

Scheme 18

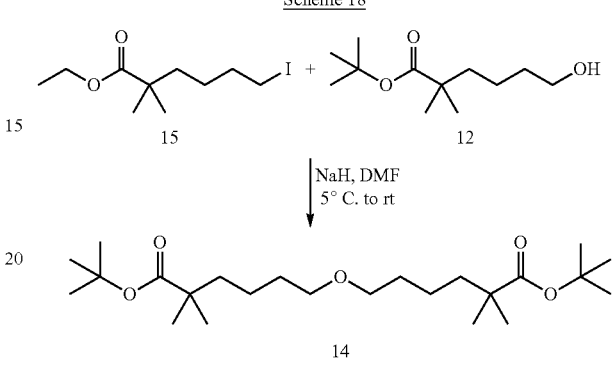

The experiment produced slightly higher yield than the bromide. Once again, no trans-esterification side products were present in the crude material. The elimination byproduct was present in higher amounts. The remainder was unreacted alcohol 12 and a trace of the iodide 15. The gemcabene t-butyl diester was converted to gemcabene diacid 3 with 10% TFA in dichloromethane.

Alkylation Method: Other α,ω-Dicarboxylic Acid-Terminated Dialkane Ethers

Synthesis of 6,6'-oxybis(2-methyl-2-(p-tolyl)hexanoic acid)

As shown in Scheme 19, the alkylation process of Scheme 8 in alkylation method may be used to produce other α,ω-dicarboxylic acid-terminated dialkane ethers, such as 6,6'-oxybis(2-methyl-2-(p-tolyl)hexanoic acid) 18. Ethyl p-tolylacetate was α-methylated with iodomethane in the presence of LDA to give the ester 16, followed by α-alkylation with 4-iodobutyl ether with LDA to give the diester 17. The dicarboxylic acid 18 was obtained by saponification of 7 with aqueous KOH in ethanol.

Scheme 19

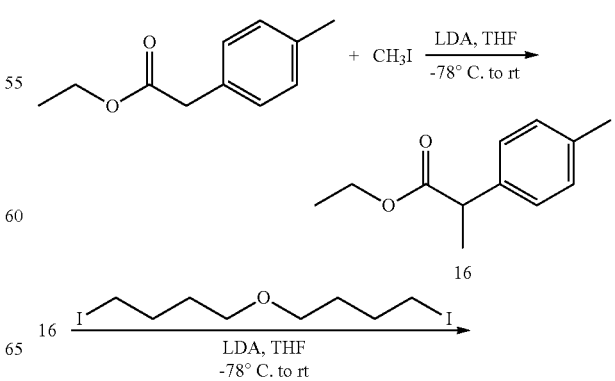

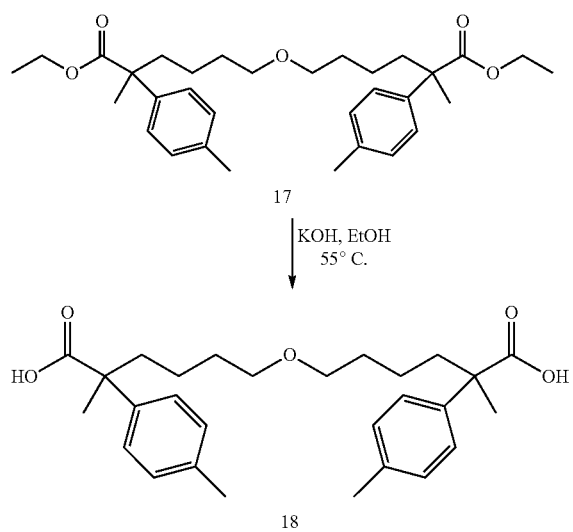

Synthesis of the 5-5, 5-4, 4-3 Analogs of Gemcabene Diethyl Ester

Three analogs of gemcabene diethyl ester (compounds 19, 20, 21 in Scheme 20) were prepared by the alkylation method using the appropriate dibromide compounds.

Scheme 20

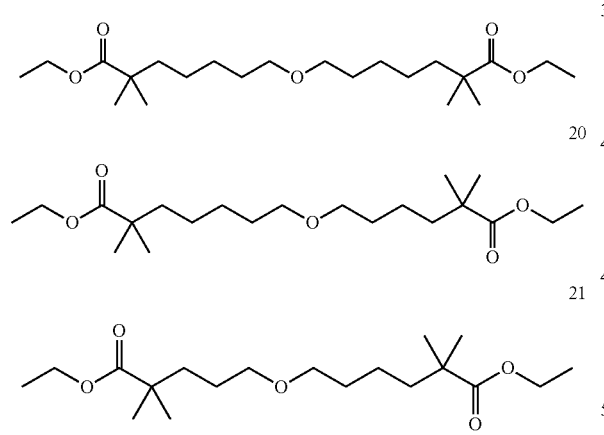

Each analog was prepared in the same fashion, altering only the dibromide compounds. A representative procedure for preparing compound 21 is shown in Scheme 17.

Scheme 21

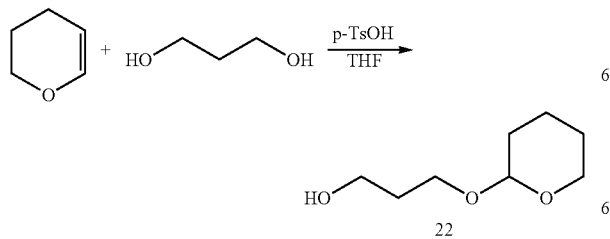

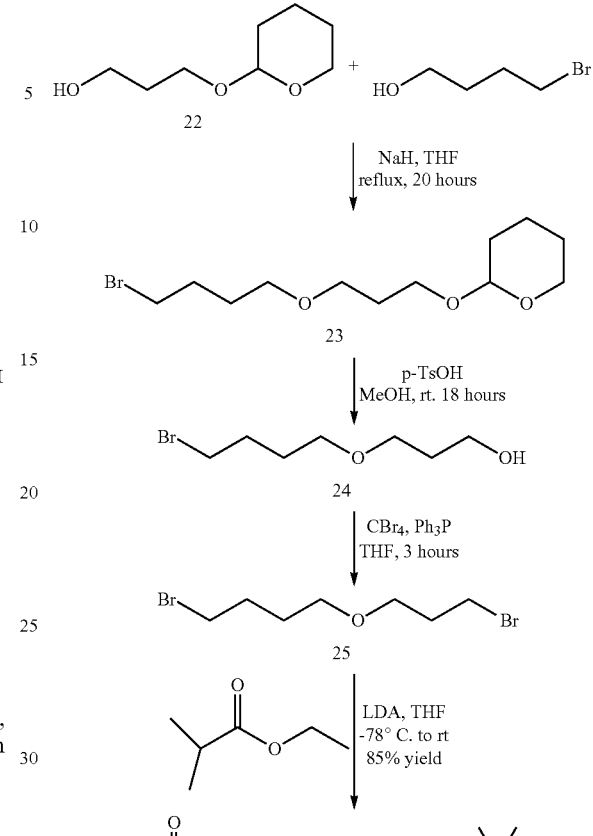

In the representative example for producing analog 21, propane diol was protected with a THP group to prepare protected alcohol 22. The protected alcohol was reacted with 1,4-dibromobutane in the presence of sodium hydride to prepare bromide 23 after reflux for 20 hours in THF. A significant amount of unreacted alcohol 22 was recovered. Running the reaction in DMF may result in an increased yield. The THP group present in bromide 23 was removed by stirring in methanol with p-toluenesulfonic acid to prepare alcohol 24. The alcohol was converted to the bromide by treatment with carbon tetrabromide and triphenylphosphine to generate the dibromide 25 in 91% yield. Once the dibromide was prepared, the alkylation with ethyl isobutyrate was conducted in the same fashion as with gemcabene in Scheme 4. Ethyl isobutyrate was deprotonated with LDA at −78° C. followed by the addition of dibromide 26, and the reaction was subsequently warmed to room temperature to provide diester 21. The procedures were repeated for compounds 19 and 20. In the case of compound 19, the alkylation with dibromide 26 (Scheme 22) provided diester 19.

Scheme 22

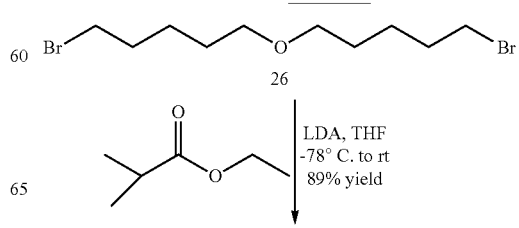

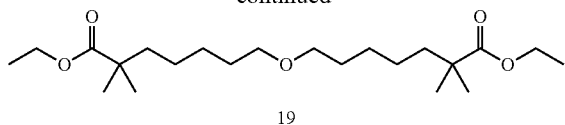

19

A comparable but slightly lower yield was seen in the alkylation with ethyl isobutyrate to prepare analog 20. For each analog, the alkylation produced the desired analogs in favorable yields.

SYNTHETIC EXAMPLES

Example 1: Gemcabene calcium prepared from ethyl isobutyrate according to Scheme 23

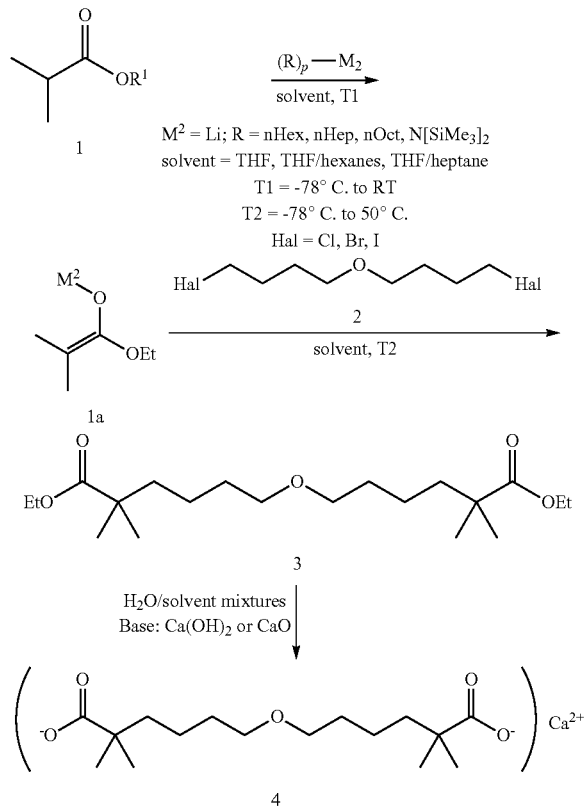

In the first step of the reaction, ethyl isobutyrate is deprotonated in the presence of a suitable non-pyrophoric lithium derivative, such as n-hexyllithium, n-heptyllithium, and n-octyllithium. The reaction is performed by either the addition of the halo-ester of formula (6) to the lithiation agent in a suitable solvent, or, conversely, by addition of the lithiation agent to the halo-ester solution in a suitable solvent. To an ethyl isobutyrate solution in a suitable organic solvent is added under stirring approximately 1 to approximately 2.2 eq of the lithium derivative at approximately 2.5 M concentration under an inert atmosphere such as nitrogen or argo gas at a rate of approximately 1.5 moles per hour. The solution is maintained at a constant temperature within the range of approximately −78° C. to approximately −10° C. Optionally, the base is diluted in a suitable organic solvent before addition. Suitable organic solvents include, but are not limited to, dichloromethane, diethyl ether, tetrahydrofuran, 2-methytetrahydrofuran, dimethylformamide, dimethyl sulfoxide, benzene, toluene, xylene, hydrocarbon solvents (such as pentane, hexane, and heptane), and mixtures thereof. After addition of the base, the reaction mixture is allowed to stir for approximately 1 hr to approximately 12 hr. Then bis(halobutyl)ether, dissolved in a suitable solvent, is added, preferably at a rate such that the reaction-mixture temperature remains within approximately one to five degrees of the initial reaction-mixture temperature. A suitable bis(halobutyl)ether is a bis(chloro), bis(bromo), or a bis(iodo) ether. These compounds are commercially available, for example, from FCH Group Reagents for Synthesis, or can be prepared as described, for instance, in Mueller R. et al., *J. Med. Chem.* 2004, 47, 5183-5197. After completion of the addition, the reaction-mixture temperature can be adjusted to within a temperature range of approximately −20° C. to approximately RT, preferably to approximately RT. The reaction mixture is allowed to stir until the reaction is substantially complete, as determined using an appropriated analytical method, such as thin-layer chromatography or high-performance liquid chromatography. Then, the reaction mixture is quenched, and the diester compound of formula (7) is isolated by workup. Gemcabene is then synthesized by reacting the diester of formula (7) with a metal salt, base, or oxide according to the protocol described above for the formation of the α,ω-dicarboxylic acid-terminated dialkane ether salt of formula (IV).

Example 2: Gemcabene prepared from ethyl α-bromoisobutyrate of formula (10) according to Scheme 24

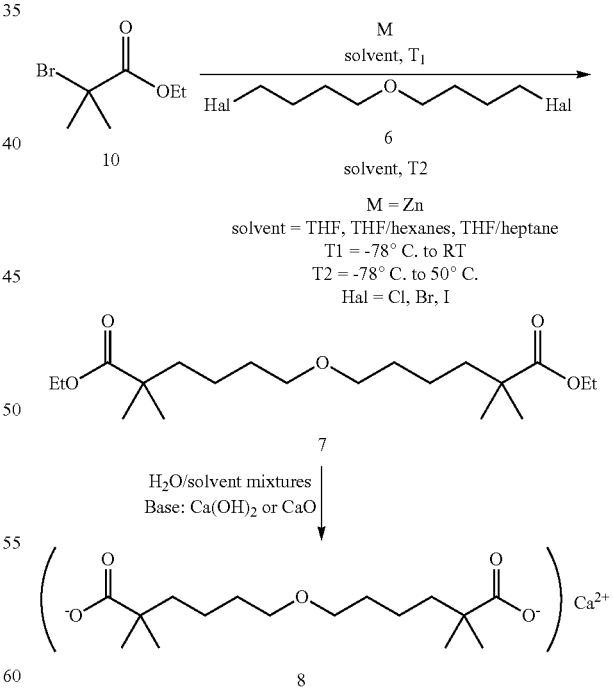

In a typical procedure, ethyl α-bromoisobutyrate of formula (10) is treated at 0° C. with 1 eq of powdered zinc under an inert atmosphere, such as nitrogen or argon gas. The mixture is stirred at approximately 0° C. to approximately 10° C. until nearly all the zinc has reacted (approximately 3 hr). Alternatively, iodine is added to initiate the reaction. Bis(halobutyl)ether of formula (6) (0.5 eq), is added dropwise to the flask over 1 hr, and the mixture is allowed to warm to 25° C. over several hours, after which time the mixture is heated at 50° C. for 1 hr and cooled. Aqueous ammonium chloride is added to the mixture, and the aqueous layer is extracted with an organic solvent, dried over a drying agent, and evaporated to give the crude product.

Example 3: Diethyl 7,7'-oxybis(2,2-dimethylheptanoate)

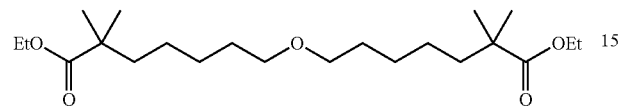

Diethyl 7,7'-oxybis(2,2-dimethylheptanoate) may be prepared according to the processes of Examples 1 or 2 above, wherein the α,ω-halo-terminated dialkane ether of formula (2) is bis(halopentyl)ether.

Example 4: Ethyl 7-((6-ethoxy-5,5-dimethyl-6-oxohexyl)oxy)-2,2-dimethylheptanoate

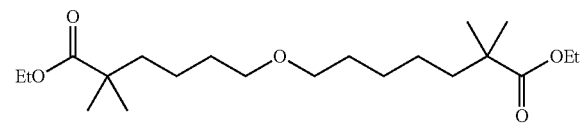 [SMILES: CCOC(=O)C(C)(C)CCCCCOCCCCC(C)(C)C(=O)OCC]

Ethyl 7-((6-ethoxy-5,5-dimethyl-6-oxohexyl)oxy)-2,2-dimethylheptanoate may be prepared according to the processes of Examples 1 or 2 above, wherein the α,ω-halo-terminated dialkane ether of formula (2) is 1-chloro-5-(4-chlorobutoxy)pentane.

Example 5: Ethyl 6-((5-ethoxy-4,4-dimethyl-5-oxopentyl)oxy)-2,2-dimethylhexanoate

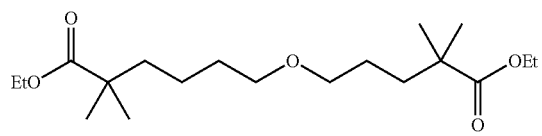 [SMILES: CCOC(=O)C(C)(C)CCCCOCCCC(C)(C)C(=O)OCC]

Ethyl 6-(5-ethoxy-4,4-dimethyl-5-oxopentyl)oxy)-2,2-dimethylhexanoate may be prepared according to the processes of Examples 1 or 2 above, wherein the α,ω-halo-terminated dialkane ether of formula (2) is 1-halo-4-(3-chloropropoxy)butane.

Example 6: Diethyl 6,6'-oxybis(2-methyl-2-(p-tolyl)hexanoate)

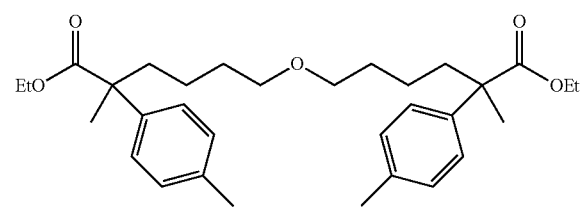 [SMILES: CCOC(=O)C(C)(CCCCOCCCCC(C)(C(=O)OCC)c1ccc(C)cc1)c1ccc(C)cc1]

Diethyl 6,6'-oxybis(2-methyl-2-(p-tolyl)hexanoate) may be prepared according to the process of Example 1, above, wherein the compound of formula (I) is ethyl 2-o-tolyl-propionate. Diethyl 6,6'-oxybis(2-methyl 2-o-tolyl-hexanoate) may also be prepared according to the process of Example 2, above, wherein the compound of formula (9) is ethyl 2-bromo-2-o-tolyl-propionate.

Example 7: 4-Iodobutyl ether (1)

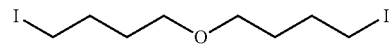

Acetone (previously dried over 4 Å molecular sieve, 200 mL) was added to a stirred mixture of 4-chlorobutyl ether (10.0 g, 50.2 mmol) and sodium iodide (24.9 g, 166 mmol, 3.3 eq.), and the mixture was heated at reflux for 48 h. The reaction mixture was cooled to room temperature and then filtered. The inorganic solid was rinsed with acetone (100 mL), and the filtrate was concentrated under reduced pressure. The residue was taken up in MTBE (200 mL). The resulting mixture was washed with water (200 mL), 2% sodium thiosulfate (200 mL), and brine (200 mL) sequentially and then concentrated under reduced pressure. The crude product was purified through a silica-gel flash chromatography eluted with heptane/ethyl acetate (40:1) to give the desired product (18.3 g, 95% yield) as a yellow oil: $^1$H NMR (300 MHz, CDCl$_3$) 3.43 (t, 4H, J=6.3 Hz), 3.22 (t, 4H, J=6.9 Hz), 1.91 (m, 4H), 1.67 (m, 4H).

Example 8: 6-(5-Ethoxycarbonyl-5-methyl-hexyloxy)-2,2-dimethyl-hexanoic acid ethyl ester (2)

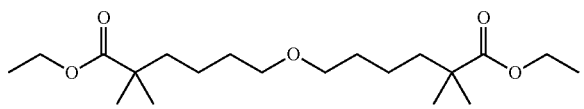 [SMILES: CCOC(=O)C(C)(C)CCCCOCCCCC(C)(C)C(=O)OCC]

To a stirred solution of diisopropylamine (1.19 g, 11.8 mmol) in anhydrous THF (20 mL) cooled in a dry ice bath was added hexyllithium (2.3 M, 5.1 mL, 11.8 mmol), and the mixture was stirred for 40 minutes. Ethyl isobutyrate (1.37 g, 11.8 mmol) was added drop-wise, and 30 minutes later 4-iodobutyl ether (1.63 g, 4.27 mmol) was added. After addition, the reaction mixture was slowly warmed to room temperature and stirred overnight. The reaction mixture was poured into cold 1 N HCl solution (50 mL) and then extracted with MTBE (3×30 mL). The combined extracts were washed with 2% sodium thiosulfate (50 mL) and brine (30 mL), dried over sodium sulfate, and concentrated under reduced pressure. The residue was purified through a silica-gel flash chromatography eluted with a gradient of heptane/ethyl acetate (40:1 to 10:1) to give the desired diester (1.40 g, 91% yield) as a colorless oil: $^1$H NMR (300 MHz, CDCl$_3$) δ 4.11 (q, 4H, J=7.2 Hz), 3.37 (t, 4H, J=6.6 Hz), 1.52 (m, 8H), 1.29 (m, 4H), 1.24 (t, 6H, J=7.2 Hz), 1.16 (s, 12H); $^{13}$C NMR (75 MHz, CDCl$_3$) δ 177.98, 70.68, 60.13, 42.11, 40.48, 30.17, 25.05, 21.59, 14.21.

Example 9: 6-(5-Carboxyl-5-methyl-hexyloxy)-2,2-dimethyl-hexanoic acid (3)

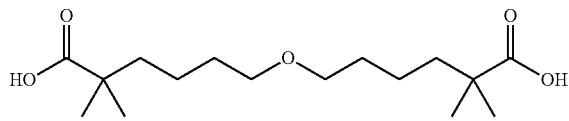 [SMILES: CC(C)(CCCCOCCCCC(C)(C)C(=O)O)C(=O)O]

To a stirred solution of 6-(5-ethoxycarbonyl-5-methylhexyloxy)-2,2-dimethyl-hexanoic acid ethyl ester (2.68 g, 7.48 mmol) in absolute ethanol (50 mL) was added aqueous KOH (2.2 M, 34 mL, 74.8 mmol), and the mixture was stirred at 55° C. for 24 h. The reaction mixture was cooled to room temperature and then concentrated under reduced pressure to remove ethanol. The remaining mixture was extracted with MTBE (50 mL), and the extract was discarded. The aqueous layer was acidified with 3 N HCl (30 mL) slowly. The resulting mixture was extracted with MTBE (3×30 mL). The combined extracts were dried over sodium sulfate and concentrated under reduced pressure. The residue was purified through a silica-gel flash chromatography eluted with heptane/ethyl acetate (from 4:1 to 2:1) to give the desired diacid (1.53 g, 84% yield) as a white solid: $^1$H NMR (300 MHz, CDCl$_3$) δ 3.37 (t, 4H, J=5.1 Hz), 1.49 (m, 8H), 1.35 (m, 4H), 1.19 (s, 12H).

Alternate synthesis from the di-tert-butyl ester:

The di-tert-butyl ester of gemcabene (0.25 g, 0.36 mmol) was dissolved in dichloromethane (5 mL) and trifluoroacetic acid (0.5 mL). The mixture was stirred at room temperature for 20 hours. After 20 hours, the solution was concentrated and dried to a constant weight under high vacuum. The experiment produced the desired diacid (105 mg, 97% yield) as a colorless solid: $^1$H NMR (300 MHz, CDCl$_3$) δ 11.23 (s, 2H), 3.37 (t, 4H, J=5.1 Hz), 1.49 (m, 8H), 1.35 (m, 4H), 1.19 (s, 12H).

Example 10: Gemcabene Calcium (4)

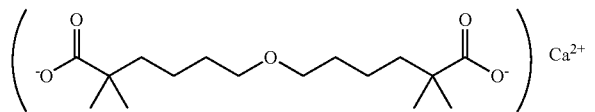

To a stirred solution of 6-(5-carboxyl-5-methyl-hexyloxy)-2,2-dimethyl-hexanoic acid (1.34 g, 4.43 mmol) in absolute ethanol (30 mL) was added CaO (0.25 g, 4.43 mmol), and the mixture was stirred at reflux for two days. The reaction mixture was cooled to room temperature, diluted with MTBE (30 mL), and then stirred for two hours. The mixture was settled for 30 minutes and then filtered. The crop (4.32 g) was dried at 80° C. for 24 h under high vacuum to give a white solid (1.29 g). To the solid was added DIUF water (0.26 g, 14.4 mmol), and the mixture was stirred at 100° C. for five hours and then dried under high vacuum at 95° C. for 1 h and then at room temperature overnight to give the desired product (1.24 g, 82% yield, 99.9% HPLC purity) as a white solid: $^1$H NMR (300 MHz, D$_2$O-TSP) δ 3.51 (t, 4H, J=6.9 Hz), 1.55 (m, 4H), 1.46 (m, 4H), 1.26 (m, 4H), 1.07 (s, 12H); $^{13}$C NMR (75 MHz, D$_2$O-1,4-dioxane) δ 188.05, 70.51, 43.36, 40.71, 29.25, 25.43, 21.27.

Example 11: 4-Bromobutyl ether (5)

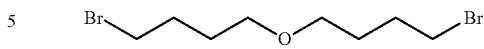

A sealed tube was charged with a magnetic stirring bar, lithium bromide (2.21 g, 25.5 mmol), tetrabutylammonium bromide (0.82 g, 2.55 mmol, 0.1 eq.), water (0.022 g, 1.22 mmol) and 4-chlorobutyl ether (1.99 g, 10.0 mmol). The mixture was stirred at 95° C. for 48 h. The mixture was diluted with heptane (30 ml) and water (20 mL), and the layers were separated. The organic layer was washed with brine (20 mL), dried over anhydrous sodium sulfate, and concentrated under reduced pressure. The residue was purified through a silica-gel chromatography eluted with heptane/ethyl acetate (40:1) to give 4-bromobutyl ether (1.29 g, 45% yield, containing ~30% 4-bromobutyl 4-chlorobutyl ether) as a colorless oil: $^1$H NMR (300 MHz, CDCl$_3$) δ 3.44 (t, 8H, J=6.0 Hz), 1.97 (m, 4H), 1.71 (m, 4H).

Example 12: 6-Benzyloxy-2,2-dimethylhexanoic acid ethyl ester (6)

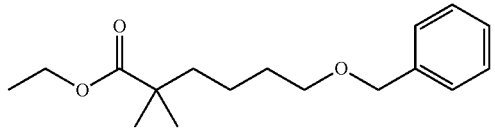 [SMILES: CCOC(=O)C(C)(C)CCCCOCc1ccccc1]

Ethyl isobutyrate (4.0 g, 34.4 mmol) was dissolved in dry THF (50 mL) under argon. The flask was cooled in a dry ice/acetone bath, and 2M LDA (21 ml, 42 mmol) was added drop-wise over 5-10 minutes. The solution stirred for 30 minutes, and benzyl 4-bromobutyl ether (8.0 g, 32.9 mmol) was added. The solution slowly warmed to room temperature and stirred overnight. After 18 hours at room temperature, water (50 ml) was added along with ethyl acetate (50 mL). The layers were separated, and the ethyl acetate layer was extracted with 5% hydrochloric acid solution (50 ml), followed by brine (50 mL). The ethyl acetate extract was dried over sodium sulfate, filtered, and concentrated. The remaining oil was purified on silica gel (200 g), eluting with 1:20 ethyl acetate/heptanes. The experiment generated 8.6 g (95% yield) of 6-benzyloxy-2,2-dimethylhexanoic acid ethyl ester as a clear oil. $^1$H NMR (300 MHz, CDCl$_3$) δ 7.40-7.25 (m, 5H), 4.51 (s, 2H), 4.12 (q, 2H, J=7.2 Hz), 3.48 (t, 2H, J=6.6 Hz), 1.64-1.53 (m, 4H), 1.39-1.32 (m, 5H), 1.17 (s, 6H).

Example 13: 6-Hydroxy-2,2-dimethylhexanoic acid ethyl ester (7)

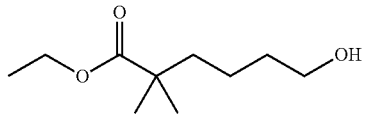

6-Benzyloxy-2,2-dimethylhexanoic acid ethyl ester (9.6 g, 34.7 mmol) was dissolved in ethyl acetate (100 mL) and added to 20% palladium on carbon (0.8 g). The mixture was hydrogenated at 40 psi hydrogen in a Parr apparatus for 24 h. The mixture was then purged with nitrogen and filtered through a pad of celite and concentrated. The experiment produced 6-hydroxy-2,2-dimethyl-hexanoic acid ethyl ester (5.8 g, 88% yield) as a clear oil. $^1$H NMR (300 MHz, CDCl$_3$) δ 4.10 (q, 2H, J=7.2 Hz), 3.57 (t, 2H, J=5.4 Hz), 1.51-1.45 (m, 4H), 1.33-1.23 (m, 5H), 1.13 (s, 6H).

Example 14: 6-bromo-2,2-dimethylhexanoic acid ethyl ester (8)

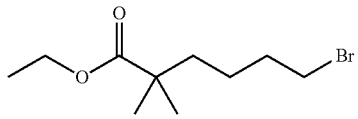

Ethyl isobutyrate (10.0 g, 86.0 mmol) was dissolved in dry THF (100 mL) under argon. The flask was cooled in a dry ice/acetone bath, and 2M LDA (51.8 ml, 103.6 mmol) was added drop-wise over 5-10 minutes. The solution stirred for 30 minutes, and 1,4-dibromobutane (22.3 g, 103 mmol) was added. The solution slowly warmed to room temperature and stirred overnight. After 18 h at room temperature, water (100 ml) was added along with ethyl acetate (100 mL). The layers were separated, and the ethyl acetate layer was extracted with 5% hydrochloric acid solution (100 ml) followed by brine (100 mL). The ethyl acetate extract was dried over sodium sulfate, filtered, and concentrated. The remaining oil was purified twice on silica gel (200 g), eluting with 1:10 ethyl acetate/heptane. The experiment generated 12.2 g (56% yield) of 6-bromo-2,2-dimethylhexanoic acid ethyl ester as a clear oil. $^1$H NMR (300 MHz, CDCl$_3$) δ 4.14 (q, 2H, J=7.2 Hz), 3.52 (t, 2H, J=56.9 Hz), 1.88-1.82 (m, 2H), 1.58-1.36 (m, 2H), 1.36 (t, 3H, J=7.2 Hz), 1.18 (s, 6H).

Example 15: 6-Benzyloxy-2,2-dimethylhexanoic acid (9)

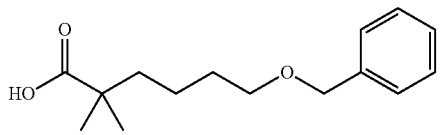 [SMILES: CC(C)(CCCCOCc1ccccc1)C(=O)O]

6-Benzyloxy-2,2-dimethylhexanoic acid ethyl ester (7.40 g, 26.6 mmol) was dissolved in ethanol (120 mL) with potassium hydroxide (7.40 g, 132 mmol) and water (40 mL). The solution was heated to 50-60° C. overnight. After 18 h, the solution was cooled to room temperature and concentrated to remove ethanol. Water (150 mL) was added, and the solution was extracted with heptanes (100 mL). The layers were separated and the aqueous layer was acidified to pH=2 with concentrated hydrochloric acid. The product was extracted twice with ethyl acetate (50 mL). The combined ethyl acetate extracts were washed with brine (50 mL), dried over sodium sulfate, filtered, and concentrated. The experiment produced 4.72 g (72% yield) of 6-benzyloxy-2,2-dimethylhexanoic acid as a white solid. $^1$H NMR (300 MHz, CDCl$_3$) δ 7.35-7.25 (m, 5H), 4.50 (s, 2H), 3.48 (t, 2H, J=6.6 Hz), 1.64-1.53 (m, 4H), 1.40-1.37 (m, 2H), 1.19 (s, 6H).

Example 16: 6-Benzyloxy-2,2-dimethylhexanoic acid tert-butyl ester (11)

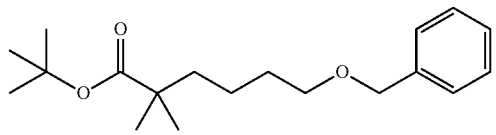 [SMILES: CC(C)(C)OC(=O)C(C)(C)CCCCOCc1ccccc1]

6-benzyloxy-2,2-dimethylhexanoic acid (2.50 g, 9.98 mmol) was dissolved in dichloromethane (50 mL) with t-butyl-dicyclohexyl isourea (4.50 g, 16.05 mmol). The mixture stirred for 72 h at room temperature under argon. After 72 h, the mixture was filtered to remove DCU. The filtrate was washed with saturated sodium bicarbonate solution (50 mL). The dichloromethane was dried over sodium sulfate, filtered, and concentrated. The remaining oil was filtered through silica gel (30 g) with 10% ethyl acetate/heptanes. The experiment generated 2.20 g (72% yield of 6-Benzyloxy-2,2-dimethylhexanoic acid tert-butyl ester as a clear oil. $^1$H NMR (300 MHz, CDCl$_3$) δ 7.35-7.25 (m, 5H), 4.50 (s, 2H), 3.48 (t, 2H, J=6.3 Hz), 1.62-1.49 (m, 4H), 1.42 (s, 9H), 1.40-1.37 (m, 2H), 1.11 (s, 6H).

Example 17: 6-Hydroxy-2,2-dimethylhexanoic acid t-butyl ester (12)

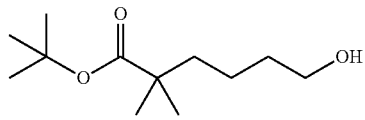

6-Benzyloxy-2,2-dimethylhexanoic acid tert-butyl ester (2.20 g, 7.18 mmol) was dissolved in ethyl acetate (40 mL) and added to 10% palladium on carbon (1.35 g). The mixture was hydrogenated at 40 psi hydrogen in a Parr apparatus for 48 h. The mixture was then purged with nitrogen and filtered through a pad of celite and concentrated. The experiment produced 6-hydroxy-2,2-dimethyl-hexanoic acid t-butyl ester (1.60 g, 100% yield) as a clear oil. $^1$H NMR (300 MHz, CDCl$_3$) δ 3.65 (t, 2H, J=6.6 Hz), 1.58-1.50 (m, 4H), 1.43 (s, 9H), 1.39-1.30 (m, 2H), 1.12 (s, 6H).

Example 18: 6-Bromo-2,2-dimethylhexanoic acid tert-butyl ester (13)

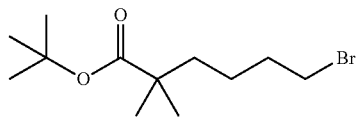

t-Butyl isobutyrate (1.90 g, 13.1 mmol) was dissolved in dry THF (40 mL) under argon. The flask was cooled in a dry ice/acetone bath, and 2M LDA (7.2 mL, 14.4 mmol) was added drop-wise over 5-10 minutes. The solution stirred for 30 minutes, and 1,4-dibromobutane (8.0 g, 37 mmol) was added. The solution slowly warmed to room temperature and stirred overnight. After 18 h at room temperature, water (50 ml) was added along with ethyl acetate (50 mL). The layers were separated, and the ethyl acetate layer was extracted with 5% hydrochloric acid solution (50 ml) followed by brine (50 mL). The ethyl acetate extract was dried over sodium sulfate, filtered, and concentrated. The remaining oil was purified twice on silica gel (30 g), eluting with 1:20 ethyl acetate/heptane. The experiment generated 1.0 g (28% yield) of 6-bromo-2,2-dimethylhexanoic acid t-butyl ester as a clear oil. $^1$H NMR (300 MHz, CDCl$_3$) δ 3.42 (t, 2H, J=6.9 Hz), 1.88-1.83 (m, 2H), 1.58-1.36 (m, 2H), 1.47 (s, 9H), 1.14 (s, 6H).

Example 19: 6-(5-tert-Butoxycarbonyl-5-methyl-hexyloxy)-2,2-dimethyl-hexanoic acid tert-butyl ester (14)

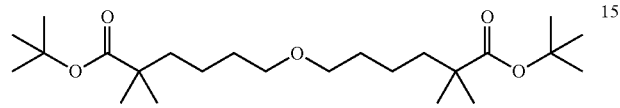

Sodium hydride (60%, 50 mg, 1.25 mmol) was mixed with DMF (5 mL) under argon. The flask was cooled in a water/ice batch, and 6-hydroxy-2,2-dimethylhexanoic acid t-butyl ester (0.26 g, 1.20 mmol) was added. The mixture was stirred for 10-20 minutes at 5° C. when 6-bromo-2,2-dimethylhexanoic acid t-butyl ester (0.35 g, 1.25 mmol) in DMF (1.0 mL) was added. The mixture was slowly warmed to room temperature and stirred overnight under argon. After 20 h at room temperature, water (20 mL) was added, and the product was extracted with diethyl ether (2×20 mL). The combined ether extracts were washed with water (20 mL), dried over sodium sulfate, filtered, and concentrated. The remaining oil was purified on silica gel eluting with 10% ethyl acetate/heptanes. The experiment produced the d-t-butyl ester of gemcabene (0.17 g, 34% yield) as a clear oil. $^1$H NMR (300 MHz, CDCl$_3$) δ 3.38 (t, 4H, J=6.9 Hz), 1.55-1.45 (m, 8H), 1.43 (s, 18H), 1.35-1.25 (m, 4H), 1.11 (s, 12H).

Alternate Procedure:

Sodium hydride (60%, 50 mg, 1.25 mmol) was mixed with DMF (5 mL) under argon. The flask was cooled in a water/ice batch, and 6-hydroxy-2,2-dimethylhexanoic acid t-butyl ester (0.26 g, 1.20 mmol) was added. The mixture was stirred for 30-40 minutes at 5° C. when 6-iodo-2,2-dimethylhexanoic acid t-butyl ester (0.50 g, 1.53 mmol) was added. The mixture was slowly warmed to room temperature and stirred overnight under argon. After 20 h at room temperature, water (20 mL) was added, and the product was extracted with diethyl ether (2×20 mL). The combined ether extracts were washed with water (20 mL), dried over sodium sulfate, filtered, and concentrated. The remaining oil was purified on silica gel eluting with 10% ethyl acetate/heptanes. The experiment produced the d-t-butyl ester of gemcabene (0.20 g, 40% yield) as a clear oil. $^1$H NMR (300 MHz, CDCl$_3$) δ 3.38 (t, 4H, J=6.9 Hz), 1.55-1.45 (m, 8H), 1.43 (s, 18H), 1.35-1.25 (m, 4H), 1.11 (s, 12H). HRMS (ESI): [M+NH$_4$]$^+$=432.3684. found 432.3696.

Example 20: 6-Iodo-2,2-dimethylhexanoic acid t-butyl ester (15)

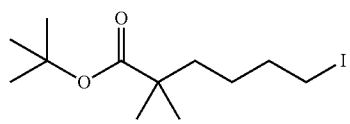

6-Bromo-2,2-dimethylhexanoic acid tert-butyl ester (0.66 g, 2.36 mmol) was dissolved in acetone (30 mL) with sodium iodide (0.90 g, 6.0 mmol). The mixture was heated to reflux for 2 h under argon. The mixture was cooled to room temperature, filtered, and concentrated. Heptane (30 mL) was added along with water (30 mL). The layers were separated, and the heptanes was dried over sodium sulfate, filtered, and concentrated. The experiment produced 6-iodo-2,2-dimethylhexanoic acid t-butyl ester (0.71 g, 92% yield) as a colorless oil. $^1$H NMR (300 MHz, CDCl$_3$) δ 3.19 (t, 2H, J=6.6 Hz), 1.86-1.76 (m, 2H), 1.51-1.34 (m, 2H), 1.45 (s, 9H), 1.13 (s, 6H).

Example 21: Ethyl 2-p-tolylpropionate (16)

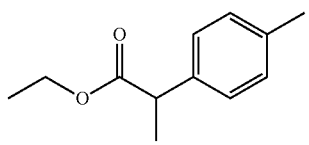

To a stirred solution of ethyl p-tolylacetate (1.78 g, 10.0 mmol) in anhydrous THF (15 mL) cooled in a dry ice bath was added lithium diisopropylamide (2 M, 5.0 mL, 10 mmol) drop-wise. After the mixture was stirred for 30 minutes, iodomethane (1.42 g, 10.0 mmol) was added drop-wise. After addition, the reaction mixture continued to be stirred at −78° C. for 30 minutes and then at room temperature overnight. The reaction was quenched with cold 1 N HCl solution (20 mL), and the resulting mixture was extracted with MTBE (2×30 mL). The combined extracts were washed with 2% sodium thiosulfate (50 mL), brine (30 mL), dried over anhydrous sodium sulfate, and concentrated under reduced pressure. The crude product was purified through a silica-gel flash chromatography eluted with heptane/ethyl acetate (60:1) to give the desired product (1.37 g, 71% yield) as a light yellow oil: $^1$H NMR (300 MHz, CDCl$_3$) δ 7.19 (d, 2H, J=7.8 Hz), 7.13 (d, 2H, J=7.8 Hz), 4.11 (m, 2H), 3.67 (q, 1H, J=7.2 Hz), 2.33 (s, 3H), 1.47 (d, 3H, J=7.2 Hz), 1.20 (t, 3H, J=7.2 Hz).

Example 22: Diethyl 6,6'-oxybis(2-methyl-2-(p-tolyl)hexanoate) (17)

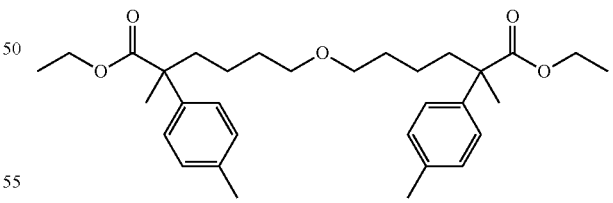

To a stirred solution of diisopropylamine (0.68 g, 6.8 mmol) in anhydrous THF (15 mL) cooled in a dry ice bath was added hexyllithium (2.3 M, 2.9 mL, 6.8 mmol), and the mixture was stirred for 40 minutes. Ethyl 2-p-tolylpropionate (1.30 g, 6.76 mmol) was added drop-wise; 30 minutes later, followed by addition of 4-iodobutyl ether (0.93 g, 2.5 mmol). After addition, the reaction mixture was slowly warmed to room temperature and stirred for three days. The reaction mixture was poured into cold 1 N HCl solution (30 mL) and then extracted with MTBE (3×30 mL). The combined extracts were washed with 2% sodium thiosulfate (50 mL) and brine (50 mL), dried over sodium sulfate, and concentrated under reduced pressure. The residue was purified through a silica-gel flash chromatography eluted with a gradient of heptane/ethyl acetate (40:1 to 10:1) to give the desired diester (1.10 g, 89% yield) as a light yellow oil: $^1$H NMR (300 MHz, CDCl$_3$) δ 7.19 (d, 4H, J=8.4 Hz), 7.11 (d, 4H, J=8.4 Hz), 4.11 (q, 4H, J=7.2 Hz), 3.34 (t, 4H, J=6.6 Hz), 2.32 (s, 6H), 2.03 (m, 2H), 1.87 (m, 2H), 1.54 (m, 4H), 1.51 (s, 6H), 1.22 (m, 4H), 1.18 (t, 6H, J=7.2 Hz); $^{13}$C NMR (75 MHz, CDCl$_3$) δ 176.32, 141.10, 136.06, 128.98, 125.82, 70.62, 60.62, 49.80, 39.08, 30.21, 22.70, 21.44, 20.90, 14.08.

Example 23: 6,6'-Oxybis(2-methyl-2-(p-tolyl)hexanoic acid) (18)

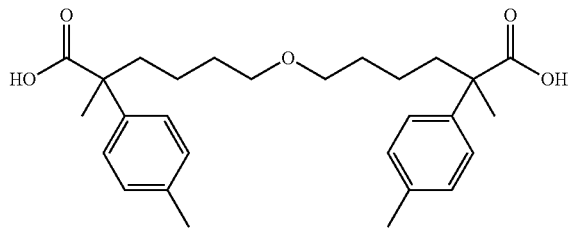 [SMILES: Cc1ccc(C(C)(CCCCOCCCCC(C)(C(=O)O)c2ccc(C)cc2)C(=O)O)cc1]

To a stirred solution of diester diethyl 6,6'-oxybis(2-methyl-2-(p-tolyl)hexanoate) (1.07 g, 2.11 mmol) in absolute ethanol (20 mL) was added aqueous KOH (2.2 M, 9.6 mL, 21 mmol), and the mixture was stirred at 55° C. for 48 h. The reaction mixture was cooled to room temperature and then concentrated under reduced pressure to remove ethanol. The remaining mixture was diluted with water (10 mL) and then acidified with 3 N HCl (10 mL) slowly. The resulting cloudy mixture was extracted with MTBE (3×30 mL). The combined extracts were dried over sodium sulfate and concentrated under reduced pressure. The residue was purified through a silica-gel flash chromatography eluted with heptane/ethyl acetate (from 6:1 to 2:1), followed by lyophilization to give the desired dicarboxylic acid (0.56 g, 64% yield, 98.7% HPLC purity) as a colorless oil: $^1$H NMR (300 MHz, CDCl$_3$) δ 7.24 (m, 4H), 7.13 (m, 4H), 3.50 (m, 1H), 3.40 (m, 2H), 3.32 (m, 1H), 2.33 (s, 3H), 2.31 (s, 3H), 2.16 (m, 2H), 1.83 (m, 2H), 1.58 (m, 4H), 1.50 (s, 3H), 1.46 (s, 3H), 1.40 (m, 4H); $^{13}$C NMR (75 MHz, CDCl$_3$) δ 182.60, 182.39, 141.25, 141.04, 136.43, 129.10, 125.92, 125.81, 69.99, 69.96, 50.38, 50.31, 38.95, 38.39, 30.25, 30.23, 24.09, 23.71, 22.06, 20.90.

Example 24: 3-(Tetrahydropyran-2-yloxy)-propan-1-ol (22)

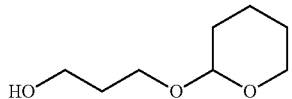 [SMILES: OCCCOC1CCCCO1]

1,3-Propanediol (34.2 g, 0.45 mol) and p-toluenesulfonic acid monohydrate (0.66 g, 3.47 mmol) were dissolved in a mixture of THF (100 mL) and dichloromethane (30 mL). The flask was cooled in an ice bath, and 3,4-dihydropyran (12.0 g, 0.14 mol) was added drop-wise over 20-30 minutes. After 2 hours of stirring, the ice bath was removed, and the reaction was stirred at room temperature for 2 hours. After 2 hours, the reaction was slowly poured into water (500 mL) that contained potassium carbonate (12 g). The product was extracted with ethyl acetate (2×250 mL). The combined ethyl acetate extracts were washed with water (2×250 mL) and brine (100 mL), dried over sodium sulfate, filtered, and concentrated. The crude oil was purified by column chromatography on silica gel (250 g), eluting with 3:1 heptane/ethyl acetate. The procedure generated 7.24 g (32% yield) of 3-(tetrahydropyran-2-yloxy)-propan-1-ol, as a colorless oil. $^1$H NMR (300 MHz, CDCl$_3$) δ 4.59 (t, 1H, J=2.4 Hz), 3.98-3.78 (m, 4H), 3.77-3.50 (m, 2H), 2.37 (t, 1H, J=5.7 Hz), 1.90-1.70 (m, 4H), 1.60-1.53 (m, 4H).

Example 25: 2-[3-(4-Bromobutoxy)-propoxy]-tetrahydropyran (23)

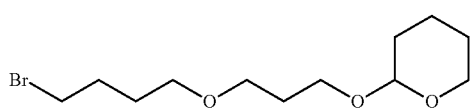 [SMILES: BrCCCCOCCCOC1CCCCO1]

3-(Tetrahydropyran-2-yloxy)-propan-1-ol (7.24 g, 45.2 mmol) was dissolved in dry THF (120 mL) under argon with 60% sodium hydride (3.6 g, 54.2 mmol). The mixture was stirred for 30 minutes at room temperature. 1,4-dibromobutane (12.0 g, 55.5 mmol) was added and the mixture was heated to reflux for 22 h. After 22 h, the solution was cooled to room temperature and poured into water (150 mL) and extracted with ethyl acetate (100 mL). The ethyl acetate was dried over sodium sulfate, filtered, and concentrated under reduced pressure. The crude oil was purified by column chromatography on silica gel (200 g), eluting with 5% to 50% ethyl acetate/heptane. The procedure generated 2.71 g (20% yield) of 2-[3-(4-bromobutoxy)-propoxy]-tetrahydropyran as a colorless oil. $^1$H NMR (300 MHz, CDCl$_3$) δ 4.59 (t, 1H, J=2.4 Hz), 3.88-3.78 (m, 2H), 3.53-3.42 (m, 8H), 2.00-1.52 (m, 12H).

Example 26: 3-(4-Bromobutoxy)-propan-1-ol (24)

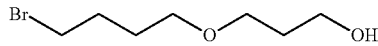

2-[3-(4-Bromobutoxy)-propoxy]-tetrahydropyran (2.70 g, 9.14 mmol) was dissolved in methanol (60 mL) under argon at room temperature. p-Toluenesulfonic acid monohydrate (5.21 g, 27.4 mmol) was added and the solution stirred overnight at room temperature. After 18 h, the solution was concentrated under reduced pressure. To the remaining oil was added ethyl acetate (80 mL) and saturated sodium bicarbonate solution (80 mL) in portions. After mixing for 20 minutes, the layers were separated, and the ethyl acetate extract was dried over sodium sulfate, filtered, and concentrated. The remaining oil was purified by flash column chromatography on silica gel (30 g), eluting with 20% to 50% ethyl acetate/heptanes. The procedure generated 1.59 g (82% yield) of 3-(4-bromobutoxy)-propan-1-ol as a colorless oil. $^1$H NMR (300 MHz, CDCl$_3$) δ 3.77 (t, 2H, J=5.7 Hz), 3.59 (t, 2H, J=6.0 Hz), 3.50-3.42 (m, 4H), 2.00-1.68 (m, 6H).

Example 27: 1-Bromo-4-(3-bromopropoxy)butane (25)

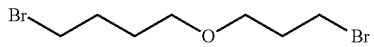

3-(4-Bromobutoxy)-propan-1-ol (1.59 g, 7.53 mmol) was dissolved in THF (25 mL) under argon at room temperature. The flask was placed in a water bath to maintain room temperature. Carbon tetrabromide (3.75 g, 11.3 mmol) and triphenylphosphine (2.94 g, 11.3 mmol) were added, and the reaction stirred for 3 h at room temperature. Heptane (30 mL) was added, and the mixture was filtered and concentrated. The remaining oil was purified by column chromatography on silica gel (25 g), eluting with 4% ethyl acetate/heptanes. The experiment generated 1.82 g (91% yield) 1-bromo-4-(3-bromopropoxy)butane as a clear oil. $^1$H NMR (300 MHz, CDCl$_3$) δ 3.55-3.42 (m, 8H), 2.13-2.05 (m, 2H), 1.99-1.90 (m, 2H), 1.76-1.67 (m, 2H).

Example 28: 6-(4-Ethoxycarbonyl-4-methylpentyloxy)-2,2-dimethylhexanoic acid ethyl ester (21)

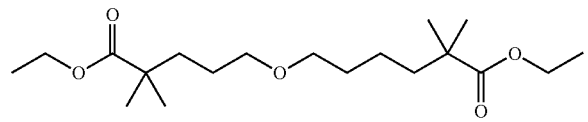 [SMILES: CCOC(=O)C(C)(C)CCCCOCCCC(C)(C)C(=O)OCC]

Ethyl isobutyrate (1.60 g, 13.8 mmol) was dissolved in dry THF (15.0 mL) under argon. The flask was cooled in a dry ice/acetone bath, and 2M LDA (6.5 mL) was added drop-wise over 5-10 minutes. The solution was stirred for 30 minutes at −78° C. 1-Bromo-4-(3-bromopropoxy)butane (693 mg, 2.53 mmol) was added, and the solution slowly warmed to room temperature and stirred overnight. After 18 h, water (25 mL) was added with ethyl acetate (25 mL). The layers were separated, and the ethyl acetate extract was washed with 10% hydrochloric acid solution (25 mL), dried over sodium sulfate, filtered, and concentrated. The remaining oil was purified by column chromatography on silica gel (20 g), eluting with 5% to 10% ethyl acetate/heptanes. The experiment generated 0.74 g (85% yield) of 6-(4-ethoxycarbonyl-4-methylpentyloxy)-2,2-dimethyl-hexanoic acid ethyl ester as a colorless oil. $^1$H NMR (300 MHz, CDCl$_3$) δ 4.10 (q, 4H, J=7.2 Hz), 3.39-3.35 (m, 4H), 1.58-1.48 (m, 8H), 1.3-1.2 (m, 8H), 1.16 (m, 12H). HRMS (ESI): [M+H]$^+$=373.2948. found 373.2948.

Example 29: 5-(Tetrahydropyran-2-yloxy)-pentan-1-ol (27)

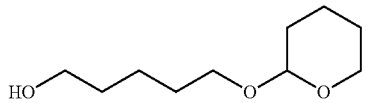 [SMILES: OCCCCCOC1CCCCO1]

1,5-Pentanediol (40.9 g, 0.45 mol) and p-toluenesulfonic acid monohydrate (0.66 g, 3.47 mmol) were dissolved in a mixture of THF (100 mL) and dichloromethane (30 mL). The flask was cooled in an ice bath, and 3,4-dihydropyran (12.0 g, 0.14 mol) was added drop-wise over 20-30 minutes. After 2 hours of stirring, the ice bath was removed, and the reaction stirred at room temperature for 2 hours. After 2 hours, the reaction was slowly poured into water (500 mL) that contained potassium carbonate (12 g). The product was extracted with ethyl acetate (2×250 mL). The combined ethyl acetate extracts were washed with water (2×250 mL) and brine (100 mL), dried over sodium sulfate, filtered, and concentrated. The crude oil was purified by column chromatography on silica gel (250 g), eluting with 3:1 heptane/ethyl acetate. The procedure generated 20.4 g (72% yield) of 5-(tetrahydropyran-2-yloxy)-pentan-1-ol, as a colorless oil. $^1$H NMR (300 MHz, CDCl$_3$) δ 4.58 (t, 1H, J=2.7 Hz), 3.90-3.75 (m, 2H), 3.67 (t, 2H, J=0.6 Hz), 3.54-3.36 (m, 2H), 2.37 (m, 2H), 1.85-1.42 (m, 4H), 1.60-1.53 (m, 12H).

Example 30: 2-[5-(5-Bromopentyloxy)-pentyloxy]-tetrahydropyran (28)

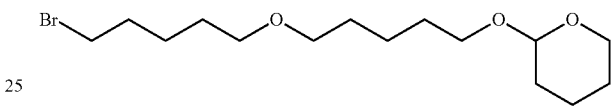

5-(Tetrahydropyran-2-yloxy)-pentan-1-ol (3.76 g, 19.9 mmol) was dissolved in dry THF (30 mL) under argon with 60% sodium hydride (0.88 g, 22 mmol). The mixture was stirred for 30 minutes at room temperature. 1,5-dibromopentane (4.6 g, 20 mmol) was added, and the mixture was heated to reflux for 22 h. After 22 h, the solution was cooled to room temperature and poured into water (150 mL) and extracted with ethyl acetate (100 mL). The ethyl acetate was dried over sodium sulfate, filtered, and concentrated under reduced pressure. The crude oil was purified by column chromatography on silica gel (200 g), eluting with 5% to 50% ethyl acetate/heptane. The procedure generated 1.49 g (21% yield) of 2-[5-(5-bromopentyloxy)-pentyloxy]-tetrahydropyran as a colorless oil. $^1$H NMR (300 MHz, CDCl$_3$) δ 4.59 (t, 1H, J=2.7 Hz), 3.89-3.70 (m, 2H), 3.53-3.35 (m, 8H), 1.91-1.39 (m, 18H).

Example 31: 5-(5-Bromopentyloxy)-pentan-1-ol (29)

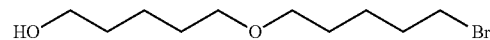 [SMILES: OCCCCCOCCCCCBr]

2-[5-(5-Bromopentyloxy)-pentyloxy]-tetrahydropyran (1.40 g, 4.15 mmol) was dissolved in methanol (30 mL) under argon at room temperature. p-Toluenesulfonic acid monohydrate (2.38 g, 12.5 mmol) was added, and the solution stirred overnight at room temperature. After 18 h, the solution was concentrated under reduced pressure. To the remaining oil was added ethyl acetate (100 mL) and saturated sodium bicarbonate solution (80 mL) in portions. After mixing for 20 minutes, the layers were separated, and the ethyl acetate extract was dried over sodium sulfate, filtered, and concentrated. The remaining oil was purified by flash column chromatography on silica gel (30 g), eluting with 20% to 50% ethyl acetate/heptanes. The procedure generated 1.0 g (95% yield) of 5-(5-bromopentyloxy)-pentan-1-ol as a colorless oil. $^1$H NMR (300 MHz, CDCl$_3$) δ 3.65 (t, 2H, J=6.6 Hz), 3.42 (t, 6H, J=6.6 Hz), 1.93-1.84 (m, 2H), 1.62-1.40 (m, 10H).

Example 32: 1-Bromo-5-(5-bromopentyloxy)-pentane (30)

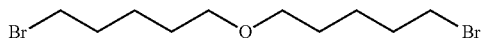 [SMILES: BrCCCCCOCCCCCBr]

5-(5-Bromopentyloxy)-pentan-1-ol (2.74 g, 10.82 mmol) was dissolved in THF (50 mL) under argon at room temperature. The flask was placed in a water bath to maintain room temperature. Carbon tetrabromide (5.38 g, 16.2 mmol) and triphenylphosphine (4.26 g, 16.2 mmol) were added and the reaction stirred for 3 h at room temperature. Heptane (50 mL) was added, and the mixture was filtered and concentrated. The remaining oil was purified by column chromatography on silica gel (80 g), eluting with 4% ethyl acetate/heptanes. The experiment generated 1.82 g (91% yield) 1-bromo-5-(5-bromopentyloxy)-pentane as a clear oil. $^1$H NMR (300 MHz, CDCl$_3$) δ 3.45-3.39 (m, 8H), 1.94-1.85 (m, 4H), 1.65-1.48 (m, 8H).

Example 33: 7-(6-Ethoxycarbonyl-6-methylheptyloxy)-2,2-dimethylheptanoic acid ethyl ester (19)

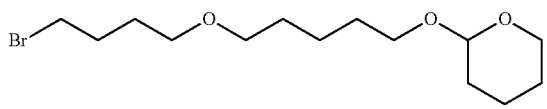

Ethyl isobutyrate (1.60 g, 13.8 mmol) was dissolved in dry THF (15.0 mL) under argon. The flask was cooled in a dry ice/acetone bath and 2M LDA (6.2 mL) was added drop-wise over 5-10 minutes. The solution was stirred for 30 minutes at −78° C. 1-Bromo-5-(5-bromopentyloxy)-pentane (800 mg, 2.53 mmol) was added and the solution slowly warmed to room temperature and stirred overnight. After 18 h, water (25 mL) was added with ethyl acetate (25 mL). The layers were separated and the ethyl acetate extract was washed with 10% hydrochloric acid solution (25 mL), dried over sodium sulfate, filtered, and concentrated. The remaining oil was purified by column chromatography on silica gel (20 g), eluting with 5% to 10% ethyl acetate/heptanes. The experiment generated 0.87 g (89% yield) of 7-(6-ethoxycarbonyl-6-methylheptyloxy)-2,2-dimethylheptanoic acid ethyl ester as a colorless oil. $^1$H NMR (300 MHz, CDCl$_3$) δ 4.12 (q, 4H, J=7.2 Hz), 3.38 (t, 4H, J=6.6 Hz), 1.58-1.49 (m, 8H), 1.38-1.2 (m, 14H), 1.16 (s, 12H). HRMS (ESI): [M+H]$^+$=387.3105. found 387.3108.

Example 34: 2-[5-(4-Bromobutoxy)-pentyloxy]-tetrahydropyran (31)

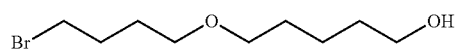 [SMILES: OCCCCCOCCCCBr]

5-(Tetrahydropyran-2-yloxy)-pentan-1-ol (6.0 g, 31.8 mmol) was dissolved in dry THF (100 mL) under argon with 60% sodium hydride (2.60 g, 39.0 mmol). The mixture was stirred for 30 minutes at room temperature. 1,4-dibromobutane (9.0 g, 41.7 mmol) was added, and the mixture was heated to reflux for 22 h. After 22 h, the solution was cooled to room temperature and poured into water (150 mL) and extracted with ethyl acetate (100 mL). The ethyl acetate was dried over sodium sulfate, filtered, and concentrated under reduced pressure. The crude oil was purified by column chromatography on silica gel (200 g), eluting with 5% to 50% ethyl acetate/heptane. The procedure generated 2.41 g (24% yield) of 2-[5-(4-bromobutoxy)-pentyloxy]-tetrahydropyran as a colorless oil. $^1$H NMR (300 MHz, CDCl$_3$) δ 4.57 (t, 1H, J=2.7 Hz), 3.89-3.70 (m, 2H), 3.51-3.47 (m, 8H), 1.99-1.38 (m, 16H).

Example 35: 5-(4-Bromobutoxy)-pentan-1-ol (35)

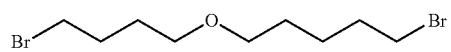

2-[5-(4-Bromobutoxy)-pentyloxy]-tetrahydropyran (2.41 g, 7.45 mmol) was dissolved in methanol (60 mL) under argon at room temperature. p-Toluenesulfonic acid monohydrate (4.25 g, 22.6 mmol) was added, and the solution stirred overnight at room temperature. After 18 h, the solution was concentrated under reduced pressure. To the remaining oil was added ethyl acetate (80 mL) and saturated sodium bicarbonate solution (80 mL) in portions. After mixing for 20 minutes, the layers were separated, and the ethyl acetate extract was dried over sodium sulfate, filtered, and concentrated. The remaining oil was purified by flash column chromatography on silica gel (25 g), eluting with 20% to 50% ethyl acetate/heptanes. The procedure generated 1.62 g (91% yield) of 5-(4-bromobutoxy)-pentan-1-ol as a colorless oil. $^1$H NMR (300 MHz, CDCl$_3$) δ 3.65 (m, 2H), 3.42 (t, 6H, J=6.6 Hz), 3.47-3.39 (m, 6H), 1.99-1.90 (m, 2H), 1.76-1.32 (m, 6H).

Example 36: 1-Bromo-5-(4-bromobutoxy)-pentane (32)

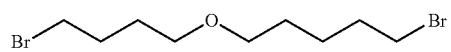

5-(4-Bromobutoxy)-pentan-1-ol (1.62 g, 6.77 mmol) was dissolved in THF (30 mL) under argon at room temperature. The flask was placed in a water bath to maintain room temperature. Carbon tetrabromide (3.36 g, 10.2 mmol) and triphenylphosphine (2.66 g, 10.2 mmol) were added, and the reaction stirred for 3 h at room temperature. Heptane (50 mL) was added and the mixture was filtered and concentrated. The remaining oil was purified by column chromatography on silica gel (40 g), eluting with 4% ethyl acetate/heptanes. The experiment generated 1.40 g (70% yield) 1-bromo-5-(4-bromobutoxy)-pentane as a clear oil. $^1$H NMR (300 MHz, CDCl$_3$) δ 3.47-3.39 (m, 8H), 2.0-1.84 (m, 4H), 1.76-1.47 (m, 6H).

Example 37: 7-(5-Ethoxycarbonyl-5-methylhexyloxy)-2,2-dimethylheptanoic acid ethyl ester (33)

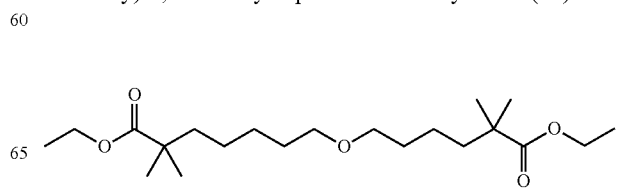

Ethyl isobutyrate (1.60 g, 13.8 mmol) was dissolved in dry THF (15.0 mL) under argon. The flask was cooled in a dry ice/acetone bath and 2M LDA (6.5 mL) was added drop-wise over 5-10 minutes. The solution was stirred for 30 minutes at −78° C. 1-Bromo-5-(4-bromobutoxy)-pentane (765 mg, 2.53 mmol) was added, and the solution slowly warmed to room temperature and stirred overnight. After 18 h, water (25 mL) was added with ethyl acetate (25 mL). The layers were separated, and the ethyl acetate extract was washed with 10% hydrochloric acid solution (25 mL), dried over sodium sulfate, filtered, and concentrated. The remaining oil was purified by column chromatography on silica gel (20 g), eluting with 5% to 10% ethyl acetate/heptanes. The experiment generated 0.74 g (79% yield) of 7-(5-Ethoxy-carbonyl-5-methylhexyloxy)-2,2-dimethylheptanoic acid ethyl ester as a colorless oil. $^1$H NMR (300 MHz, CDCl$_3$) δ 4.14 (q, 4H, J=7.2 Hz), 3.43-3.38 (m, 4H), 1.59-1.55 (m, 8H), 1.40-1.2 (m, 12H), 1.19 (m, 12H). HRMS (ESI): [M+H]$^+$=373.2948. found 373.2948.

Example 38: 3,3-Dimethyl-oxepan-2-one (25)

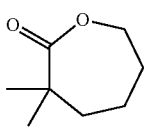

Caprolactone (2.0 g, 17.5 mmol) was dissolved in dry THF (40 mL) under argon. The flask was cooled in a dry ice/acetone bath, and 2M LDA (10 mL, 20 mmol) was added drop-wise over 5-10 minutes. The solution was stirred for 50 minutes at −78° C. Iodomethane (2.9 g, 20.5 mmol) was added, and the solution slowly warmed by removing the acetone bath and replacing it with an ice/water bath. After 1 hour, the ice/water bath was replaced with a dry ice/acetone bath, and 2M LDA (10 mL, 20 mmol) was added drop-wise over 5-10 minutes. The solution was stirred for 50 minutes at −78° C. Iodomethane (5.8 g, 41 mmol) was added, and the solution slowly warmed to 0° C. over 2 h. Water (50 mL) was added with diethyl ether (25 mL). The layers were separated, and the ether extract was washed with 10% hydrochloric acid solution (25 mL), dried over sodium sulfate, filtered, and concentrated. The remaining oil was purified by column chromatography on silica gel (50 g), eluting with 40% ethyl acetate/heptanes. The experiment generated 0.40 g (16% yield) of 3,3-dimethyl-oxepan-2-one as a colorless oil. $^1$H NMR (300 MHz, CDCl$_3$) δ 4.04 (t, 2H, J=6.0 Hz), 1.65-1.50 (m, 4H), 1.30-1.20 (m, 2H), 1.16 (s, 6H).

OTHER EMBODIMENTS

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

What is claimed is:
1. A process for making crude compound (2):

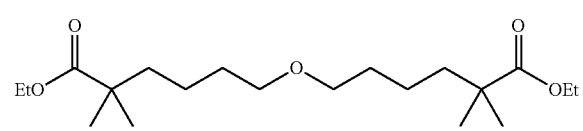

comprising:
(a) allowing ethyl isobutyrate to react with lithium diisopropylamide at a first temperature ranging from approximately −78° C. to approximately −10° C. to provide a lithium enolate of ethyl isobutyrate;
(b) allowing the lithium enolate of ethyl isobutyrate to react with compound (1)

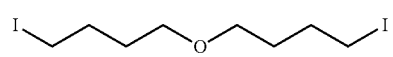

at a second temperature ranging from approximately −20° C. to 0° C. to provide a reaction mixture; and
(c) subjecting the reaction mixture to an aqueous work-up with organic solvent extraction to provide crude compound (2),
wherein steps (a) and (b) are performed in the absence of DMSO or a chelating additive and wherein the crude compound (2) is not further purified.

2. A process for making compound (3)

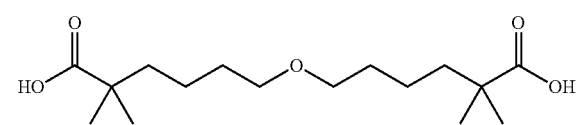

comprising:
(a) performing the process of claim 1;
(b) hydrolyzing the crude compound (2) with an alkali metal base; and
(c) acidifying the product of step (b) to provide compound (3).

3. The process of claim 2, wherein the alkali metal base is potassium hydroxide.

4. A process for making compound (4)

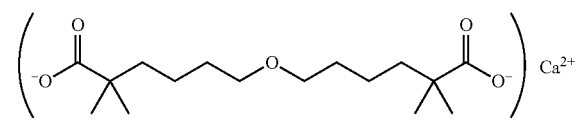

comprising:
performing the process of claim 2 and
allowing compound (3) to react with CaO to provide compound (4).

5. The process of claim 4, wherein compound (3) reacts with CaO in absolute ethanol at reflux and provides compound (4) in an ethanolic mixture.

6. The process of claim 5, further comprising the steps of:
allowing the ethanolic mixture to cool to room temperature;
diluting the ethanolic mixture with methyl t-butyl ether to provide an ethanol-and-methyl t-butyl ether mixture;
allowing compound (4) to precipitate from the ethanol-and-methyl t-butyl ether mixture; and
filtering compound (4) from the ethanol-and-methyl t-butyl ether mixture to provide a filtered compound (4).

7. A process for making a hydrate of compound (4), comprising:
performing the process of claim 6;
drying the filtered compound (4); and
hydrating the filtered compound (4) to provide the hydrate of compound (4).

8. The process of claim 7, wherein the hydrating is performed at 100° C.

9. The process of claim 1, wherein the lithium diisopropylamide is generated from diisopropylamine and n-hexyllithium.

10. The process of claim 1, wherein the second temperature is approximately −20° C.

11. The process of claim 1, wherein the second temperature is 0° C.

12. The process of claim 1, wherein crude compound (2) is made on a scale larger than 1 kg.

13. The process of claim 1, further comprising allowing crude compound (2)
to react with an aqueous solution of CaO or $Ca(OH)_2$ in water-miscible solvent to provide compound (4)

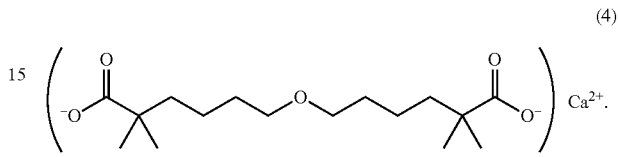

(4)

14. The process of claim 13, wherein the water-miscible solvent is DMF, DMSO, acetone, methanol, ethanol or isopropyl alcohol.

* * * * *